United States Patent
Wells et al.

(10) Patent No.: US 11,603,412 B2
(45) Date of Patent: Mar. 14, 2023

(54) ANTIBODIES AGAINST CDCP1 FOR THE TREATMENT AND DETECTION OF CANCER

(71) Applicant: The Regents of the University of California, Oakland, CA (US)

(72) Inventors: James A. Wells, San Francisco, CA (US); Alexander J. Martinko, San Francisco, CA (US); Juan E. Diaz, San Francisco, CA (US); Michael J. Hornsby, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 324 days.

(21) Appl. No.: 16/759,271

(22) PCT Filed: Oct. 25, 2018

(86) PCT No.: PCT/US2018/057587
§ 371 (c)(1),
(2) Date: Apr. 24, 2020

(87) PCT Pub. No.: WO2019/084319
PCT Pub. Date: May 2, 2019

(65) Prior Publication Data
US 2021/0179729 A1 Jun. 17, 2021

Related U.S. Application Data

(60) Provisional application No. 62/576,948, filed on Oct. 25, 2017.

(51) Int. Cl.
| | | |
|---|---|---|
| C07K 16/28 | (2006.01) | |
| A61K 47/68 | (2017.01) | |
| A61P 35/00 | (2006.01) | |
| G01N 33/574 | (2006.01) | |

(52) U.S. Cl.
CPC ...... *C07K 16/2896* (2013.01); *A61K 47/6803* (2017.08); *A61K 47/6849* (2017.08); *A61P 35/00* (2018.01); *C07K 16/2809* (2013.01); *G01N 33/57492* (2013.01); *C07K 2317/31* (2013.01); *C07K 2317/92* (2013.01); *G01N 2333/70596* (2013.01)

(58) Field of Classification Search
CPC ............ C07K 16/2896; C07K 16/2809; C07K 2317/31; C07K 2317/92; A61K 47/6803; A61K 47/6849; A61P 35/00; G01N 33/57492; G01N 2333/70596
See application file for complete search history.

(56) References Cited

U.S. PATENT DOCUMENTS

| | | |
|---|---|---|
| 2007/0031419 A1 | 2/2007 | Domon et al. |
| 2011/0052582 A1 | 3/2011 | Auer et al. |
| 2011/0070246 A1 | 3/2011 | Bossenmaier et al. |

FOREIGN PATENT DOCUMENTS

| | | |
|---|---|---|
| EP | 3031922 A1 | 6/2016 |
| WO | WO-2008133851 A1 | 11/2008 |
| WO | WO-2011023390 A1 | 3/2011 |
| WO | WO-2015082446 A1 | 6/2015 |
| WO | WO-2018213848 A1 | 11/2018 |

OTHER PUBLICATIONS

Barrett et al., (2008). "The discovery of the benzhydroxamate MEK inhibitors CI-1040 and PD 0325901," Bioorganic & Medicinal Chemistry Letters, 18:6501-4.
Bhatt et al., (2005). "Adhesion signaling by a novel mitotic substrate of src kinases," Oncogene, 24(34):5333-43, 19 pages.
Bornstein, (2015). "Antibody Drug Conjugates: Preclinical Considerations," The AAPS Journal, 17:525-34.
Buhring et al., (2004). "CDCP1 identifies a broad spectrum of normal and malignant stem/progenitor cell subsets of hematopoietic and nonhematopoietic origin," Stem Cells, 22(3):334-43.
Casar et al., (2014). "In vivo cleaved CDCP1 promotes early tumor dissemination via complexing with activated β1 integrin and induction of FAK/PI3K/Akt motility signaling," Oncogene, 33:255-268.
Czajkowsky et al., (2012). "Fc-fusion proteins: new developments and future perspectives," EMBO Mol Med, 4(10):1015-28.
Debnath et al., (2003). "Morphogenesis and oncogenesis of MCF-10A mammary epithelial acini grown in three-dimensional basement membrane cultures," Methods, 30(3):256-68.
Eser et al., (2014). "Oncogenic KRAS signalling in pancreatic cancer," British Journal of Cancer Research, 111:817-22.
Gilbert et al., (2013). "CRISPR-mediated modular RNA-guided regulation of transcription in eukaryotes," Cell, 154:442-51.
Hirai et al., (2010). "MK-2206, an Allosteric Akt Inhibitor, Enhances Antitumor Efficacy by Standard Chemotherapeutic Agents or Molecular Targeted Drugs In vitro and In vivo," Molecular Cancer Therapeutics, 9:1956-67.
Hornsby et al., (2015). "A High Through-put Platform for Recombinant Antibodies to Folded Proteins," Molecular & Cellular Proteomics, 14:2833-47.
International Search Report and Written Opinion dated Feb. 11, 2019, for PCT Patent Application No. PCT/US2018/057587 filed on Oct. 25, 2018, 18 pages.
Kollmorgen et al., (2013). "Antibody mediated CDCP1 degradation as mode of action for cancer targeted therapy," Molecular Oncology, 7(6):1142-51.
Ledford, (2015). "Cancer: The Ras renaissance," Nature, 520:278-80.
Lefranc et al., (2003). "IMGT unique numbering for immunoglobulin and T cell receptor variable domains and Ig superfamily V-like domains," Dev Comp Immunol, 27:55-77.
Martinko et al., (2018). "Targeting RAS-driven human cancer cells with antibodies to upregulated and essential cell-surface proteins," eLife, 7:e31098. 26 pages.

(Continued)

*Primary Examiner* — Nelson B Moseley, II
(74) *Attorney, Agent, or Firm* — Morrison & Foerster LLP

(57) ABSTRACT

The disclosure is related to antibodies and antibody fragments that specifically bind the CUB domain-containing protein 1 (CDCP1) and their methods and uses in treating and detecting cancers.

20 Claims, 29 Drawing Sheets

Specification includes a Sequence Listing.

(56) References Cited

OTHER PUBLICATIONS

Martins et al., (2015). "Linking Tumor Mutations to Drug Responses via a Quantitative Chemical-Genetic Interaction Map," Cancer Discovery, 5:154-67.

Moasser et al., (2001). "The Tyrosine Kinase Inhibitor ZD1839 ("Iressa") Inhibits HER2-driven Signaling and Suppresses the Growth of HER2-overexpressing Tumor Cells," Cancer Research, 61:7184-8.

Moroz et al., (2020). "Theranostic Targeting of CUB Domain Containing Protein 1 (CDCP1) in Pancreatic Cancer," Clin Cancer Res, 26:3608-3615.

Ong et al., (2006). "A practical recipe for stable isotope labeling by amino acids in cell culture (SILAC)," Nature Protocols, 1:2650-60.

Papke et al., (2017). "Drugging RAS: Know the enemy," Science, 355:1158-63, 5 pages.

Persson et al., (2013). "CDR-H3 diversity is not required for antigen recognition by synthetic antibodies," J Mol Biol, 425:803-11, 15 pages.

Pylayeva-Gupta et al., (2011). "RAS oncogenes: weaving a tumorigenic web," Nature Reviews Cancer, 11:761-74, 29 pages.

Schiess et al., (2009). "Analysis of Cell Surface Proteome Changes via Label-free, Quantitative Mass Spectrometry," Molecular & Cellular Proteomics, 8:624-38.

Singh et al., (2009). "A gene expression signature associated with "K-Ras addiction" reveals regulators of EMT and tumor cell survival," Cancer Cell, 15(6):489-500.

Stephen et al., (2014). "Dragging Ras Back in the Ring," Cancer Cell, 25(3):272-81.

Stolze et al., (2015). "Comparative analysis of KRAS codon 12, 13, 18, 61 and 117 mutations using human MCF10A isogenic cell lines," Scientific Reports, 5:8535, 9 pages.

Uekita et al., (2014). "Oncogenic Ras/ERK Signaling Activates CDCP1 to Promote Tumor Invasion and Metastasis," Molecular Cancer Research, 12(10):1449-59.

Uhlen et al., (2016). "A proposal for validation of antibodies," Nature Methods, 13: 823-7.

Wollscheid et al., (2009). "Mass-spectrometric identification and relative quantification of N-linked cell surface glycoproteins," Nature Biotechnol, 27:378-86, 20 pages.

Wu et al., (2015). "Blinatumomab: a bispecific T cell engager (BiTE) antibody against CD19/CD3 for refractory acute lymphoid leukemia," J Hematol & Oncol, 8:104, 7 pages.

Ye et al., (2016). "Comparative proteomics of a model MCF10A-$Kras^{G12V}$ cell line reveals a distinct molecular signature of the $KRas^{G12V}$ cell surface," Oncotarget, 7(52):86948-71.

Yuraszeck et al., (2017). "Translation and Clinical Development of Bispecific T-cell Engaging Antibodies for Cancer Treatment," Clinical Pharmacology & Therapeutics, 101:634-45.

SEQUENCE LISTING

```
<160> NUMBER OF SEQ ID NOS: 80

<210> SEQ ID NO 1
<211> LENGTH: 246
<212> TYPE: PRT
<213> ORGANISM: Artificial Sequence
<220> FEATURE:
<223> OTHER INFORMATION: Synthetic Construct

<400> SEQUENCE: 1

Glu Ile Ser Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Asn Phe
            20                  25                  30
```

```
Ser Ser Ser Ser Ile His Trp Val Arg Gln Ala Pro Gly Lys Gly Leu
        35                  40                  45

Glu Trp Val Ala Ser Ile Ser Ser Tyr Gly Tyr Thr Tyr Tyr Ala
 50                  55                  60

Asp Ser Val Lys Gly Arg Phe Thr Ile Ser Ala Asp Thr Ser Lys Asn
 65                  70                  75                  80

Thr Ala Tyr Leu Gln Met Asn Ser Leu Arg Ala Glu Asp Thr Ala Val
                 85                  90                  95

Tyr Tyr Cys Ala Arg Thr Val Arg Gly Ser Lys Lys Pro Tyr Phe Ser
                100                 105                 110

Gly Trp Ala Met Asp Tyr Trp Gly Gln Gly Thr Leu Val Thr Val Ser
                115                 120                 125

Ser Ala Ser Thr Lys Gly Pro Ser Val Phe Pro Leu Ala Pro Ser Ser
        130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
                180                 185                 190

Ser Leu Ser Ser Val Val Thr Val Pro Ser Ser Ser Leu Gly Thr Gln
                195                 200                 205

Thr Tyr Ile Cys Asn Val Asn His Lys Pro Ser Asn Thr Lys Val Asp
                210                 215                 220

Lys Lys Val Glu Pro Lys Ser Cys Asp Lys Thr His Thr Gly Gly Ser
225                 230                 235                 240

His His His His His His
                245

<210> SEQ ID NO 2
<211> LENGTH: 31
<212> TYPE: PRT
<213> ORGANISM: Artificial Sequence
<220> FEATURE:
<223> OTHER INFORMATION: Synthetic Construct

<400> SEQUENCE: 2

Glu Ile Ser Glu Val Gln Leu Val Glu Ser Gly Gly Gly Leu Val Gln
 1               5                  10                  15

Pro Gly Gly Ser Leu Arg Leu Ser Cys Ala Ala Ser Gly Phe Asn
                20                  25                  30

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Phe Ser Ser Ser Ser Ile
 1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct
```

-continued

<400> SEQUENCE: 4

His Trp Val Arg Gln Ala Pro Gly Lys Gly Leu Glu Trp Val Ala
1               5                   10                  15

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Ser Ile Ser Ser Ser Tyr Gly Tyr Thr Tyr
1               5                   10

<210> SEQ ID NO 6
<211> LENGTH: 39
<212> TYPE: PRT
<213> ORGANISM: Artificial Sequence
<220> FEATURE:
<223> OTHER INFORMATION: Synthetic Construct

<400> SEQUENCE: 6

Tyr Ala Asp Ser Val Lys Gly Arg Phe Thr Ile Ser Ala Asp Thr Ser
1               5                   10                  15

Lys Asn Thr Ala Tyr Leu Gln Met Asn Ser Leu Arg Ala Glu Asp Thr
            20                  25                  30

Ala Val Tyr Tyr Cys Ala Arg
        35

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

Thr Val Arg Gly Ser Lys Lys Pro Tyr Phe Ser Gly Trp Ala Met
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Synthetic Construct

<400> SEQUENCE: 8

Asp Tyr Trp Gly Gln Gly Thr Leu Val Thr Val Ser Ser
1               5                   10

<210> SEQ ID NO 9
<211> LENGTH: 226
<212> TYPE: PRT
<213> ORGANISM: Artificial Sequence
<220> FEATURE:
<223> OTHER INFORMATION: Synthetic Construct

<400> SEQUENCE: 9

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Val Ser Ser
            20                  25                  30

Ala Val Ala Trp Tyr Gln Gln Lys Pro Gly Lys Ala Pro Lys Leu Leu
            35                  40                  45

Ile Tyr Ser Ala Ser Ser Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Ser Tyr Ser Leu
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Ser Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys Gly Gly Ser Tyr Lys Asp Asp Asp
210                 215                 220

Asp Lys
225

<210> SEQ ID NO 10
<211> LENGTH: 24
<212> TYPE: PRT
<213> ORGANISM: Artificial Sequence
<220> FEATURE:
<223> OTHER INFORMATION: Synthetic Construct

<400> SEQUENCE: 10

Ser Asp Ile Gln Met Thr Gln Ser Pro Ser Ser Leu Ser Ala Ser Val
1               5                   10                  15

Gly Asp Arg Val Thr Ile Thr Cys
            20

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Arg Ala Ser Gln Ser Val Ser Ser Ala Val Ala
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Trp Tyr Gln Gln Lys Pro Gly Lys Ala Pro Lys Leu Leu Ile Tyr
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Ser Ala Ser Ser Leu Tyr Ser
1               5

<210> SEQ ID NO 14
<211> LENGTH: 34
<212> TYPE: PRT
<213> ORGANISM: Artificial Sequence
<220> FEATURE:
<223> OTHER INFORMATION: Synthetic Construct

<400> SEQUENCE: 14

Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
            20                  25                  30

Gln Gln

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Ser Ser Tyr Ser Leu Ile
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Thr Phe Gly Gln Gly Thr Lys Val Glu Ile Lys
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Leu Ser Tyr Tyr Tyr Ile
1               5

<210> SEQ ID NO 18
<211> LENGTH: 10

<212> TYPE: PRT
<213> ORGANISM: Artificial Sequence
<220> FEATURE:
<223> OTHER INFORMATION: Synthetic Construct

<400> SEQUENCE: 18

Ser Ile Tyr Ser Ser Ser Ser Tyr Thr Ser
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Ala Tyr Tyr Gly Phe
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

Ser Tyr Tyr Tyr Tyr Pro Ile
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Ile Ser Tyr Tyr Ser Met
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic Construct

<400> SEQUENCE: 22

Ser Ile Ser Pro Tyr Ser Gly Tyr Thr Ser
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct

<400> SEQUENCE: 23

Gly Tyr Tyr Ala Leu
1               5

<210> SEQ ID NO 24
<211> LENGTH: 7
<212> TYPE: PRT

```
<213> ORGANISM: Artificial Sequence
<220> FEATURE:
<223> OTHER INFORMATION: Synthetic Construct

<400> SEQUENCE: 24

Tyr Tyr Tyr Phe Tyr Pro Phe
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Construct

<400> SEQUENCE: 25

Ile Ser Tyr Tyr Tyr Met
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Ser Ile Tyr Ser Ser Tyr Gly Tyr Thr Ser
1               5                   10

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Val Tyr Tyr Gly Phe
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Ser Tyr Tyr Val Tyr Pro Ile
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Construct

<400> SEQUENCE: 29

Ile Ser Tyr Tyr Tyr Ile
1               5

<210> SEQ ID NO 30
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 30

Ser Ile Tyr Pro Tyr Tyr Gly Ser Thr Tyr
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct

<400> SEQUENCE: 31

Ala Tyr Tyr Gly Phe
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Ser Tyr Trp Ser Phe Pro Ile
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Construct

<400> SEQUENCE: 33

Leu Tyr Tyr Ser Tyr Met
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Tyr Ile Ser Pro Tyr Ser Gly Ser Thr Tyr
1               5                   10

<210> SEQ ID NO 35
<211> LENGTH: 6
<212> TYPE: PRT
<213> ORGANISM: Artificial Sequence
<220> FEATURE:
<223> OTHER INFORMATION: Synthetic Construct

<400> SEQUENCE: 35

Tyr Ser Tyr Ser Ala Leu
1               5

<210> SEQ ID NO 36
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 36

Ser Ser Trp His Tyr His Leu Phe
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic Construct

<400> SEQUENCE: 37

Ile Tyr Ser Tyr Tyr Ile
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Ser Ile Tyr Pro Tyr Tyr Gly Tyr Thr Ser
1               5                   10

<210> SEQ ID NO 39
<211> LENGTH: 5
<212> TYPE: PRT
<213> ORGANISM: Artificial Sequence
<220> FEATURE:
<223> OTHER INFORMATION: Synthetic Construct

<400> SEQUENCE: 39

Ala Tyr Tyr Gly Met
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

Ser Tyr Phe Tyr Trp Pro Ile
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct

<400> SEQUENCE: 41

Ile Ser Ser Tyr Tyr Met
1               5

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 42

Ser Ile Tyr Pro Tyr Ser Gly Tyr Thr Tyr
1               5                   10

<210> SEQ ID NO 43
<211> LENGTH: 5
<212> TYPE: PRT
<213> ORGANISM: Artificial Sequence
<220> FEATURE:
<223> OTHER INFORMATION: Synthetic Construct

<400> SEQUENCE: 43

Ala Tyr Tyr Ala Met
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic Construct

<400> SEQUENCE: 44

Ser Tyr Tyr Val Tyr Pro Ile
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Construct

<400> SEQUENCE: 45

Leu Tyr Ser Tyr Tyr Ile
1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Ser Ile Tyr Pro Tyr Tyr Ser Ser Thr Ser
1               5                   10

<210> SEQ ID NO 47
<211> LENGTH: 5
<212> TYPE: PRT
<213> ORGANISM: Artificial Sequence
<220> FEATURE:
<223> OTHER INFORMATION: Synthetic Construct

<400> SEQUENCE: 47

Tyr Tyr Tyr Ala Met
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 48

Gly Tyr Ala Gly Ser Trp His Pro Ile
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic Construct

<400> SEQUENCE: 49

Ile Tyr Ser Tyr Ser Met
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Ser Ile Ser Pro Tyr Tyr Ser Tyr Thr Ser
1               5                   10

<210> SEQ ID NO 51
<211> LENGTH: 5
<212> TYPE: PRT
<213> ORGANISM: Artificial Sequence
<220> FEATURE:
<223> OTHER INFORMATION: Synthetic Construct

<400> SEQUENCE: 51

Ala Tyr Tyr Ala Leu
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct

<400> SEQUENCE: 52

Ser Tyr Trp Tyr Tyr Pro Ile
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic Construct

<400> SEQUENCE: 53

Ile Ser Tyr Tyr Tyr Met
1               5

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 54

Ser Ile Tyr Ser Ser Ser Ser Tyr Thr Ser
1               5                   10

<210> SEQ ID NO 55
<211> LENGTH: 5
<212> TYPE: PRT
<213> ORGANISM: Artificial Sequence
<220> FEATURE:
<223> OTHER INFORMATION: Synthetic Construct

<400> SEQUENCE: 55

Ser Tyr Tyr Ala Met
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct

<400> SEQUENCE: 56

Ser Tyr Tyr Val Tyr Pro Ile
1               5

<210> SEQ ID NO 57
<211> LENGTH: 116
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Tyr
            20                  25                  30

Tyr Ile His Trp Val Arg Gln Ala Pro Gly Lys Gly Leu Glu Trp Val
        35                  40                  45

Ala Ser Ile Tyr Ser Ser Ser Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Tyr Tyr Gly Phe Asp Tyr Trp Gly Gln Gly Thr Leu Val
            100                 105                 110

Thr Val Ser Ser
        115

<210> SEQ ID NO 58
<211> LENGTH: 108
<212> TYPE: PRT
<213> ORGANISM: Artificial Sequence
<220> FEATURE:
<223> OTHER INFORMATION: Synthetic Construct

<400> SEQUENCE: 58

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Tyr Tyr Pro
                85                  90                  95

Ile Thr Phe Gly Gln Gly Thr Lys Val Glu Ile Lys
            100                 105
```

<210> SEQ ID NO 59
<211> LENGTH: 116
<212> TYPE: PRT
<213> ORGANISM: Artificial Sequence
<220> FEATURE:
<223> OTHER INFORMATION: Synthetic Construct

<400> SEQUENCE: 59

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Ser Met His Trp Val Arg Gln Ala Pro Gly Lys Gly Leu Glu Trp Val
        35                  40                  45

Ala Ser Ile Ser Pro Tyr Ser Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Ala Leu Asp Tyr Trp Gly Gln Gly Thr Leu Val
            100                 105                 110

Thr Val Ser Ser
        115
```

<210> SEQ ID NO 60
<211> LENGTH: 108
<212> TYPE: PRT
<213> ORGANISM: Artificial Sequence
<220> FEATURE:
<223> OTHER INFORMATION: Synthetic Construct

<400> SEQUENCE: 60

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Phe Tyr Pro
                85                  90                  95
```

```
Phe Thr Phe Gly Gln Gly Thr Lys Val Glu Ile Lys
                100                 105

<210> SEQ ID NO 61
<211> LENGTH: 116
<212> TYPE: PRT
<213> ORGANISM: Artificial Sequence
<220> FEATURE:
<223> OTHER INFORMATION: Synthetic Construct

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Tyr Met His Trp Val Arg Gln Ala Pro Gly Lys Gly Leu Glu Trp Val
        35                  40                  45

Ala Ser Ile Tyr Ser Ser Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Tyr Tyr Gly Phe Asp Tyr Trp Gly Gln Gly Thr Leu Val
            100                 105                 110

Thr Val Ser Ser
        115

<210> SEQ ID NO 62
<211> LENGTH: 108
<212> TYPE: PRT
<213> ORGANISM: Artificial Sequence
<220> FEATURE:
<223> OTHER INFORMATION: Synthetic Construct

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Val Tyr Pro
                85                  90                  95

Ile Thr Phe Gly Gln Gly Thr Lys Val Glu Ile Lys
            100                 105

<210> SEQ ID NO 63
<211> LENGTH: 116
<212> TYPE: PRT
<213> ORGANISM: Artificial Sequence
<220> FEATURE:
<223> OTHER INFORMATION: Synthetic Construct
```

```
<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Tyr Ile His Trp Val Arg Gln Ala Pro Gly Lys Gly Leu Glu Trp Val
        35                  40                  45

Ala Ser Ile Tyr Pro Tyr Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Tyr Tyr Gly Phe Asp Tyr Trp Gly Gln Gly Thr Leu Val
            100                 105                 110

Thr Val Ser Ser
            115

<210> SEQ ID NO 64
<211> LENGTH: 108
<212> TYPE: PRT
<213> ORGANISM: Artificial Sequence
<220> FEATURE:
<223> OTHER INFORMATION: Synthetic Construct

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Trp Ser Phe Pro
                85                  90                  95

Ile Thr Phe Gly Gln Gly Thr Lys Val Glu Ile Lys
            100                 105

<210> SEQ ID NO 65
<211> LENGTH: 117
<212> TYPE: PRT
<213> ORGANISM: Artificial Sequence
<220> FEATURE:
<223> OTHER INFORMATION: Synthetic Construct

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Tyr Met His Trp Val Arg Gln Ala Pro Gly Lys Gly Leu Glu Trp Val
        35                  40                  45

Ala Tyr Ile Ser Pro Tyr Ser Gly Ser Thr Tyr Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Ser Tyr Ser Ala Leu Asp Tyr Trp Gly Gln Gly Thr Leu
            100                 105                 110

Val Thr Val Ser Ser
        115
```

<210> SEQ ID NO 66
<211> LENGTH: 109
<212> TYPE: PRT
<213> ORGANISM: Artificial Sequence
<220> FEATURE:
<223> OTHER INFORMATION: Synthetic Construct

<400> SEQUENCE: 66

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ser Trp His Tyr His
                 85                  90                  95

Leu Phe Thr Phe Gly Gln Gly Thr Lys Val Glu Ile Lys
            100                 105
```

<210> SEQ ID NO 67
<211> LENGTH: 116
<212> TYPE: PRT
<213> ORGANISM: Artificial Sequence
<220> FEATURE:
<223> OTHER INFORMATION: Synthetic Construct

<400> SEQUENCE: 67

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Tyr Ser Tyr
             20                  25                  30

Tyr Ile His Trp Val Arg Gln Ala Pro Gly Lys Gly Leu Glu Trp Val
         35                  40                  45

Ala Ser Ile Tyr Pro Tyr Tyr Gly Tyr Thr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ala Tyr Tyr Gly Met Asp Tyr Trp Gly Gln Gly Thr Leu Val
            100                 105                 110

Thr Val Ser Ser
        115
```

-continued

<210> SEQ ID NO 68
<211> LENGTH: 108
<212> TYPE: PRT
<213> ORGANISM: Artificial Sequence
<220> FEATURE:
<223> OTHER INFORMATION: Synthetic Construct

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Phe Tyr Trp Pro
                85                  90                  95

Ile Thr Phe Gly Gln Gly Thr Lys Val Glu Ile Lys
            100                 105
```

<210> SEQ ID NO 69
<211> LENGTH: 116
<212> TYPE: PRT
<213> ORGANISM: Artificial Sequence
<220> FEATURE:
<223> OTHER INFORMATION: Synthetic Construct

<400> SEQUENCE: 69

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Tyr
            20                  25                  30

Tyr Met His Trp Val Arg Gln Ala Pro Gly Lys Gly Leu Glu Trp Val
        35                  40                  45

Ala Ser Ile Tyr Pro Tyr Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Tyr Tyr Ala Met Asp Tyr Trp Gly Gln Gly Thr Leu Val
            100                 105                 110

Thr Val Ser Ser
        115
```

<210> SEQ ID NO 70
<211> LENGTH: 108
<212> TYPE: PRT
<213> ORGANISM: Artificial Sequence
<220> FEATURE:
<223> OTHER INFORMATION: Synthetic Construct

<400> SEQUENCE: 70

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30
```

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Val Tyr Pro
                85                  90                  95

Ile Thr Phe Gly Gln Gly Thr Lys Val Glu Ile Lys
            100                 105

<210> SEQ ID NO 71
<211> LENGTH: 116
<212> TYPE: PRT
<213> ORGANISM: Artificial Sequence
<220> FEATURE:
<223> OTHER INFORMATION: Synthetic Construct

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Ser Tyr
            20                  25                  30

Tyr Ile His Trp Val Arg Gln Ala Pro Gly Lys Gly Leu Glu Trp Val
        35                  40                  45

Ala Ser Ile Tyr Pro Tyr Tyr Ser Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Ala Met Asp Tyr Trp Gly Gln Gly Thr Leu Val
            100                 105                 110

Thr Val Ser Ser
        115

<210> SEQ ID NO 72
<211> LENGTH: 110
<212> TYPE: PRT
<213> ORGANISM: Artificial Sequence
<220> FEATURE:
<223> OTHER INFORMATION: Synthetic Construct

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ala Gly Ser Trp
                85                  90                  95

His Pro Ile Thr Phe Gly Gln Gly Thr Lys Val Glu Ile Lys
              100                 105                 110

<210> SEQ ID NO 73
<211> LENGTH: 116
<212> TYPE: PRT
<213> ORGANISM: Artificial Sequence
<220> FEATURE:
<223> OTHER INFORMATION: Synthetic Construct

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Tyr
            20                  25                  30

Ser Met His Trp Val Arg Gln Ala Pro Gly Lys Gly Leu Glu Trp Val
        35                  40                  45

Ala Ser Ile Ser Pro Tyr Tyr Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Tyr Tyr Ala Leu Asp Tyr Trp Gly Gln Gly Thr Leu Val
            100                 105                 110

Thr Val Ser Ser
        115

<210> SEQ ID NO 74
<211> LENGTH: 108
<212> TYPE: PRT
<213> ORGANISM: Artificial Sequence
<220> FEATURE:
<223> OTHER INFORMATION: Synthetic Construct

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Trp Tyr Tyr Pro
                85                  90                  95

Ile Thr Phe Gly Gln Gly Thr Lys Val Glu Ile Lys
            100                 105

<210> SEQ ID NO 75
<211> LENGTH: 116
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Tyr Met His Trp Val Arg Gln Ala Pro Gly Lys Gly Leu Glu Trp Val
        35                  40                  45

Ala Ser Ile Tyr Ser Ser Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Ala Met Asp Tyr Trp Gly Gln Gly Thr Leu Val
            100                 105                 110

Thr Val Ser Ser
        115

<210> SEQ ID NO 76
<211> LENGTH: 108
<212> TYPE: PRT
<213> ORGANISM: Artificial Sequence
<220> FEATURE:
<223> OTHER INFORMATION: Synthetic Construct

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Val Tyr Pro
                85                  90                  95

Ile Thr Phe Gly Gln Gly Thr Lys Val Glu Ile Lys
            100                 105

<210> SEQ ID NO 77
<211> LENGTH: 126
<212> TYPE: PRT
<213> ORGANISM: Artificial Sequence
<220> FEATURE:
<223> OTHER INFORMATION: Synthetic Construct

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Tyr Gly Tyr Thr Tyr Tyr Ala Asp Ser Val
    50                  55                  60

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Thr Val Arg Gly Ser Lys Lys Pro Tyr Phe Ser Gly Trp Ala
            100                 105                 110

Met Asp Tyr Trp Gly Gln Gly Thr Leu Val Thr Val Ser Ser
        115                 120                 125

<210> SEQ ID NO 78
<211> LENGTH: 107
<212> TYPE: PRT
<213> ORGANISM: Artificial Sequence
<220> FEATURE:
<223> OTHER INFORMATION: Synthetic Construct

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
 65                 70                  75                  80

Glu Asp Phe Ala Thr Tyr Tyr Cys Gln Gln Ser Ser Tyr Ser Leu Ile
                85                  90                  95

Thr Phe Gly Gln Gly Thr Lys Val Glu Ile Lys
            100                 105

<210> SEQ ID NO 79
<211> LENGTH: 14
<212> TYPE: PRT
<213> ORGANISM: Artificial Sequence
<220> FEATURE:
<223> OTHER INFORMATION: Synthetic Construct

<400> SEQUENCE: 79

Asp Lys Thr His Thr Gly Gly Ser His His His His His His
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic Construct

<400> SEQUENCE: 80

Gly Gly Ser Asp Tyr Lys Asp Asp Asp Lys
1               5                   10
```

ANTIBODIES AGAINST CDCP1 FOR THE TREATMENT AND DETECTION OF CANCER

CROSS-REFERENCE TO RELATED APPLICATIONS

This application is a national phase application under 35 U.S.C. § 371 of International Application No. PCT/US2018/057587, filed Oct. 25, 2018, which claims benefit of U.S. Provisional Application No. 62/576,948, filed Oct. 25, 2017, each of which is incorporated herein by reference in its entirety.

STATEMENT REGARDING FEDERALLY SPONSORED RESEARCH OR DEVELOPMENT

This invention was made with government support under Grant Nos. F32 GM089082, U54 HG006436 and R01 CA191018 awarded by the National Institutes of Health. The government has certain rights in the invention.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 643662002200SEQLIST.TXT, date recorded: Apr. 23, 2020, size: 38 KB).

FIELD

The disclosure is related to antibodies and antibody fragments that specifically bind the CUB domain-containing protein 1 (CDCP1) and their methods and uses in treating and detecting cancers.

BACKGROUND

RAS is a family of three ubiquitously expressed small GTPases found in all animal cell types. RAS is localized to the intracellular leaflet of the cell membrane where it serves as a major communication hub that relays extracellular growth factor-dependent signaling to as many as a dozen different intracellular signaling pathways, including the classically studied MAPK and PI3K pathways. Collectively, these pathways induce dramatic changes to cells including transcriptional reprogramming, promotion of cell survival, suppression of apoptosis, metabolic rewiring, promotion of proliferation, and increased cell invasiveness. Many of these phenotypes are well-known hallmarks of cancer survival. Thus, it is not surprising that nearly one third of all human malignancies have been found to be driven by mutational activation of one of the three RAS isoforms: KRAS, NRAS and HRAS. In fact, mutations that activate RAS are found in up to 90% of certain cancer types, such pancreatic cancer. Hence oncogenic RAS has been an important focus of the cancer biology and drug discovery communities for several decades (Stephen et al., Cancer Cell, 25:272-281, 204; and Ledford, Nature, 520:278-280, 2015).

In efforts to identify tractable drug targets in RAS driven cancers, tremendous research emphasis has been placed on understanding oncogenic RAS and its role in the dysregulation of intracellular signaling pathways (Papke and Der, Science, 355:1158-1163, 2017). Despite these intense efforts to target intracellular pathways, little is understood about how RAS signaling can regulate the cell surface proteome, the surfaceome.

The surfaceome represents the dominant means by which cells communicate, interact, obtain nutrients, and engage the immune system. Overexpression of oncogenic RAS in model cell lines contributes to loss of adhesion, increased invasive properties, and evasion of immune responses, phenotypes that depend on the function of membrane proteins (Pylayeva-Gupta et al., Nature Reviews Cancer, 11:761-774, 2011). This suggests that RAS driven transcriptional reprogramming coordinately regulates the expression of cell surface proteins to exert malignant phenotypes.

Thus what is needed in the art is the identification of cell surface proteins as targets for detection and/or treatment of RAS driven cancers.

SUMMARY

In one aspect, presented herein are antibodies and antibody fragments that specifically bind the CUB domain containing protein 1 (CDCP1). In specific embodiments, the antibodies and antibody fragments specifically bind to full length CDCP1.

In another aspect, presented herein are methods of treating abnormal cells by administering to the cells an antibody or antibody fragment that specifically binds CDCP1, e.g., any one of the antibodies presented herein. In another aspect, presented herein are methods of suppressing the proliferation or growth of cancer cells, e.g., solid tumor or blood cancer cells, by contacting the cells with an antibody or antibody fragment that specifically binds CDCP1, e.g., any one of the antibodies presented herein. Further presented herein are methods of treating a subject with cancer by administering to the subject an antibody or antibody fragment that specifically binds CDCP1, e.g., any one of the antibodies presented herein.

The disclosure is also directed to method of detecting the presence of abnormal cells, e.g., cancer cells, comprising administering to the cells an antibody or antibody fragment that binds to CDCP1, e.g., any of the antibodies presented herein, and then detecting the binding of the antibody or antibody fragment to the abnormal cells.

In particular, the present disclosure is directed to antibody or antibody fragment that specifically binds CUB domain-containing protein 1 (CDCP1) comprising a peptide having the amino acid sequence of SEQ ID NO: 11 as a light chain complementarity determining region 1 (CDR1), a peptide having the amino acid sequence of SEQ ID NO:13 as a light chain CDR2, and:

(a) a light chain CDR3 having an amino acid sequence selected from the group consisting of SEQ ID NO:15, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52 and SEQ ID NO:56;

(b) a heavy chain CDR1 having an amino acid selected from the group consisting of SEQ ID NO:3, SEQ ID NO:17, SEQ ID NO:21, SEQ ID NO:25, SEQ ID NO:29, SEQ ID NO:33, SEQ ID NO:37, SEQ ID NO:41, SEQ ID NO:45, SEQ ID NO:49 and SEQ ID NO:53;

(c) a heavy chain CDR2 having an amino acid selected from the group consisting of SEQ ID NO:5, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50 and SEQ ID NO:54, and (d) a heavy chain CDR3 having an amino acid selected from the group consisting of SEQ ID NO:7, SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51 and SEQ ID NO:55. In some embodiments, the antibody or antibody fragment comprises at least one variable heavy chain domain (VH) of the heavy chain amino acid sequence of SEQ ID NO:1 and at least one variable light chain domain (VL) of the light chain amino acid sequence of SEQ ID NO:9. Also presented are pharmaceutical compositions comprising the antibody or antibody fragment and a pharmaceutically acceptable carrier.

In some embodiments, the antibody or antibody fragment described herein further comprises a cytotoxic agent conjugated to the antibody or antibody fragment. In some embodiments, the antibody or antibody fragment further comprises a binding domain that specifically binds to the CD3 region on the surface of cytotoxic T-cells. Additionally, the present disclosure is directed to methods of killing or inhibiting the growth of abnormal cells comprising administering the antibody or antibody fragment described herein to the cells. Likewise, the present disclosure is directed to methods of treating a subject for the presence of abnormal cells, the method comprising administering the pharmaceutical composition comprising the antibody or antibody fragment to the subject. In some embodiments, the abnormal cells are cancer cells. In some preferred embodiments, the abnormal cells comprise at least one mutation to a RAS oncogene in their genome. In some embodiments, the RAS oncogene is KRAS oncogene, and optionally the mutation is a G12V mutation. In some embodiments, the cancer cells are pancreatic ductal adenocarcinoma (PDAC) cells.

In further embodiments, the antibody or antibody fragment described herein further comprises a detectable label conjugated to the antibody or antibody fragment. The present disclosure is also directed to methods of detecting the presence of an abnormal cell comprising administering the antibody or antibody fragment described herein to the cells, and detecting the binding of the labeled antibody or antibody fragment to CDCP1 on the abnormal cell's surface.

Moreover, the present disclosure is directed to nucleic acids encoding the antibody or antibody fragment described herein. Also provided by the present disclosure are expression vectors comprising the nucleic acid, and host cells comprising the expression vector.

BRIEF DESCRIPTION OF THE DRAWINGS

FIG. 1A: Experimental strategy for quantitative SILAC surface proteomics to compare surfaceomes of MCF10A empty vector cells to MCF10A KRASG12V cells (Top), or MCF10A KRASG12V cells treated with vehicle versus RAS pathway inhibitors (Bottom). Cells were cultured in either light or heavy SILAC media and then processed using N-linked cell surface glycoprotein enrichment and MS-based proteomic analysis. FIG. 1B: Volcano plot of MCF10A empty vector versus MCF10A KRASG12V cell-surface mass spectrometry experiment showing log 2 fold-changes in expression (X-axis) or −log 10(p-value)s (Y-axis). Proteins with a p-value less than 0.01 and a minimum of 1.75 fold increase or decrease in SILAC ratio were considered significantly changed. The CDCP1 protein shows expression patterns that were significantly altered by oncogenic KRAS signaling and inversely altered by MEKi. FIG. 1C: Volcano plot representations of CDCP1 in MCF10A KRASG12V cells with or without treatment with the MEK inhibitor (MEKi), PD0325901 (100 nM). CDCP1 showed expression patterns that were significantly altered by oncogenic KRAS signaling and inversely altered by MEKi. FIG. 1D: Heatmap representation of the SILAC mass spectrometry data for CDCP1 protein by both KRASG12V and MEKi. FIG. 1E: Venn diagram showing overlap of targets founds in the SILAC mass spectrometry data for significantly altered proteins detected in all experiments. FIG. 1F: Heatmap representation of a comparison between RNAseq and SILAC MS-based proteomics.

FIG. 2A: Bar graph representation of the total number of unique peptides (blue) and proteins (red) identified by mass spectrometry-based proteomics for each experiment. Data was bioinformatically triaged to remove peptides not containing the characteristic asparagine deamidation generated by PNGase digest and proteins not annotated as localized to the cell surface. FIG. 2B: Venn diagram representation of the overlap of identified proteins between biological replicates demonstrates reproducibility for each experiment. FIG. 2C: Scatter plots of SILAC ratios show reproducibility between biological replicates for each experiment. FIG. 2D: Gene Ontology analysis of the cell-surface proteins significantly altered by expression of KRASG12V. FIG. 2E: Volcano plot representations of the AKTi and EGFRi mass spectrometry experiments are shown. Proteins with a p-value less than 0.01 and a minimum of 1.75 fold increase or decrease in SILAC ratio were considered significantly changed. FIG. 1F: Heatmap representation of a comparison between proteins identified in all four proteomic experiments and significantly altered (fold-change>+/−1.75; p-value<0.01) in at least one dataset.

FIG. 3A: (Left) Schematic of the Fc-fusion construct developed for rapid expression of membrane protein extracellular domains. Each extracellular domain was expressed as a TEV cleavable site-specifically biotinylated Fc-fusion; (Right) HEK293T cells stably expressing an ER-localized biotin ligase are transiently transfected with the Fc-fusion expression vector. Proteins were quantitatively biotinylated in-vivo, secreted into the cellular media, and purified by Protein A affinity purification. FIG. 3B: Strategy for phage display generation of antibodies to each RAS induced protein ECD. Proteins were immobilized on streptavidin magnetic beads and mixed with a highly diverse phage-displayed Fab library. Non-binding phage were removed by washing and phage bound protein was released by enzymatic treatment with TEV protease. Eluted phage was propagated in *E. coli* and the selection process was repeated for 3-4 rounds to enrich the library for specific protein binders. FIG. 3C: Representative flow cytometry histograms demonstrate specific cellular target engagement of Fab clones generated against seven KRAS driven surface proteins. MCF10A cells stably expressing dCas9-KRAB and a decoy sgRNA (red) or target sgRNA (blue and green) were labeled with either a negative control Fab (green) or a Fab of interest (red and blue). Fab binding to cells was detected by addition of a Protein A Alexa647 conjugate and quantification by immunofluorescence flow cytometry. FIG. 3D: Certain proteins were confirmed to be upregulated on the MCF10A KRASG12V cells by flow cytometry using specific recombinant antibodies (n=3, error bars represent SD). The table below compares log 2 fold-changes as measured by flow cytometry, SILAC proteomics, and RNAseq. FIG. 3E: Representative immunofluorescence images demonstrate orthogonal confirmation of KRAS driven differential expression and cell surface localization of target proteins. FIG. 3F: Heatmap representation of flow cytometry median fluorescent intensity values for CDCP1 Fab against nine tumorigenic cell lines. CDCP1 stands out as being highly expressed on nearly every cell line harboring a RAS mutation.

FIG. 4A-4D depicts the generation and validation of antibodies to oncogenic KRAS upregulated surface proteins. FIG. 4A: Western blot analysis of Fc-fusion protein endogenous biotinylation. Expression in WT HEK293T cells was compared to expression in HEK293T cells stably expressing BirA localized to the cytosol (Left), the endoplasmic reticulum (Middle), or secreted into the extracellular space (Right). The amount of biotinylation was estimated by assessment of band migration by SDS-PAGE after co-incubation of the purified Fc-fusion with streptavidin. Expression in cells expressing ER-localized BirA showed quantitative biotinylation (>98%). FIGS. 4B1 and 4B-2: Phage ELISAs from selections against CDCP1 protein elevated in expression level by oncogenic KRAS signaling in MCF10As. Phage clones that showed strong binding to cognate protein Fc-fusions but little detectable binding to the isolated Fc-domain were advanced for further characterization. FIG. 4C: Schematic of the construct used to display each protein on the surface of HEK293 (T-Rex-293) cells for validation of antibody specificity. FIG. 4D: Representative flow cytometry histograms demonstrate specific cellular target engagement of Fab clones (including CDCP1-4A06, referred to herein as CDCP1-002) raised against seven RAS driven surface proteins.

FIG. 5A: Data from The Cancer Genome Atlas reveals that CDCP1 expression level correlates with KRAS mutational status in human pancreatic cancers (p-value 0.0006). FIG. 5B: Profiling of a panel of pancreatic ductal adenocarcinoma cells by flow cytometry demonstrates that CDCP1 is highly expressed on PDAC cells. Remarkably, CDCP1 was not detectably expressed on non-tumorogenic cells derived from the same tissue origin. FIG. 5C: A schematic representation of the antibody drug conjugate cell-killing assay. Cells were treated with a primary IgG that targets CDCP1 and a secondary anti-human IgG conjugated to the cytotoxic drug monomethyl auristatin F (MMAF). Cellular viability was quantified by CELLTITER-GLO® luminescent cell viability assay (Promega, Corp.) after 72 hours incubation with antibody treatment. FIG. 5D: Dose dependent antibody drug conjugate mediated cell killing was only observed in the human pancreatic adenocarcinoma cells (HPAC) tumorigenic cells and not in the non-tumorogenic human pancreatic normal epithelial (HPNE) cells (n=3, error bars represent SD). FIG. 5E: Sub-nanomolar treatment with a CDCP1 IgG was sufficient to selectively kill greater than 50% of HPAC cells, but only when in combination with a stoichiometric excess of the secondary antibody drug conjugate (n=3, error bars represent SD). FIG. 5F: Schematic of the experimental setup for the flow cytometry-based T-cell activation assay used to profile BiTE activity. Cells were incubated with HPAC or HPNE target cells in the presence or absence of antibody treatment. After overnight incubation, T-cell activation was quantified via the expression of NFAT-dependent GFP reporter gene. FIG. 5G: Jurkat cells were significantly activated when treated with 1 nM BiTE in the presence of HPAC target cells as compared to HPNE control cells. Importantly treatment with the CDCP1 BiTE alone or with Fab lacking the CD3 targeting component resulted in no significant T-cell activation.

FIG. 6A: Bmax determination for CDCP1 expression on HPAC, SW620, MiaPaCa2, and A549 cells using a titration of $^{125}$I labeled CDCP1-002. FIG. 6B: GTEx database analysis of the tissue specific gene-expression of CDCP1 shows limited expression in normal tissues. FIG. 6C: GTEx database analysis of the tissue specific gene-expression of HER2, a classically targeted cell-surface protein overexpressed in sub-types of breast cancer.

FIG. 7A: A schematic of the RAS signaling pathway and the pharmacological approach used to elucidate the mechanism by which RAS signaling influences CDCP1 expression. Cells were treated with one of five inhibitors and CDCP1 expression was profiled by flow cytometry and western blotting after 48 hours of treatment. FIG. 7B: Expression levels of CDCP1 on MCF10A KRASG12V cells were profiled by intact cell flow cytometry (top) and western blotting (bottom) under the influence of different signaling inhibitors. Data confirms that pharmacological blockade of MAPK signaling is sufficient to shut down cellular expression and cell-surface localization of CDCP1. Expression levels of CDCP1 were insensitive to treatment with the EGFR inhibitor, Gefitinib, indicating that RAS plays the major driving role the expression of CDCP1. FIG. 7C: Expression levels of CDCP1 on two KRAS mutant cancer cell lines were profiled by intact cell flow cytometry (top) and western blotting (bottom). Consistent with proteomics observations in the MCF10A KRASG12V cells, expression and cell-surface localization of CDCP1 was depleted by MEK inhibition but refractory to EGFR inhibition. FIG. 7D: Representative microPET images of four immunocompromised nu/nu mice bearing cancer xenografts targeted with a $^{89}$Zr-labeled CDCP1 Fab. Images over time show the tumor-specific expression of CDCP1, as well as the persistent binding of the Fab to the tumor over 24 hours (Left). Importantly, when the same Fab was heat denatured prior to injection or when a negative control xenograft was used, there was no observable uptake of the $^{89}$Zr-Fab (Middle and Right). Remarkably, no uptake was observed in the mouse treated with a sub-toxic dose of MEKi prior to imaging, demonstrating the coupling of CDCP1 expression and MAPK pathway signaling in vivo. FIG. 7E: Quantification of tumor specific bio-distribution of the CDCP1 $^{89}$Zr-Fab in tumor bearing nu/nu mice (n=5 per treatment arm) confirms the trends observed by microPET imaging. Tumor localization of $^{89}$Zr-Fab was antigen dependent and ablated by specific inhibition of MAPK signaling.

DETAILED DESCRIPTION

Figure 1A:
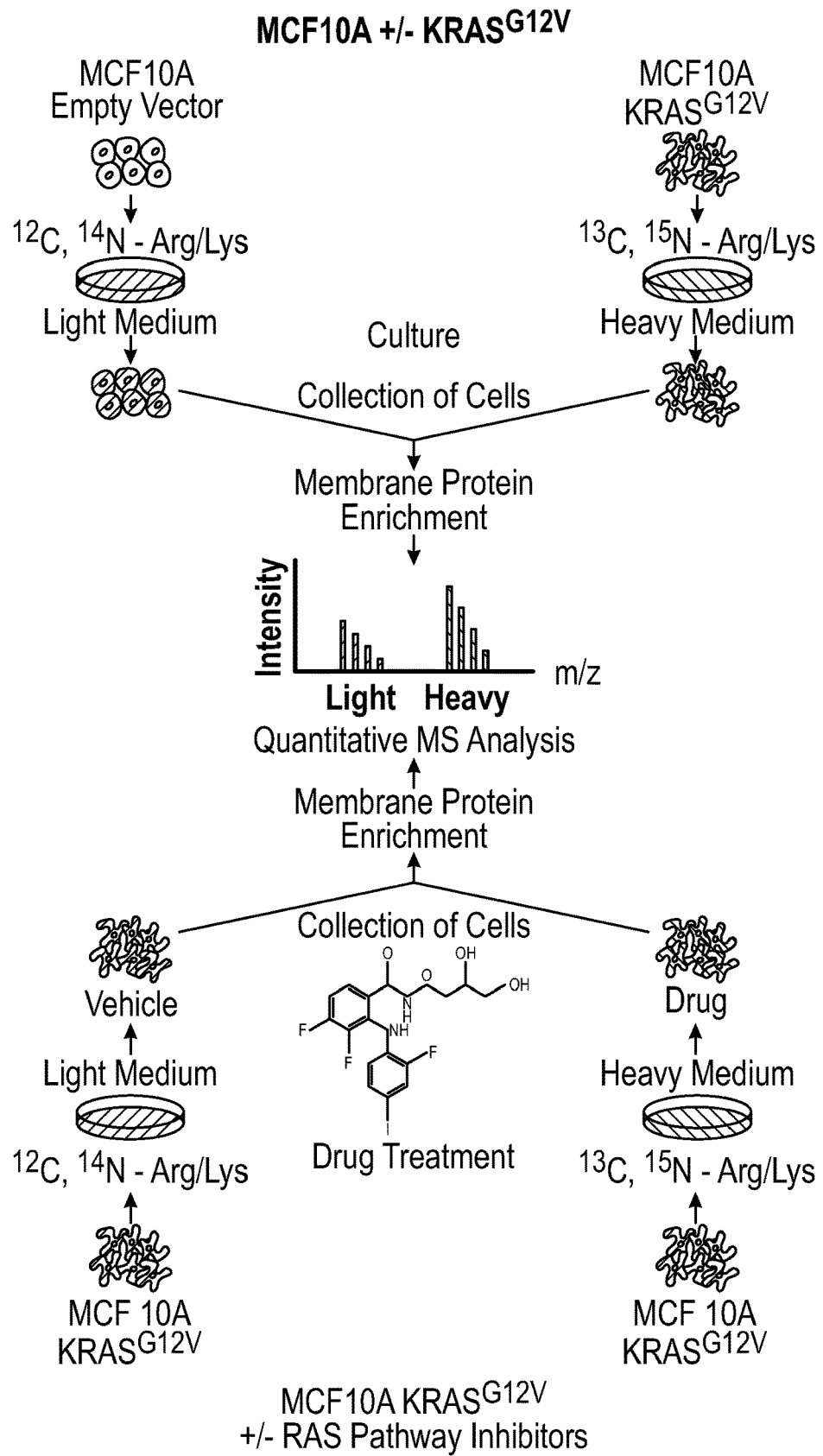
FIG. 1A-1F illustrates that oncogenic KRAS signaling coordinately regulates the expression of cell surface proteins in a model epithelial cell.

While there have been tremendous efforts to target oncogenic RAS signaling from inside the cell, little effort has focused on the cell-surface. The present disclosure describes use of quantitative surface proteomics to reveal that the CUB domain containing protein 1 (CDCP1) is upregulated on cells transformed with KRASG12V, and driven by MAPK pathway signaling. A toolkit of recombinant antibodies to CDCP1 were generated and subsequently used to determine that CDCP1 is broadly distributed on cancer cell lines harboring RAS mutations. In parallel, a cell-surface CRISPRi screen was employed. Antibodies targeting CDCP1, a protein common to the proteomics and CRISPRi datasets, can be leveraged to deliver cytotoxic and immunotherapeutic payloads to RAS-transformed cancer cells. The anti-CDCP1 antibodies can also be used to assess RAS signaling status in vivo. Taken together, this work presents a technological platform for attacking RAS from outside the cell.

As used herein and in the appended claims, the singular forms "a," "an," and "the" include plural references unless indicated otherwise. For example, "an" excipient includes one or more excipients.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting of" and "consisting essentially of" embodiments.

I. Anti-CDCP1 Antibodies

In one aspect, provided herein are antibodies and antibody fragments that specifically bind the CUB-domain containing protein 1 (CDCP1). The CDCP1 protein, which is also referred to in the literature as SIMA135, CD318 and TRASK (transmembrane and associated with src kinases), has a large extracellular domain of 665 amino acids and contains three CUB domains. The CUB domains mediate protein-protein interactions and are presumed to be involved in cell adhesion and interaction with the extracellular matrix (Bhatt et al., Oncogene, 24:5333-5343, 2005; and Casar et al., Oncogene, 33:255-268, 2014). For example, CDCP1 cellular adhesion plays a role in controlling phosphorylation status in at least keratinocytes. As described herein, CDCP1 expression appears to be regulated by RAS.

As used herein, CUB domain-containing protein 1 (CDCP1) is meant to include the extracellular portion of the full length CDCP1 protein. As is well known in the art, CDCP1 is a glycosylated transmembrane protein with an extracellular domain of approximately 638 amino acids. The full length human version of CDCP1, after cleaving of the signal peptide (residues 1-29 of the full length chain) is 807 amino acids in length. The amino acid sequence of human CDCP1 is found at Uniprot Record No. Q9H5V8, the entirely of which is incorporated by reference. As used herein, CDCP1 includes the human version and any natural variant thereof. For example, one natural variant of CDCP1 includes a Q525R mutation (with the numbering including the first 29 amino acids as the signal sequence that is subsequently cleaved), which is in the extracellular domain of the CDCP1. The antibody or antibody fragments of the present disclosure bind to the extracellular portion of the "mature" (lacking signal peptide) version of the CDCP1 protein.

As used herein, the term "antibody" refers to an immunoglobulin molecule that can specifically bind to a particular antigen. Antibodies have different isotypes or classes, such as but not limited to the isotypes known as IgA, IgD, IgE, IgG and IgM. The term antibody as used herein encompasses all isotypes. As is well understood in the art, a typical antibody is composed of two identical heavy chains and two identical light chains. The heavy chains are joined to one another via at least one disulfide bond and each light chain is joined to a heavy chain via a disulfide bond. Each heavy and light chain generally comprises a "variable domain" (VH and VL, respectively) at or near the N-terminus of the antibody. The variable domains for each chain are critical for antigen binding. The light chain contains one additional "constant region" (CL) and the heavy chain contains three or four additional constant regions (CH1, CH2, CH3, CH4). Thus, in specific embodiments, any of the antibodies provided herein may be IgA antibodies, IgD antibodies, IgE antibodies, IgG antibodies, or IgM antibodies. In other specific embodiments, any of the antibodies provided herein is a monoclonal antibody, e.g., comprising two identical light chains and two identical heavy chains.

The VH and VL chains generally each comprise three complementarity determining regions (CDRs) that determine antigen binding specificity. The CDRs can also be referred to as "loops" or "L regions." The framework regions (FRs) are amino acid stretches within the VH and VL intervening between the CDRs. In full length VH and VL chains, each chain comprises three CDRs (Ls) and four framework regions (FR1 through FR4). The 4 FRs are separated respectively by the three CDRs (CDR1, CDR2, CDR3) or (L1, L2, L3). The CDRs, and in particular the CDR3 regions, and more particularly the VH CDR3, may, in certain embodiments, be largely responsible for antibody specificity.

A Fab fragment (fragment antigen-binding) is a region of an antibody that binds to antigens. Fab fragments may comprise one constant domain (CL and CH1) and one variable chain (VL and VH) of each of the heavy and the light chain. F(ab')$_2$ refers to an antibody fragment comprising a Fab dimer. Fab and F(ab')$_2$ may be generated by recombinant technology or by cleavage of an antibody or a fragment of antibody.

In some embodiments, the present disclosure provides monoclonal antibodies, or antigen-binding fragments thereof, which specifically bind to human CDCP1. The monoclonal antibody may be a human antibody, a humanized antibody, or a chimeric antibody, and may include a constant region. In some embodiments, the human constant region is selected from the group consisting of IgG1, IgG2, IgG3 and IgG4 constants regions. In some embodiments, the antigen-binding fragment is selected from the group consisting of Fab, Fab'-SH, F(ab')$_2$, scFV and Fv fragments.

An antibody fragment may comprise part of an immunoglobulin molecule or a combination of parts of immunoglobulin molecules. In specific embodiments, the antibody fragments provided herein retain the ability to bind the same antigen that the full-length antibody binds, e.g., CDCP1, e.g., a CUB domain of CDCP1. The fragment may or may not bind to the exact same epitope as the full length antibody from which the fragment is derived. Antibody fragments include but are not limited to F(ab')$_2$, Fab, Fv and Fc fragment, as well as fusion peptide such as single chain Fv (scFv) fragments. ScFv fragments are single chain peptides that contain a VH chain and the VL chain, e.g., any of the VH and VL chains provided herein, linked to one another via a linker peptide. In specific embodiments, the connector peptide ranges from about two to about 50 amino acids. In some embodiments, the connector peptide ranges from about two to about 10 amino acids, from about 10 to about 15 amino acids, from about 15 to about 20 amino acids, from about 20 to about 25 amino acids, from about 25 to about 30 amino acids, from about 30 to about 35 amino acids, from about 35 to about 40 amino acids, from about 40 to about 45 amino acids or from about 45 to about 50 amino acids. The ScFv may retain the antigen binding ability of the original immunoglobulin molecule.

In select embodiments, the antibodies or antibody fragments provided herein comprise the variable heavy chain (VH) amino acid sequence of the Fab heavy chain of SEQ ID NO:1:

```
EISEVQLVES GGGLVQPGGS LRLSCAASGF NFSSSSIHWV
RQAPGKGLEW VASISSSYGY TYYADSVKGR FTISADTSKN
TAYLQMNSLR AEDTAVYYCA RTVRGSKKPY FSGWAMDYWG
QGTLVTVSSA STKGPSVFPL APSSKSTSGG TAALGCLVKD
YFPEPVTVSW NSGALTSGVH TFPAVLQSSG LYSLSSVVTV
PSSSLGTQTY ICNVNHKPSN TKVDKKVEPK SCDKTHTGGS
HHHHHH.
```

In other embodiments, the antibodies or antibody fragments of the present disclosure comprise the variable light chain (VL) amino acid sequence of the Fab heavy chain of SEQ ID NO:9:

```
SDIQMTQSPS SLSASVGDRV TITCRASQSV SSAVAWYQQK
PGKAPKLLIY SASSLYSGVP SRFSGSRSGT DFTLTISSLQ
PEDFATYYCQ QSSYSLITFG QGTKVEIKRT VAAPSVFIFP
PSDSQLKSGT ASVVCLLNNF YPREAKVQWK VDNALQSGNS
QESVTEQDSK DSTYSLSSTL TLSKADYEKH KVYACEVTHQ
GLSSPVTKSF NRGECGGSDY KDDDDK.
```

In still other embodiments, the antibodies or antibody fragments comprise both the VH of SEQ ID NO:1 and the VL of SEQ ID NO:9. The antibody or antibody fragment (i.e., CDCP1-binding fragment) containing the VH and VL of SEQ ID NO:1 and SEQ ID NO:9, respectively, is referred to herein as CDCP1-001. As used herein, the term "antibody fragment" refers to an "antigen-binding fragment" (i.e., CDCP1-binding fragment) of the designated antibody.

The underlined portions of the VH and VL amino acid sequences of the Fab heavy and light chains above represent the complementarity determining regions (CDRs) in each chain, as per the IMGT system (Lefranc et al., Dev Comp Immunol, 27:55-77, 2003). For example, CDR1 of the VH is the amino acid sequence FSSSSI (SEQ ID NO: 3), CDR2 of the VH is the amino acid sequence SISSSYGYTY (SEQ ID NO: 5) and CDR3 of the VH is the amino acid sequence is TVRGSKKPYFSGWAM (SEQ ID NO: 7). The non-underlined portions of the sequences above represent the framework regions (FRs). For example, FR1 of the VH is the amino acid sequence EISEVQLVESGGGLVQPGGSLRLS-CAASGFN (SEQ ID NO:2), FR2 of the VH is the amino acid sequence HWVRQAPGKGLEWVA (SEQ ID NO:4), FR3 of the VH is the amino acid sequence YADSVKGRFTI-SADTSKNTAYLQMNSLRAEDTAVYYCAR (SEQ ID NO:6) and FR4 of the VH is the amino acid sequence DYWGQGTLVTVSS (SEQ ID NO:8). Likewise, CDR1 of VL is the amino acid sequence RASQSVSSAVA (SEQ ID NO:11), CDR2 of VL is the amino acid sequence SASSLYS (SEQ ID NO:13) and CDR3 of the VL is the amino acid sequence SSYSLI (SEQ ID NO:15). The FR1 of the VL is the amino acid sequence SDIQMTQSPSSL-SASVGDRVTITC (SEQ ID NO:10), FR2 of VL is the amino acid sequence WYQQKPGKAPKLLIY (SEQ ID NO:12), FR3 of VL is the amino acid sequence GVPSRFSGSRSGTDFTLTISSLQPEDFATYYCQQ (SEQ ID NO:14) and FR4 of the VL is the amino acid sequence TFGQGTKVEIK (SEQ ID NO:16). In the exemplary Fab heavy and light chain sequences shown above, DKTH-TGGSHHHHHH (SEQ ID NO:79) and GGSDYKDDDDK (SEQ ID NO:80) are affinity tags.

In other embodiments, the antibodies or antibody fragments comprise VH FR1-FR4, VL FR1-FR4 and VL CDR1-CDR2 of the CDCP1-001 fragment disclosed above, and different VH CDR1-CDR3 and VL CDR3, as shown below in Table A-1. In another embodiment, the antibodies or antibody fragments comprise VL CDR1-CDR2 of the CDCP1-001 fragment, and different VH CDR1-CDR3 VL CDR3, as shown below in Table A-1. In other words, in these specific embodiments, the antibodies or antibody fragments CDCP1-002 through CDCP1-011 would possess the VH CDRs and the VL CDR3 listed in Table A-1, respectively, plus the VL CDR1 (SEQ ID NO:11) and VL CDR2 (SEQ ID NO:13) from the CDCP1-001 fragment. For example, in one embodiment, the VH CDCP1-002 comprises the amino acid sequence from N-terminus to C-terminus: SEQ ID NO:2 (VH FR1), SEQ ID NO: 17 (VH CDR1), SEQ ID NO:4 (VH FR2), SEQ ID NO:18 (VH CDR2), SEQ ID NO:6 (VH FR3), SEQ ID NO:19 (VH CDR3) and SEQ ID NO:8 (VH FR4). Similarly, in one embodiment, the VL CDCP1-002 comprises the amino acid sequence from N-terminus to C-terminus: SEQ ID NO:10 (VL FR1), SEQ ID NO: 11 (VH CDR1), SEQ ID NO:12 (VH FR2), SEQ ID NO:13 (VH CDR2), SEQ ID NO:14 (VH FR3), SEQ ID NO:20 (VH CDR3) and SEQ ID NO:16 (VH FR4). The combination of VH FRs1-4 and VH CDRs1-3, in proper order, make up the VH chain for each of the 001-011 anti-CDCP1 antibody fragments. Similarly, the combination of VL FRs1-4 and VL CDRs1-3, in proper order, make up the VL chain for each of the 001-011 anti-CDCP1 antibody fragments.

TABLE A-1

Sequences of CDRs of Anti-CDCP1 Fabs

| Fab Region | CDR1 | CDR2 | CDR3 |
| --- | --- | --- | --- |
| CDCP1-001 $V_H$ | FSSSSI (SEQ ID NO: 3) | SISSSYGYTY (SEQ ID NO: 5) | TVRGSKKPYFSGWAM (SEQ ID NO: 7) |
| CDCP1-001 $V_L$ | RASQSVSSAVA (SEQ ID NO: 11) | SASSLYS (SEQ ID NO: 13) | SSYSLI (SEQ ID NO: 15) |
| CDCP1-002 $V_H$ | LSYYYI (SEQ ID NO: 17) | SIYSSSSYTS (SEQ ID NO: 18) | AYYGF (SEQ ID NO: 19) |
| CDCP1-002 $V_L$ | RASQSVSSAVA (SEQ ID NO: 11) | SASSLYS (SEQ ID NO: 13) | SYYYYPI (SEQ ID NO: 20) |

TABLE A-1-continued

Sequences of CDRs of Anti-CDCP1 Fabs

| Fab Region | CDR1 | CDR2 | CDR3 |
|---|---|---|---|
| CDCP1-003 $V_H$ | ISYYSM (SEQ ID NO: 21) | SISPYSGYTS (SEQ ID NO: 22) | GYYAL (SEQ ID NO: 23) |
| CDCP1-003 $V_L$ | RASQSVSSAVA (SEQ ID NO: 11) | SASSLYS (SEQ ID NO: 13) | YYYFYPF (SEQ ID NO: 24) |
| CDCP1-004 $V_H$ | ISYYYM (SEQ ID NO: 25) | SIYSSYGYTS (SEQ ID NO: 26) | VYYGF (SEQ ID NO: 27) |
| CDCP1-004 $V_L$ | RASQSVSSAVA (SEQ ID NO: 11) | SASSLYS (SEQ ID NO: 13) | SYYVYPI (SEQ ID NO: 28) |
| CDCP1-005 $V_H$ | ISYYYI (SEQ ID NO: 29) | SIYPYYGSTY (SEQ ID NO: 30) | AYYGF (SEQ ID NO: 31) |
| CDCP1-005 $V_L$ | RASQSVSSAVA (SEQ ID NO: 11) | SASSLYS (SEQ ID NO: 13) | SYWSFPI (SEQ ID NO: 32) |
| CDCP1-006 $V_H$ | LYYSYM (SEQ ID NO: 33) | YISPYSGSTY (SEQ ID NO: 34) | YSYSAL (SEQ ID NO: 35) |
| CDCP1-006 $V_L$ | RASQSVSSAVA (SEQ ID NO: 11) | SASSLYS (SEQ ID NO: 13) | SSWHYHLF (SEQ ID NO: 36) |
| CDCP1-007 $V_H$ | IYSYYI (SEQ ID NO: 37) | SIYPYYGYTS (SEQ ID NO: 38) | AYYGM (SEQ ID NO: 39) |
| CDCP1-007 $V_L$ | RASQSVSSAVA (SEQ ID NO: 11) | SASSLYS (SEQ ID NO: 13) | SYFYWPI (SEQ ID NO: 40) |
| CDCP1-008 $V_H$ | ISSYYM (SEQ ID NO: 41) | SIYPYSGYTY (SEQ ID NO: 42) | AYYAM (SEQ ID NO: 43) |
| CDCP1-008 $V_L$ | RASQSVSSAVA (SEQ ID NO: 11) | SASSLYS (SEQ ID NO: 13) | SYYVYPI (SEQ ID NO: 44) |
| CDCP1-009 $V_H$ | LYSYYI (SEQ ID NO: 45) | SIYPYYSSTS (SEQ ID NO: 46) | YYYAM (SEQ ID NO: 47) |
| CDCP1-009 $V_L$ | RASQSVSSAVA (SEQ ID NO: 11) | SASSLYS (SEQ ID NO: 13) | GYAGSWHPI (SEQ ID NO: 48) |
| CDCP1-010 $V_H$ | IYSYSM (SEQ ID NO: 49) | SISPYYSYTS (SEQ ID NO: 50) | AYYAL (SEQ ID NO: 51) |
| CDCP1-010 $V_L$ | RASQSVSSAVA (SEQ ID NO: 11) | SASSLYS (SEQ ID NO: 13) | SYWYYPI (SEQ ID NO: 52) |
| CDCP1-011 $V_H$ | ISYYYM (SEQ ID NO: 53) | SIYSSSSYTS (SEQ ID NO: 54) | SYYAM (SEQ ID NO: 55) |
| CDCP1-011 $V_L$ | RASQSVSSAVA (SEQ ID NO: 11) | SASSLYS (SEQ ID NO: 13) | SYYVYPI (SEQ ID NO: 56) |

TABLE A-2

Sequences of Variable Regions of Anti-CDCP1 Fabs^
Fab Variable Region

CDCP1-002 $V_H$ (SEQ ID NO: 57)
EVQLVES GGGLVQPGGS LRLSCAASGF NLSYYYIHWV RQAPGKGLEW VASIYSSSY
TSYADSVKGR FTISADTSKN TAYLQMNSLR AEDTAVYYCA RAYYGFDYWG QGTLVTVSS

CDCP1-002 $V_L$ (SEQ ID NO: 58)
DIQMTQSPS SLSASVGDRV TITCRASQSV SSAVAWYQQK PGKAPKLLIY SASSLYSGVP
SRFSGSRSGT DFTLTISSLQ PEDFATYYCQ QSYYYPITFG QGTKVEIK

TABLE A-2-continued

Sequences of Variable Regions of Anti-CDCP1 Fabs^
Fab Variable Region

CDCP1-003 V_H
(SEQ ID NO: 59)
EVQLVES GGGLVQPGGS LRLSCAASGF N<u>ISYYSM</u>HWV RQAPGKGLEW VA<u>SISPYSGY</u>
<u>TS</u>YADSVKGR FTISADTSKN TAYLQMNSLR AEDTAVYYCA R<u>GYYAL</u>DYWG QGTLVTVSS

CDCP1-003 V_L
(SEQ ID NO: 60)
DIQMTQSPS SLSASVGDRV TITC<u>RASQSV SSAVA</u>WYQQK PGKAPKLLIY <u>SASSLYS</u>GVP
SRFSGSRSGT DFTLTISSLQ PEDFATYYCQ <u>QYYYFYPF</u>TFG QGTKVEIK

CDCP1-004 V_H
(SEQ ID NO: 61)
EVQLVES GGGLVQPGGS LRLSCAASGF N<u>ISYYYM</u>HWV RQAPGKGLEW VA<u>SIYSSYGY</u>
<u>TS</u>YADSVKGR FTISADTSKN TAYLQMNSLR AEDTAVYYCA R<u>VYYGF</u>DYWG QGTLVTVSS

CDCP1-004 V_L
(SEQ ID NO: 62)
DIQMTQSPS SLSASVGDRV TITC<u>RASQSV SSAVA</u>WYQQK PGKAPKLLIY <u>SASSLYS</u>GVP
SRFSGSRSGT DFTLTISSLQ PEDFATYYCQ <u>QSYYVYPI</u>TFG QGTKVEIK

CDCP1-005 V_H
(SEQ ID NO: 63)
EVQLVES GGGLVQPGGS LRLSCAASGF N<u>ISYYYI</u>HWV RQAPGKGLEW VA<u>SIYPYYGS</u>
<u>TY</u>YADSVKGR FTISADTSKN TAYLQMNSLR AEDTAVYYCA R<u>AYYGF</u>DYWG QGTLVTVSS

CDCP1-005 V_L
(SEQ ID NO: 64)
DIQMTQSPS SLSASVGDRV TITC<u>RASQSV SSAVA</u>WYQQK PGKAPKLLIY <u>SASSLYS</u>GVP
SRFSGSRSGT DFTLTISSLQ PEDFATYYCQ <u>QSYWSFPI</u>TFG QGTKVEIK

CDCP1-006 V_H
(SEQ ID NO: 65)
EVQLVES GGGLVQPGGS LRLSCAASGF N<u>LYYSYM</u>HWV RQAPGKGLEW VA<u>YISPYSGS</u>
<u>TY</u>YADSVKGR FTISADTSKN TAYLQMNSLR AEDTAVYYCA R<u>YSYSAL</u>DYWG QGTLVTVSS

CDCP1-006 V_L
(SEQ ID NO: 66)
DIQMTQSPS SLSASVGDRV TITC<u>RASQSV SSAVA</u>WYQQK PGKAPKLLIY <u>SASSLYS</u>GVP
SRFSGSRSGT DFTLTISSLQ PEDFATYYCQ <u>QSSWHYHLF</u>TFG QGTKVEIK

CDCP1-007 V_H
(SEQ ID NO: 67)
EVQLVES GGGLVQPGGS LRLSCAASGF N<u>IYSYYI</u>HWV RQAPGKGLEW VA<u>SIYPYYGY</u>
<u>TS</u>YADSVKGR FTISADTSKN TAYLQMNSLR AEDTAVYYCA R<u>AYYGM</u>DYWG QGTLVTVSS

CDCP1-007 V_L
(SEQ ID NO: 68)
DIQMTQSPS SLSASVGDRV TITC<u>RASQSV SSAVA</u>WYQQK PGKAPKLLIY <u>SASSLYS</u>GVP
SRFSGSRSGT DFTLTISSLQ PEDFATYYCQ <u>QSYFYWPI</u>TFG QGTKVEIK

CDCP1-008 V_H
(SEQ ID NO: 69)
EVQLVES GGGLVQPGGS LRLSCAASGF N<u>ISSYYM</u>HWV RQAPGKGLEW VA<u>SIYPYSGY</u>
<u>TY</u>YADSVKGR FTISADTSKN TAYLQMNSLR AEDTAVYYCA R<u>AYYAM</u>DYWG QGTLVTVSS

CDCP1-008 V_L
(SEQ ID NO: 70)
DIQMTQSPS SLSASVGDRV TITC<u>RASQSV SSAVA</u>WYQQK PGKAPKLLIY <u>SASSLYS</u>GVP
SRFSGSRSGT DFTLTISSLQ PEDFATYYCQ <u>QSYYVYPI</u>TFG QGTKVEIK

CDCP1-009 V_H
(SEQ ID NO: 71)
EVQLVES GGGLVQPGGS LRLSCAASGF N<u>LYSYYI</u>HWV RQAPGKGLEW VA<u>SIYPYYSS</u>
<u>TS</u>YADSVKGR FTISADTSKN TAYLQMNSLR AEDTAVYYCA R<u>YYYAM</u>DYWG QGTLVTVSS

CDCP1-009 V_L
(SEQ ID NO: 72)
DIQMTQSPS SLSASVGDRV TITC<u>RASQSV SSAVA</u>WYQQK PGKAPKLLIY <u>SASSLYS</u>GVP
SRFSGSRSGT DFTLTISSLQ PEDFATYYCQ <u>QGYAGSWHPI</u>TFG QGTKVEIK

CDCP1-010 V_H
(SEQ ID NO: 73)
EVQLVES GGGLVQPGGS LRLSCAASGF N<u>IYSYSM</u>HWV RQAPGKGLEW VA<u>SISPYYSY</u>
<u>TS</u>YADSVKGR FTISADTSKN TAYLQMNSLR AEDTAVYYCA R<u>AYYAL</u>DYWG QGTLVTVSS

TABLE A-2-continued

Sequences of Variable Regions of Anti-CDCP1 Fabs^
Fab Variable Region

CDCP1-010 V_L
(SEQ ID NO: 74)
DIQMTQSPS SLSASVGDRV TITC<u>RASQSV SSAVA</u>WYQQK PGKAPKLLIY <u>SASSLYS</u>GVP
SRFSGSRSGT DFTLTISSLQ PEDFATYYCQ Q<u>SYWYYPI</u>TFG QGTKVEIK

CDCP1-011 V_H
(SEQ ID NO: 75)
EVQLVES GGGLVQPGGS LRLSCAASGF N<u>ISYYYMH</u>WV RQAPGKGLEW VA<u>SIYSSSSY
TSY</u>ADSVKGR FTISADTSKN TAYLQMNSLR AEDTAVYYCA R<u>SYYAM</u>DYWG QGTLVTVSS

CDCP1-011 V_L
(SEQ ID NO: 76)
DIQMTQSPS SLSASVGDRV TITC<u>RASQSV SSAVA</u>WYQQK PGKAPKLLIY <u>SASSLYS</u>GVP
SRFSGSRSGT DFTLTISSLQ PEDFATYYCQ Q<u>SYYVYPI</u>TFG QGTKVEIK

CDCP1-001 V_H
(SEQ ID NO: 77)
EVQLVES GGGLVQPGGS LRLSCAASGF N<u>FSSSSIH</u>WV RQAPGKGLEW VA<u>SISSSYGY
TYY</u>ADSVKGR FTISADTSKN TAYLQMNSLR AEDTAVYYCA R<u>TVRGSKKPY FSGWAM</u>DYWG
QGTLVTVSS

CDCP1-001 V_L
(SEQ ID NO: 78)
DIQMTQSPS SLSASVGDRV TITC<u>RASQSV SSAVA</u>WYQQK PGKAPKLLIY <u>SASSLYS</u>GVP
SRFSGSRSGT DFTLTISSLQ PEDFATYYCQ Q<u>SSYSLI</u>TFG QGTKVEIK

^CDR sequences are underlined

Similarly, the combination of any 4 VH FR regions with VH CDRs1-3 from Table A-1, in proper order, would make up a VH chain for an anti-CDCP1 antibody or antibody fragment that is within the scope of the present disclosure. Furthermore, the combination of any 4 VL FRs1, VL CDR1 (SEQ ID NO:11), CDR2 (SEQ ID NO:13) and VL CDR3 from Table A-1, in proper order, make up the VL chain for an anti-CDCP1 antibody or antibody fragment that is within the scope of the present disclosure. Accordingly, the disclosure provides humanized antibodies or antibody fragments. For example, humanized antibodies or antibody fragments may be generated by inserting CDRs generated in animals into framework regions from other human antibodies or antibody fragments. Thus, the framework regions of the antibody or antibody fragments need not be the identical amino acid sequences of the framework regions of the CDCP1-001 antibody.

In certain embodiments, an antibody or antibody fragment provided herein comprises:
the VH amino acid sequence shown in SEQ ID NO:57, and the VL amino acid sequence shown in SEQ ID NO:58;
the VH amino acid sequence shown in SEQ ID NO:59, and the VL amino acid sequence shown in SEQ ID NO:60;
the VH amino acid sequence shown in SEQ ID NO:61, and the VL amino acid sequence shown in SEQ ID NO:62;
the VH amino acid sequence shown in SEQ ID NO:63, and the VL amino acid sequence shown in SEQ ID NO:64;
the VH amino acid sequence shown in SEQ ID NO:65, and the VL amino acid sequence shown in SEQ ID NO:66;
the VH amino acid sequence shown in SEQ ID NO:67, and the VL amino acid sequence shown in SEQ ID NO:68;
the VH amino acid sequence shown in SEQ ID NO:69, and the VL amino acid sequence shown in SEQ ID NO:70;
the VH amino acid sequence shown in SEQ ID NO:71, and the VL amino acid sequence shown in SEQ ID NO:72;
the VH amino acid sequence shown in SEQ ID NO:73, and the VL amino acid sequence shown in SEQ ID NO:74;
the VH amino acid sequence shown in SEQ ID NO:75, and the VL amino acid sequence shown in SEQ ID NO:76; or
the VH amino acid sequence shown in SEQ ID NO:77, and the VL amino acid sequence shown in SEQ ID NO:78.

In certain embodiments, an antibody or antibody fragment provided herein comprises the VH CDR1, CDR2, and CDR3 amino acid sequences shown in SEQ ID NO:1 above, combined with the VL CDR1, CDR2 and CDR3 sequences shown in SEQ ID NO:9 above. Optionally, the VL CDR3 shown in SEQ ID NO:9 may be substituted with one of the VL CDR3 sequences shown in Table A-1. Thus, in specific embodiments, provided herein are antibodies or antibody fragments that comprise:
VH CDR1, CDR2 and CDR3 comprising the amino acid sequence of SEQ ID NO:3, SEQ ID NO:5 and SEQ ID NO:7, and VL CDR1, CDR2 and CDR3 comprising the amino acid sequence of SEQ ID NO:11, SEQ ID NO:13 and SEQ ID NO:15;
VH CDR1, CDR2 and CDR3 comprising the amino acid sequence of SEQ ID NO:17, SEQ ID NO:18 and SEQ ID NO:19, and VL CDR1, CDR2 and CDR3 comprising the amino acid sequence of SEQ ID NO:11, SEQ ID NO:13 and SEQ ID NO:20;
VH CDR1, CDR2 and CDR3 comprising the amino acid sequence of SEQ ID NO:21, SEQ ID NO:22 and SEQ ID NO:23, and VL CDR1, CDR2 and CDR3 comprising the amino acid sequence of SEQ ID NO:11, SEQ ID NO:13 and SEQ ID NO:24;
VH CDR1, CDR2 and CDR3 comprising the amino acid sequence of SEQ ID NO:25, SEQ ID NO:26 and SEQ ID NO:27, and VL CDR1, CDR2 and CDR3 comprising the amino acid sequence of SEQ ID NO:11, SEQ ID NO:13 and SEQ ID NO:28;
VH CDR1, CDR2 and CDR3 comprising the amino acid sequence of SEQ ID NO 29, SEQ ID NO:30 and SEQ ID NO:31, and VL CDR1, CDR2 and CDR3 comprising the amino acid sequence of SEQ ID NO:11, SEQ ID NO:13 and SEQ ID NO:32;

VH CDR1, CDR2 and CDR3 comprising the amino acid sequence of SEQ ID NO:33, SEQ ID NO:34 and SEQ ID NO:35, and VL CDR1, CDR2 and CDR3 comprising the amino acid sequence of SEQ ID NO:11, SEQ ID NO:13 and SEQ ID NO:36;

VH CDR1, CDR2 and CDR3 comprising the amino acid sequence of SEQ ID NO:37, SEQ ID NO:38 and SEQ ID NO:39, and VL CDR1, CDR2 and CDR3 comprising the amino acid sequence of SEQ ID NO:11, SEQ ID NO:13 and SEQ ID NO:40;

VH CDR1, CDR2 and CDR3 comprising the amino acid sequence of SEQ ID NO:41, SEQ ID NO:42 and SEQ ID NO:43, and VL CDR1, CDR2 and CDR3 comprising the amino acid sequence of SEQ ID NO:11, SEQ ID NO:13 and SEQ ID NO:44;

VH CDR1, CDR2 and CDR3 comprising the amino acid sequence of SEQ ID NO:45, SEQ ID NO:46 and SEQ ID NO:47, and VL CDR1, CDR2 and CDR3 comprising the amino acid sequence of SEQ ID NO:11, SEQ ID NO:13 and SEQ ID NO:48;

VH CDR1, CDR2 and CDR3 comprising the amino acid sequence of SEQ ID NO:49, SEQ ID NO:50 and SEQ ID NO:51, and VL CDR1, CDR2 and CDR3 comprising the amino acid sequence of SEQ ID NO:11, SEQ ID NO:13 and SEQ ID NO:52; or VH CDR1, CDR2 and CDR3 comprising the amino acid sequence of SEQ ID NO:53, SEQ ID NO:54 and SEQ ID NO:55, and VL CDR1, CDR2 and CDR3 comprising the amino acid sequence of SEQ ID NO:11, SEQ ID NO:13 and SEQ ID NO:56.

In some embodiments, an antibody or antibody fragment provided herein comprises:

the VH amino acid sequence selected from the group consisting of SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, and SEQ ID NO:77; and the VL amino acid sequence selected from the group consisting of SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, and SEQ ID NO:78. For instance, an antibody or antibody fragment provided herein may comprise the VH amino acid sequence of SEQ ID NO:57, and the VL amino acid sequence selected from the group consisting of SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, and SEQ ID NO:78. Similarly, an antibody or antibody fragment provided herein may comprise the VL amino acid sequence of SEQ ID NO:58, and the VH amino acid sequence selected from the group consisting of SEQ ID NO:1, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, and SEQ ID NO:77.

In other embodiments, any of the antibodies provided herein may be a part of a bispecific or multispecific antibody. The bispecific or multispecific antibody may have both, or all, binding domains specific for CDCP1 (e.g., a CUB domain of CDCP1). For instance a bispecific antibody may comprise VH and VL from any combination of two of the anti-CDCP1-specific Fab sequences shown in Table A-2. Alternatively, the bispecific or multispecific antibody may have a single binding domain specific for CDCP1 (e.g., a CUB domain of CDCP1), and one or more domains specific for a second antigen. In similar fashion, a bispecific antibody can comprise VH and VL from any other combination two of the anti-CDCP1-specific Fab sequences provided herein. The CDCP1-binding domains of the present disclosure may be contained in other antibody formats, including but not limited to monospecific Fab2, bispecific Fab2, trispecific Fab3, monovalent IgGT, bispecific diabody, trispecific triabody, scFv-Fc, minibody, etc.

In still further embodiments, the CDCP1-binding domains of the present disclosure may form part of a "T-cell engager" comprising a CD3 binding domain for a linking a T cell to a CDCP1+ cancer cell (anti-CDCP1×anti-CD3). Alternatively, the CDCP1-binding domains of the present disclosure may form part of a "NK-cell engager" comprising a NKG2D or CD16 binding domain for linking a NK cell to a CDCP1+ cancer cell (anti-CDCP1×anti-NKG2D or anti-CD16). Additionally, the CDCP1-binding domains of the present disclosure may form part of an ectodomain of a chimeric T cell receptor.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the polynucleotide and amino acid sequences disclosed herein. Because a substantially purified polypeptide of the disclosure may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein, "sequence identity" is a measure of the identity of nucleotide sequences or amino acid sequences compared to a reference nucleotide or amino acid sequence. A polypeptide having an amino acid sequence at least, for example, about 95% "sequence identity" to a reference an amino acid sequence, e.g., SEQ ID NO: 1, is understood to mean that the amino acid sequence of the polypeptide is identical to the reference sequence except that the amino acid sequence may include up to about five modifications per each 100 amino acids of the reference amino acid sequence. In other words, to obtain a peptide having at least about 95% sequence identity to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

In general, the sequences are aligned so that the highest order match is obtained. "Sequence identity" per se has an art-recognized meaning and can be calculated using well known techniques. In one embodiment of the present disclosure, the algorithm used to determine sequence identity between two or more polypeptides is BLASTP. In another embodiment of the present disclosure, the algorithm used to determine sequence identity between two or more polypeptides is FASTDB (Brutlag, Comp. App. Biosci. 6:237-245, 1990). In a FASTDB sequence alignment, the query and reference sequences are amino sequences. The result of sequence alignment is in percent sequence identity. In one embodiment, parameters that may be used in a FASTDB alignment of amino acid sequences to calculate percent sequence identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent sequence identity. For query sequences truncated at the N- or C-termini, relative to the reference sequence, the percent sequence identity is corrected by calculating the number of residues of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent sequence identity, calculated by the above FASTDB program using the specified parameters, to arrive at a final percent sequence identity score. This corrected score can be used for the purposes of determining how alignments "correspond" to each other, as well as percentage sequence identity. Residues of the reference sequence that extend past the N- or C-termini of the query sequence may be considered for the purposes of manually adjusting the percent sequence identity score. That is, residues that are not matched/aligned with the N- or C-termini of the comparison sequence may be counted when manually adjusting the percent sequence identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-terminus. The 10 unpaired residues represent 10% of the reference sequence (number of residues at the N- and C-termini not matched/total number of residues in the reference sequence) so 10% is subtracted from the percent sequence identity score calculated by the FASTDB program. If the remaining 90 residues were perfectly matched (100% alignment) the final percent sequence identity would be 90% (100% alignment–10% unmatched overhang). In another example, a 90 residue query sequence is compared with a 100 reference sequence, except that the deletions are internal deletions. In this case the percent sequence identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent sequence identity. The addition in the query occurs at the N-terminus of the query sequence and therefore, the FASTDB alignment may not show a match/alignment of the first 10 residues at the N-terminus. If the remaining 100 amino acid residues of the query sequence have 95% sequence identity to the entire length of the reference sequence, the N-terminal addition of the query would be ignored and the percent identity of the query to the reference sequence would be 95%.

As used here, the term "conservative substitution" denotes the replacement of an amino acid residue by another biologically similar residue. Conservative substitution for this purpose may be defined as set out in the tables below. Amino acids can be classified according to physical properties and contribution to secondary and tertiary protein structure as shown in Table B and Table C. A conservative substitution is recognized in the art as a substitution of one amino acid for another amino acid that has similar properties, such as a substitution of one amino acid for another amino acid in the same row of Table B or Table C. Exemplary conservative substitutions are set out below in Table D.

TABLE B

Amino Acid Classification - 5 Groups

| Side Chain Characteristic | Amino Acid |
|---|---|
| Aliphatic | |
| Non-polar | Gly, Ala, Pro, Iso, Leu, Val |
| Polar-uncharged | Cys, Ser, Thr, Met, Asn, Gln |
| Polar-charged | Asp, Glu, Lys, Arg |
| Aromatic | His, Phe, Trp, Tyr |
| Other | Asn, Gln, Asp, Glu |

TABLE C

Amino Acid Classification - 10 Groups

| Side Chain Characteristic | Amino Acid |
|---|---|
| Non-polar (hydrophobic) | |
| Aliphatic: | Ala, Leu, Iso, Val, Pro |
| Aromatic: | Phe, Trp |
| Sulfur-containing: | Met |
| Borderline: | Gly |
| Uncharged-polar | |
| Hydroxyl: | Ser, Thr, Tyr |
| Amides: | Asn, Gln |
| Sulfhydryl: | Cys |
| Borderline: | Gly |
| Positively Charged (Basic): | Lys, Arg, His |
| Negatively Charged (Acidic): | Asp, Glu |

TABLE D

Conservative Amino Acid Substitutions

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |

TABLE D-continued

Conservative Amino Acid Substitutions

| Original Residue | Exemplary Substitution |
|---|---|
| Trp (W) | Tyr |
| Tyr (Y) | Trp, Phe, Thr, Ser |
| Val (V) | Ile, Leu, Met, Phe, Ala |

In select embodiments, the disclosure is directed to antibodies or antibody fragments where the amino acid sequence of one or more framework regions is mutated. In one specific embodiment, the mutations in the one or more framework regions is a conserved substitution. In more specific embodiments, the antibodies or antibody fragments of the present disclosure comprise an amino acid sequence having at least 80%, 85%, 90%, 95%, 96%, 97%, 98%, 99% or 100% sequence identity to any one of the amino acid sequences of SEQ ID NO:2, SEQ ID NO:4, SEQ ID NO:6, SEQ ID NO:8, SEQ ID NO:10, SEQ ID NO:12, SEQ ID NO:14, and SEQ ID NO:16.

Likewise, in some embodiments, the disclosure is directed to antibodies or antibody fragments that have a high level of identity to the VH and VL amino acid sequences of any one of exemplary antibodies CDCP1-001 to CDCP1-011. In specific embodiments, the antibodies or antibody fragments of the present disclosure comprise an amino acid sequence having at least 90%, 95%, 96%, 97%, 98%, or 99% sequence identity to any one of the amino acid sequences of SEQ ID NOs:57-78.

2. Antibody Conjugates

The disclosure also provides for antibodies or antibody fragments that are conjugated to one or more labels or cytotoxic agents. In one specific embodiment, the disclosure provides antibody-drug conjugates (ADCs). As used herein, an ADC need not be composed of an entire, intact antibody and instead can be composed of any one of the antibody fragments disclosed herein. ADCs are well known in the art and typically include an antibody or antibody fragment, cytotoxic agent and a linker molecule that links the antibody or antibody fragment and the cytotoxic agent. In general, the linker is designed to be susceptible to intracellular enzymes that break down the linker to release the cytotoxic agent from the antibody or antibody fragment.

As used herein, a cytotoxic agent is a compound that, depending on the dosage required, generally interferes with or inhibits cell growth, or kills cells to which the cytotoxic agent is administered. Cytotoxic agents may or may not be approved for use in humans at certain dosages. For example, some ADCs comprise compounds that are typically too toxic for human administration, but the ADCs herein can include approved agents as well. Examples of classes of compounds that may be used as cytotoxic agents in the ADCs of the present disclosure include but are not limited to kinase inhibitors, cytoskeletal disruptors, anthracyclines such as daunomycin or doxorubicin, epothilones, Type I topoisomerase inhibitors, Type II topoisomerase inhibitors, histone deacetylase inhibitors, nucleotide analogs and precursor analogs, alkylating agents, platinum-based agents, Vinca alkaloids and derivatives, calicheamycins, and retinoids. Other examples of cytotoxic agents to which the antibody or antibody fragment may be linked include but are not limited to, monomethyl auristatin F (MMAF), monomethyl auristatin E (MMAE), duocarmycin, maytansinoids, methotrexate, vindesine, a taxane such as docetaxel, paclitaxel, larotaxel, tesetaxel, or ortataxel, a dolastatin or a trichothecene. Other examples of agents to which the antibody or antibody fragment may be linked include those listed in Vater and Goldmacher, (2010) Antibody-Cytotoxic Compound Conjugates for Oncology in: Reddy and Couvreur (eds.) Macromolecular Anticancer Therapeutics. Macromolecular Anticancer Therapeutics, Springer, New York, N.Y.

In certain embodiments, any of the anti-CDCP1 antibodies or antibody fragments thereof provided herein are labeled such that the antibodies or antibody fragments can be detected, e.g., once bound to CDCP1. The labels may be conjugated directed to the antibody or antibody fragment, or the label may be attached to the antibody or antibody fragment via a linker moiety. Labels for antibodies are well known in the art and include but are not limited to biotin, fluorescent dyes, fluorescent proteins and enzymes. Labels include, but are not limited to, directly detected labels (e.g., fluorescent, chromophoric, electron-dense, chemiluminescent, and radioactive labels), as well as labels such as enzymes or ligands that are indirectly detected, e.g., through an enzymatic reaction or molecular interaction. Exemplary labels include, but are not limited to, radioisotopes such as $^{32}P$, $^{14}C$, $^{125}I$, $^{3}H$, and $^{131}I$, positron emitters, e.g., $^{68}Ga$, $^{18}F$, $^{64}Cu$, $^{86}Y$, $^{76}Br$, $^{89}Zr$, and $^{124}I$, fluorophores such as rare earth chelates or fluorescein and its derivatives, rhodamine and its derivatives, dansyl, umbelliferone, luceriferases, e.g., firefly luciferase or bacterial luciferase, luciferin, 2,3-dihydrophthalazinediones, horseradish peroxidase, alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, in combination with an enzyme that employs hydrogen peroxide to oxidize a dye precursor such as horseradish peroxidase, lactoperoxidase, or microperoxidase, biotin/avidin, spin labels, bacteriophage labels, stable free radicals, and similar molecules.

3. Polynucleotides

Also provided herein are polynucleotides that encode the antibodies or antibody fragments disclosed herein, e.g., encode any of the heavy or light chains described herein. The nucleic acids of the disclosure can be DNA or RNA, for example, mRNA. The nucleic acid molecules can be double-stranded or single-stranded; single stranded RNA or DNA can be the coding, or sense, strand or the non-coding, or antisense, strand. In particular, the nucleic acids may encode any of the antibodies or antibody fragments disclosed herein, as well as variants thereof. Of course, the nucleic acids of the present disclosure may encode additional elements, such as his tags and the like. For example, the nucleic acids of the disclosure would include those that encode any of the antibodies or antibody fragments and variants thereof that are also contain a glutathione-S-transferase fusion protein, poly-histidine (e.g., His6), poly-HN, poly-lysine, etc. If desired, the nucleotide sequences can include additional non-coding sequences such as non-coding 3' and 5' sequences (including regulatory sequences, for example).

In another specific embodiment, the disclosure provides nucleic acids that are hybridizable to a nucleic acid encoding antibodies or antibody fragments of the present disclosure. Various other stringency conditions that promote nucleic acid hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M NaHPO$_4$ (pH 7.2)/1 mM EDTA/7% SDS, or hybridization in 50% formamide/0.25M NaHPO$_4$ (pH 7.2)/0.25 M NaCl/1 mM EDTA/7% SDS; followed by washing in 40 mM NaHPO$_4$ (pH 7.2)/1 mM EDTA/5% SDS at 42° C. or in 40 mM NaHPO$_4$ (pH 7.2)/1 mM EDTA/1% SDS at 50° C. Both temperature and salt may be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., 1989, Molecular Cloning, A Laboratory Manual, Second Edition, Cold Spring Harbor Press, N.Y and Ausubel et al., 1989, Current Protocols in Molecular Biology, Green Publishing Associates and Wiley Interscience, New York.

Nucleic acids encoding antibodies or antibody fragments of the present disclosure may be produced by methods well known in the art. In one aspect, nucleic acids encoding the antibodies or antibody fragments can be derived from antibodies or antibody fragments coding sequences by recombinant DNA methods known in the art. Various methods may be used, including but not limited to, oligonucleotide directed, site specific mutagenesis. This and other techniques known in the art may be used to create single or multiple mutations, such as replacements, insertions, deletions, and transpositions.

In one embodiment, the nucleic acids encoding the antibodies or antibody fragments are synthetic nucleic acids in which the codons have been optimized for increased expression in the host cell in which it is produced. The degeneracy of the genetic code permits variations of the nucleotide sequence, while still producing a polypeptide having the identical amino acid sequence as the polypeptide encoded by the native DNA sequence. The frequency of individual synonymous codons for amino acids varies widely from genome to genome among eukaryotes and prokaryotes. These differences in codon choice patterns appear to contribute to the overall expression levels of individual genes by modulating peptide elongation rates. For this reason, it may be desirable and useful to design nucleic acid molecules intended for a particular expression system where the codon frequencies reflect the tRNA frequencies of the host cell or organism in which the protein is expressed. Native codons are exchanged for codons of highly expressed genes in the host cells. For instance, the nucleic acid molecule can be optimized for expression of the encoded protein in bacterial cells (e.g., *E. coli*), yeast (e.g., *Pichia*), insect cells (e.g., *Drosophila*), or mammalian cells or animals (e.g., human, sheep, bovine or mouse cells or animals).

Restriction enzyme sites critical for gene synthesis and DNA manipulation are preserved or destroyed to facilitate nucleic acid and vector construction and expression of the encoded protein. In constructing the synthetic genes of the disclosure it may be desirable to avoid CpG sequences as these sequences may cause gene silencing. The codon optimized sequence can be synthesized and assembled and inserted into an appropriate expression vector using conventional techniques well known to those of skill in the art.

In one particular embodiment, a synthetic nucleic acid encoding antibodies or antibody fragments of the present disclosure comprises at least one codon substitution in which non-preferred or less preferred codon in the natural gene encoding the protein has been replaced by a preferred codon encoding the same amino acid. For instance, in humans the preferred codons are: Ala (GCC); Arg (CGC); Asn (AAC); Asp (GAC); Cys (TGC); Gln (CAG); Gly (GGC); His (CAC); Ile (ATC); Leu (CTG); Lys (AAG); Pro(CCC); Phe (TTC); Ser (AGC); Thr (ACC); Tyr (TAC); and Val (GTG). Less preferred codons are: Gly (GGG); Ile (ATT); Leu (CTC); Ser (TCC); Val (GTC); and Arg (AGG). In general, the degree of preference of a particular codon is indicated by the prevalence of the codon in highly expressed genes. Replacing a codon with another codon that is more prevalent in highly expressed human genes will generally increase expression of the gene in mammalian cells. Accordingly, the disclosure includes replacing a less preferred codon with a preferred codon as well as replacing a non-preferred codon with a preferred or less preferred codon.

Further, nucleic acids containing the antibodies or antibody fragments coding sequences may be truncated by restriction enzyme or exonuclease digestions. Heterologous coding sequences may be added to the antibodies or antibody fragments coding sequences by ligation or PCR amplification. Moreover, DNA encoding the whole or a part of the antibodies or antibody fragments of the present disclosure may be synthesized chemically or using PCR amplification based on the known or deduced amino acid sequence of the antibodies or antibody fragments and any desired alterations to that sequence.

The identified and isolated DNA encoding the antibodies or antibody fragments of the present disclosure can be inserted into an appropriate cloning vector. A large number of vector-host systems known in the art may be used. The term "host" or "host cell" as used herein refers to either in vivo in an animal or in vitro in mammalian cell cultures.

The present disclosure also comprises vectors containing the nucleic acids encoding the antibodies or antibody fragments of the present disclosure. As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Examples of vectors include but are not limited to those capable of autonomous replication and expression of the structural gene products present in the DNA segments to which they are operably joined.

In certain respects, the vectors to be used are those for expression of polynucleotides and proteins of the present disclosure. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express the proteins of the disclosure. Such vectors include chromosomal, episomal and virus-derived vectors, e.g., vectors derived from bacterial plasmids, from bacteriophage, from yeast episomes, from yeast chromosomal elements, from viruses such as adeno-associated virus, lentivirus, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the present disclosure. Generally, any vector suitable to maintain, propagate or the fusion proteins in a host may be used for expression in this regard.

The DNA sequence in the expression vector is generally operably linked to appropriate expression control sequence(s) including, for instance, a promoter to direct mRNA transcription. Representatives of such promoters include, but are not limited to, the phage lambda PL promoter, the *E. coli* lac, trp and tac promoters, HIV promoters, the SV40 early and late promoters and promoters of retroviral LTRs, to name just a few of the well-known promoters. In general, expression constructs will contain sites for transcription, initiation and termination and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

As used herein, a coding sequence and regulatory sequences are said to be "operably joined" or "operably linked" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but in general includes, as necessary, 5' non-transcribing and 5' non-translating sequences involved with initiation of transcription and translation respectively, such as a TATA box, capping sequence, CAAT sequence, and the like. Such 5' non-transcribing regulatory sequences may include a promoter region which includes a promoter sequence for transcriptional control of the operably joined gene. Regulatory sequences may also include enhancer sequences or upstream activator sequences, as desired.

Vectors for propagation and expression generally will include selectable markers. Such markers also may be suitable for amplification or the vectors may contain additional markers for this purpose. In this regard, the expression vectors may contain one or more selectable marker genes to provide a phenotypic trait for selection of transformed host cells. Examples of markers include dihydrofolate reductase or neomycin resistance for eukaryotic cell culture, and tetracycline, kanamycin or ampicillin resistance genes for culturing *E. coli* and other bacteria.

Promoter/enhancer elements which may be used to control expression of inserted sequences include, but are not limited to the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42) for expression in animal cells, the promoters of lactamase (Villa-Kamaroff et al., 1978, Proc. Natl. Acad. Sci. U.S.A. 75:3727-3731), tac (DeBoer et al., 1983, Proc. Natl. Acad. Sci. U.S.A. 80:21-25), or trc for expression in bacterial cells (see also "Useful proteins from recombinant bacteria" in Scientific American, 1980, 242:74-94), the nopaline synthetase promoter region or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120) for expression in plant cells; Gal4 promoter, the ADC (alcohol dehydrogenase) promoter, PGK (phosphoglycerol kinase) promoter, alkaline phosphatase promoter for expression in yeast or other fungi.

Depending on the host-vector system utilized, any one of a number of suitable transcription and translation elements may be used. In one embodiment, a fusion protein comprising an antibody or antibody fragment of the present disclosure and a pre and/or pro sequence of the host cell is expressed. In other embodiments, a fusion protein comprising an antibody or antibody fragment of the present disclosure fused with, for example, an affinity purification peptide, including but not limited to, maltose binding protein, glutathione-S-transferase, thioredoxin or histidine tag, is expressed. In additional embodiments, a chimeric protein comprising an antibody or antibody fragment of the present disclosure and a useful immunogenic peptide or protein is expressed.

Any method known in the art for inserting DNA fragments into a vector may be used to construct expression vectors containing an antibody or antibody fragment encoding nucleic acid molecule comprising appropriate transcriptional/translational control signals and the polypeptide coding sequences. These methods may include in vitro recombinant DNA and synthetic techniques and in vivo recombination.

Methods of introducing exogenous DNA into yeast hosts include either the transformation of spheroplasts or of intact yeast cells treated with alkali cations. Transformation procedures usually vary with the yeast species to be transformed. See, e.g., Kurtz et al. (1986) Mol. Cell. Biol. 6:142; Kunze et al. (1985) J. Basic Microbiol. 25:141; for *Candida*, Gleeson et al. (1986) J. Gen. Microbiol. 132:3459; Roggenkamp et al. (1986) Mol. Gen. Genet. 202:302; for *Hansenula*; Das et al. (1984) J. Bacteriol. 158:1165; De Louvencourt et al. (1983) J. Bacteriol. 154:1165; Van den Berg et al. (1990) Bio/Technology 8:135; for *Kluyveromyces*; Cregg et al. (1985) Mol. Cell. Biol. 5:3376; Kunze et al. (1985) J. Basic Microbiol. 25:141; U.S. Pat. Nos. 4,837,148 and 4,929,555; for *Pichia*; Hinnen et al. (1978) Proc. Natl. Acad. Sci. USA 75; 1929; Ito et al. (1983) J. Bacteriol. 153:163; for *Saccharomyces*; Beach et al. (1981) Nature 300:706; for *Schizosaccharomyces*; Davidow et al. (1985) Curr. Genet. 10:39.

Commercially available vectors for expressing heterologous proteins in bacterial hosts include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx. For example, the phage in lambda GEM™-11 may be utilized in making recombinant phage vectors which can be used to transform host cells, such as *E. coli* LE392. In a one embodiment, the vector is pQE30 or pBAD/ThioE, which can be used transform host cells, such as *E. coli*.

Expression and transformation vectors for transformation into many yeast strains are available. For example, expression vectors have been developed for, the following yeasts: *Candida albicans*, Kurtz, et al. (1986) Mol. Cell. Biol. 6:142; *Candida maltosa*, Kunze, et al. (1985) J. Basic Microbiol. 25:141; *Hansenula polymorpha*, Gleeson, et al. (1986) J. Gen. Microbiol. 132:3459; Roggenkamp et al. (1986) Mol. Gen. Genet. 202:302; *Kluyveromyces fragilis*, Das, et al. (1984) J. Bacteriol. 158:1165; *Kluyveromyces lactis*, De Louvencourt et al. (1983) J. Bacteriol. 154:737; Van den Berg, et al. (1990) Bio/Technology 8:135; *Pichia quillerimondii*, Kunze et al. (1985) J. Basic Microbiol. 25:141; *Pichia pastoris*, Cregg, et al. (1985) Mol. Cell. Biol. 5:3376, U.S. Pat. Nos. 4,837,148 and 4,929,555; *Saccharomyces cerevisiae*, Hinnen et al. (1978) Proc. Natl. Acad. Sci. USA 75:1929, Ito et al. (1983) J. Bacteriol. 153:163; *Schizosaccharomyces pombe*, Beach et al. (1981) Nature 300: 706; and *Yarrowia lipolytica*, Davidow, et al. (1985) Curr. Genet. 10:380-471, Gaillardin, et al. (1985) Curr. Genet. 10:49.

4. Host Cells

Further provided are host cells comprising the nucleic acids and vectors described herein. A variety of host-vector systems may be utilized to express the polypeptide-coding sequence. These include but are not limited to mammalian cells, mammalian cell systems infected with virus (e.g., vaccinia virus, adenovirus, etc.); insect cells, insect cell systems infected with virus (e.g., baculovirus); microorganisms such as yeast containing yeast vectors, or bacteria transformed with bacteriophage DNA, plasmid DNA, or cosmid DNA, plant cells or transgenic plants.

Hosts that are appropriate for expression of nucleic acid molecules of the present disclosure, fragments, analogues or variants thereof, may include *E. coli*, *Bacillus species*, *Haemophilus*, fungi, yeast, such as *Saccharomyces, Pichia, Bordetella*, or *Candida*, or the baculovirus expression system.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered antibodies or antibody fragments may be controlled. Furthermore, different host cells have characteristic and specific mechanisms for the translational and post-translational processing and modification of proteins. Appropriate cell lines or host systems can be chosen to ensure the desired modification and processing of the foreign protein expressed.

Once a suitable host system and growth conditions are established, recombinant expression vectors can be propagated and prepared in quantity. Upon expression, a recombinant polypeptide of the disclosure is produced and can be recovered in a substantially purified from the cell paste, the cell extract or from the supernatant after centrifugation of the recombinant cell culture using techniques well known in the art.

For instance, the recombinant polypeptide can be purified by antibody-based affinity purification, preparative gel electrophoresis, or affinity purification using tags (e.g., 6× histidine tag) included in the recombinant polypeptide.

Also provided herein are methods of producing any of the antibodies or antibody fragments disclosed and provided herein, with the method comprising culturing a host cell harboring a vector encoding the antibodies or antibody fragments in culture conditions in which expression of the antibodies or antibody fragments from the vector occurs in the host, and purifying the antibodies or antibody fragments from the cell culture. In certain embodiments, the method comprises culturing a host cell harboring a vector encoding the antibodies or antibody fragments in culture conditions in which expression of the antibodies or antibody fragments from the vector occurs in the host, and purifying the antibodies or antibody fragments from the cell culture.

In one embodiment, the methods comprise culture conditions in which expression of the antibodies or antibody fragments from the vector comprise culturing the host cell at a temperature below 37° C. In another embodiment, the methods also comprise culture conditions in which expression of the antibodies or antibody fragments from the vector comprise culturing the host cell for at least 8 hours. In another embodiment, the methods also comprise culture conditions in which expression of the antibodies or antibody fragments from the vector comprise culturing the host in a medium comprising an enzymatic digest of casein. In another embodiment, the methods also comprise purifying the antibodies or antibody fragments from the cell culture comprises lysing the host cells in the presence of at least two ionic detergents.

As used herein with respect to polypeptides and polynucleotides, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated polynucleotide is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a polynucleotide sequence existing in its native state in its natural host is not. An isolated polypeptide and polynucleotide may be substantially purified, but need not be. For example, a polynucleotide that is isolated within a cloning or expression vector is not pure in that it may comprise only a tiny percentage of the material in the cell in which it resides. Such a polynucleotide is isolated, however, as the term is used herein because it is readily manipulable by standard techniques known to those of ordinary skill in the art.

5. Pharmaceutical Compositions

Further provided are pharmaceutical compositions comprising the antibodies or antibody fragments described. The pharmaceutical compositions comprise at least one antibody or antibody fragment of the present disclosure and a pharmaceutical carrier. The pharmaceutical compositions may be administered, or may be formulated to be administered, by any medically-acceptable route of administration, for example, administration intravenously, intra-arterially, intradermally, intramuscularly, intraperitoneally, subcutaneously, epidurally, sublingually, intracerebrally, intravaginally, intrathecally, or transdermally.

The present compositions will contain a therapeutically effective amount the antibodies or antibody fragments, together with a suitable amount of a pharmaceutically acceptable vehicle so as to provide the form for proper administration to a patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the disclosure is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the disclosure and pharmaceutically acceptable vehicles should be sterile. Water is one example of a vehicle when the compound of the disclosure is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The pharmaceutical compositions may further contain one or more auxiliary substance, such as wetting or emulsifying agents, pH buffering agents, or adjuvants to enhance the effectiveness thereof.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use.

In another embodiment, the compounds and/or compositions of the disclosure are formulated in accordance with routine procedures as a pharmaceutical composition adapted for intravenous administration to mammals, including humans. Typically, compounds and/or compositions of the disclosure for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the disclosure is to be administered by infusion, it can be dispensed, for example, with an infusion bottle containing sterile pharmaceutical grade water or saline. Where the compound of the disclosure is administered by injection, an ampoule of sterile water for injection or saline can be provided so that the ingredients may be mixed prior to administration.

The amount of a compound of the disclosure that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. In specific embodiments of the disclosure, the oral dose of at least one compound of the present disclosure is about 0.01 milligram to about 100 milligrams per kilogram body weight, or from about 0.1 milligram to about 50 milligrams per kilogram body weight, or from about 0.5 milligram to about 20 milligrams per kilogram body weight, or from about 1 milligram to about 10 milligrams per kilogram body weight.

Suitable dosage ranges for parenteral, for example, intravenous (IV) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the disclosure per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the disclosure for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

In other embodiments, a composition of the disclosure for parenteral, for example, intravenous administration includes about 0.001 milligram to about 2000 milligrams of a compound of the disclosure, from about 0.01 milligram to about 1000 milligrams of a compound of the disclosure, from about 0.1 milligram to about 500 milligrams of a compound of the disclosure, or from about 1 milligram to about 200 milligrams of a compound of the disclosure.

The disclosure also provides pharmaceutical packs or kits comprising one or more containers filled with one or more the antibodies or antibody fragments of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the disclosure.

A therapeutically effective amount of the antibodies or antibody fragments in the composition should be administered, in which "a therapeutically effective amount" is defined as an amount that is sufficient to produce a desired prophylactic, therapeutic or ameliorative response in a subject. The amount needed will vary depending upon the antibodies or antibody fragments used and the species and weight of the subject to be administered, but may be ascertained using standard techniques.

6. Methods of Treatment

Further provided herein are methods of suppressing or inhibiting the growth of, or reducing the growth rate of, abnormal cells, e.g., abnormal cells that express CDCP1, comprising contacting the cells with, or administering to the cells, a pharmaceutically effective amount of a composition comprising at least one of the anti-CDCP1 antibodies or antibody fragments of the present disclosure.

In certain embodiments, the abnormal cells are cancer cells, such as lung cancer cells, breast cancer cells, colon cancer cells, melanoma cells, e.g., malignant melanoma cells, ovarian carcinoma cells, brain tumor cells, e.g., glioblastoma multiforme cells, soft tissue sarcoma cells, rhabdomyosarcoma cells, pancreatic cancer cells, prostate cancer cells, or osteosarcoma cells. In certain specific embodiments, the abnormal cells are cells of a cancer that harbors a KRAS mutation, such as but not limited to lung and colorectal cancer cells. Cancer cells on which the methods of the present disclosure may be applied for inhibiting the growth of abnormal cells include those cancers of epithelial tissue origin that harbor a KRAS mutation and/or express the CDCP1 protein. In specific embodiments, the cells to which the antibodies or antibody fragments are administered include but are not limited to breast cancer cells comprising a KRAS mutation and/or expressing the CDCP1 protein, colon cancer cells comprising a KRAS mutation and/or expressing the CDCP1 protein, malignant melanoma cells comprising a KRAS mutation and/or expressing the CDCP1 protein, ovarian carcinoma cells comprising a KRAS mutation and/or expressing the CDCP1 protein, brain tumor cells comprising a KRAS mutation and/or expressing the CDCP1 protein, soft tissue sarcoma cells comprising a KRAS mutation and/or expressing the CDCP1 protein, rhabdomyosarcoma cells comprising a KRAS mutation and/or expressing the CDCP1 protein, pancreatic cancer cells comprising a KRAS mutation and/or expressing the CDCP1 protein, prostate cancer cells comprising a KRAS mutation and/or expressing the CDCP1 protein or osteosarcoma cells comprising a KRAS mutation and/or expressing the CDCP1 protein.

Also provided herein is a method of treating a subject having a cancer, e.g., a cancer expressing CDCP1 protein, comprising administering to the subject a therapeutically effective amount of an anti-CDCP1 antibody or antibody fragment provided herein. Further provided herein is a method of reducing the likelihood of cancer metastasis, such as lung cancer metastasis, breast cancer metastasis, colon cancer metastasis, malignant melanoma metastasis, ovarian carcinoma metastasis, brain tumor metastasis, soft tissue sarcoma metastasis, rhabdomyosarcoma metastasis, pancreatic cancer metastasis, prostate cancer metastasis and osteosarcoma metastasis, comprising administering to a subject in need of such treatment a therapeutically effective amount of a composition comprising an anti-CDCP1 antibody or antibody fragment provided herein. In certain embodiments, the cancer is lung cancer, breast cancer, colon cancer, melanoma, e.g., malignant melanoma, ovarian carcinoma, brain cancer, e.g., glioblastoma multiforme, soft tissue sarcoma, rhabdomyosarcoma, pancreatic cancer, prostate cancer, or osteosarcoma. In certain specific embodiments, the cancer comprises a KRAS mutation and/or expresses CDCP1, including but not limited to breast cancer that comprises a KRAS mutation and/or expresses CDCP1, colon cancer that comprises a KRAS mutation and/or expresses CDCP1, melanoma, e.g., malignant melanoma, that comprises a KRAS mutation and/or expresses CDCP1, ovarian carcinoma that comprises a KRAS mutation and/or expresses CDCP1, brain cancer, e.g. glioblastoma multiforme, that comprises a KRAS mutation and/or expresses CDCP1, soft tissue sarcoma that comprises a KRAS mutation and/or expresses CDCP1, rhabdomyosarcoma that comprises a KRAS mutation and/or expresses CDCP1, pancreatic cancer that comprises a KRAS mutation and/or expresses CDCP1, prostate cancer that comprises a KRAS mutation and/or expresses CDCP1 or osteosarcoma that comprise a KRAS mutation and/or expresses CDCP1.

In other embodiments, the antibodies or antibody fragments of the disclosure are administered to a patient, for example a human, as a preventative measure against diseases, including preventing the occurrence of a tumor or preventing the progression of a tumor.

The subject is preferably a human, but can be another mammal, such a cow, horse, sheep, pig, chicken, cat, dog, mouse, rat, rabbit, guinea pig, or non-human primate. The methods of treatment or prophylaxis of the presence abnormal cells comprise administering to a subject in need of treatment thereof a pharmaceutically effective amount of a composition comprising at least one of the anti-CDCP1 antibodies or antibody fragments provided herein.

As used herein and unless otherwise indicated, the terms "cancer" or "cancer cell" refer to abnormal cell growth or proliferation that may or may not include spontaneous or induced phenotypic changes. As used herein, "cancer" includes but is not limited to such abnormal conditions as hypertrophy, neoplasia, hyperplasia, benign and malignant cancer. As used herein, the term "tumor" is a general term that includes hypertrophies, neoplasias, hyperplasias, benign cancers and malignant cancers. Accordingly, certain embodiments of the present disclosure include but are not limited to treating a hypertrophy, a neoplasia, a hyperplasia, a benign or a malignant cancer in a subject. In additional embodiments, the present disclosure is directed to preventing or reducing the likelihood of metastasis and/or recurrence of a hypertrophy, a neoplasia, a hyperplasia, a benign or a malignant cancer within a subject comprising administering at least one compound of the present disclosure to the subject. For example, at least one compound of the present disclosure may be administered after tumor resection/removal/ablation, etc. to reduce the likelihood of recurrence of the tumor in the subject. In another example, at least one compound of the present disclosure may be administered to reduce the likelihood of metastasis of the tumor in the subject.

As used herein, "treatment" or "treating" refers to an amelioration of a disease or disorder, or at least one detectable symptom thereof, or amelioration of at least one measurable physical parameter, not necessarily discernible by the patient. "Treatment" or "treating" may also refer to inhibiting the progression of a disease or disorder, either physically, e.g., stabilization of a discernible symptom, physiologically, e.g., stabilization of a physical parameter, or both, or to delaying the onset of a disease or disorder.

As used herein, the term "prevent," as it relates to tumors and/or abnormal cell growth, indicates that the antibodies or antibody fragments of the present disclosure is administered to a subject to at least partially inhibit or reduce the likelihood of growth, division, spread, or proliferation of cancer cells. Of course, the term "prevent" also encompasses prohibiting entirely the emergence of new tumors or any of the associated symptoms from detectably appearing. Thus a subject may be "pretreated," by administering the one or more the antibodies or antibody fragments of the present disclosure to prevent tumors from arising. The phrase "preventing the progression," as it relates to tumors, is used to mean a procedure designed to at least partially inhibit the detectable appearance of one or more additional tumors or aberrant cell growth in a patient already exhibiting one or more symptoms of the presence of a tumor or aberrant cell growth, and is also used to mean at least partially prohibiting the already-present symptoms of cancer from worsening in the subject.

As used herein, the term "administer" and "administering" are used to mean introducing at least one of the antibodies or antibody fragments to the cells in close enough proximity that the antibodies or antibody fragments can exert an effect on the cells. For example, "administer," in an in vivo setting refers to introducing the antibodies or antibody fragments to the subject in need of treatment or prophylactic treatment thereof. In an in vitro, e.g., cell culture, setting, the term "administer" can mean to introduce the antibodies or antibody fragments into the cell culture environment such that the antibodies or antibody fragments contact the cells. When administration is for the purpose of treatment of a subject in need of treatment thereof, the antibodies or antibody fragments can be provided at, or after the diagnosis of an abnormal cell growth, such as a tumor. The therapeutic administration of the antibodies or antibody fragments serves to inhibit cell growth of the tumor or abnormal cell growth.

As used herein, the term "coadminister" is used to mean that each of at least two compounds are administered during a time frame wherein the respective periods of biological activity overlap. Thus the term includes sequential as well as coextensive administration of the compositions of the present disclosure. If more than one substance is coadministered, the routes of administration of the two or more substances need not be the same. The scope of the disclosure is not limited by the identity of the substance which may be coadministered with the compositions of the present disclosure. For example, one of the compositions of the present disclosure may be co-administered with another compound or another other pharmaceutically active substance, such as vinca alkaloids, nucleic acid inhibitors, platinum agents, interleukin-2, interferons, alkylating agents, antimetabolites, corticosteroids, DNA intercalating agents, anthracyclines, and ureas. Examples of specific agents in addition to those exemplified herein, include hydroxyurea, 5-fluorouracil, anthramycin, asparaginase, bleomycin, dactinomycin, dacabazine, cytarabine, busulfan, thiotepa, lomustine, mechlorehamine, cyclophosphamide, melphalan, mechlorethamine, chlorambucil, carmustine, 6-thioguanine, methotrexate, etc.

7. Methods of Detection

The disclosure also provides methods detecting the presence of abnormal cells, with the method comprising administering to the cells a labeled antibody or antibody fragment of the present disclosure to allow binding of the antibody or antibody fragment, and subsequently detecting the binding of the labeled antibody or antibody fragment. Abnormal cells are marked by the overexpression of CDCP1. Methods of detecting labeled antibody or antibody fragment binding are well known in the art and include but are not limited to ELISA, FACS, immunohistochemistry and the like. The methods of detecting may be carried out in vitro, in situ or in vivo.

8. Enumerated Embodiments

1. An antibody or antibody fragment that specifically binds a CUB domain-containing protein 1 (CDCP1) ectodomain, comprising a light chain CDR1 comprising SEQ ID NO:11, a light chain CDR2 comprising SEQ ID NO:13, and
   (a) a light chain CDR3 comprising one of the group consisting of SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, and SEQ ID: 15,
   (b) a heavy chain CDR1 comprising one of the group consisting of SEQ ID NO:17, SEQ ID NO:21, SEQ ID NO:25, SEQ ID NO:29, SEQ ID NO:33, SEQ ID NO:37, SEQ ID NO:41, SEQ ID NO:45, SEQ ID NO:49, SEQ ID NO:53, and SEQ ID NO:3;
   (c) a heavy chain CDR2 comprising one of the group consisting of SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, and SEQ ID NO:5, and
   (d) a heavy chain CDR3 comprising one of the group consisting of SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51 and SEQ ID NO:55, and SEQ ID NO:7.

2. The antibody or antibody fragment of embodiment 1, comprising light chain CDRs of SEQ ID NO:11, SEQ ID NO:13 and SEQ ID NO:20, and comprising heavy chain CDRs of SEQ ID NO:17, SEQ ID NO:18, and SEQ ID NO:19.

3. The antibody or antibody fragment of embodiment 1, wherein the antibody or antibody fragment comprises at least one heavy chain variable domain (VH) and at least one light chain variable domain (VL), wherein:
   the VH comprises the amino acid sequence selected from the group consisting of SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, and SEQ ID NO:77; and
   the VL comprises the amino acid sequence selected from the group consisting of SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, and SEQ ID NO:78.

4. The antibody or antibody fragment of embodiment 3, wherein the VH comprises the amino acid sequence of SEQ ID NO:57, and the VL comprises the amino acid sequence of SEQ ID NO:58.

5. The antibody or antibody fragment of any one of embodiments 1 to 4, wherein the antibody or antibody fragment further comprises a cytotoxic agent conjugated to the antibody or antibody fragment.

6. The antibody or antibody fragment of any one of embodiments 1 to 4, wherein the antibody or antibody fragment further comprises a binding domain that specifically binds to CD3 on the surface of cytotoxic T-cells.

7. The antibody or antibody fragment of any one of embodiments 1 to 4, wherein the antibody or antibody fragment further comprises a detectable label conjugated to the antibody or antibody fragment.

8. A nucleic acid encoding the antibody or antibody fragment of any one of embodiments 1 to 7.

9. An expression vector comprising the nucleic acid of embodiment 8 in operable combination with a promoter.

10. A host cell comprising the expression vector of embodiment 9.

11. A pharmaceutical composition comprising the antibody or antibody fragment of any one of embodiments 1 to 7 and a pharmaceutically acceptable carrier.

12. Use of the antibody or antibody fragment of any one of embodiments 1 to 6 in the manufacture of a medicament for treating cancer in a subject having cancer.

13. The antibody or antibody fragment of any one of embodiments 1 to 6 for use in a method of treating cancer in a subject having cancer.

14. A method of treating cancer in a subject having cancer, the method comprising administering to the subject a therapeutically effective amount of the antibody or antibody fragment of any one of embodiments 1 to 6.

15. The use of embodiment 12 or 13, or the method of embodiment 14, wherein cancer cells of the subject comprise a RAS mutation and/or express CDCP1.

16. The use of embodiment 12 or 13, or the method of embodiment 14, wherein the RAS mutation is a G12V mutation in KRAS.

17. The use of embodiment 12 or 13, or the method of embodiment 14, wherein the cancer cells are pancreatic ductal adenocarcinoma (PDAC) cells.

18. The use of embodiment 12 or 13, or the method of embodiment 14, wherein the RAS mutation is a KRAS mutation and the cancer is selected from the group consisting of pancreatic cancer, colorectal cancer.

19. The use of embodiment 12 or 13, or the method of embodiment 14, wherein the RAS mutation is a NRAS mutation and the cancer is selected from the group consisting of acute myeloid leukemia and melanoma.

20. The use of embodiment 12 or 13, or the method of embodiment 14, wherein the RAS mutation is a HRAS mutation and the cancer is bladder cancer.

21. The antibody or antibody fragment of embodiment 7 for use in a method of detecting cancer in a subject having cancer.

22. A method of detecting cancer cells, the method comprising administering the antibody or antibody fragment of embodiment 7 to the cells, and detecting the binding of the antibody or antibody fragment to the cells.

EXAMPLES

The examples presented herein are meant for illustrative purposes and are not intended to limit the full scope of the disclosure. The attached figures are meant to be integral parts of the specification of the disclosure.

Abbreviations: ADC (antibody drug conjugate); BiTE (bispecific T-cell engager); CDCP1 (CUB domain-containing protein); CDR (complementarity determining region); ECD (extracellular domain); ELISA (enzyme-linked immunosorbent assay); Fab (antigen-binding antibody fragment); FACS (fluorescent activated cell sorting); FR (framework region); GO (gene ontology); HPAC (human pancreatic adenocarcinoma); HPNE (human pancreatic normal epithelial); MFI (mean fluorescence intensity); MMAF (monomethyl auristatin F); PDAC (pancreatic ductal adenocarcinoma cancer); SD (standard deviation); SILAC (stable isotope labeling with amino acids in cell culture); VH or $V_H$ (heavy chain variable domain); VL or $V_L$ (light chain variable domain); and WT (wild type).

Example 1: Characterization of an Oncogenic KRAS Surfaceome

To begin to isolate the effects of KRAS transformation on the cell surfaceome, a well-characterized, non-tumorigenic immortalized mammary epithelial cell line, MCF10A (Debnath et al., Methods, 30:256-268, 2003; and Martins et al., Cancer Discovery, 5:154-167, 2015), was chosen to generate an isogenic model for KRAS transformation. The diploid MCF10A cell line is often used for oncogenic transformation studies because it is non-malignant and harbors only small genetic modifications typical of a culture adapted cell line. When MCF10A cells are stably transduced with oncogenic KRASG12V they undergo numerous phenotypic changes characteristic of malignant transformation, including increased proliferation and significant loss of cell adhesion (Stolze et al., Scientific Reports, 5:8535, 2015). Recently, it has been shown that the surfaceome does indeed change substantially in MCF10A cells expressing oncogenic KRAS (Ye et al., Oncotarget, 7:86948-86971, 2016). To determine the therapeutic potential of exploiting differences in the surfaceome in RAS-driven cancers, a quantitative measurement regarding the extent to which these proteins change was undertaken.

Figure 1B:
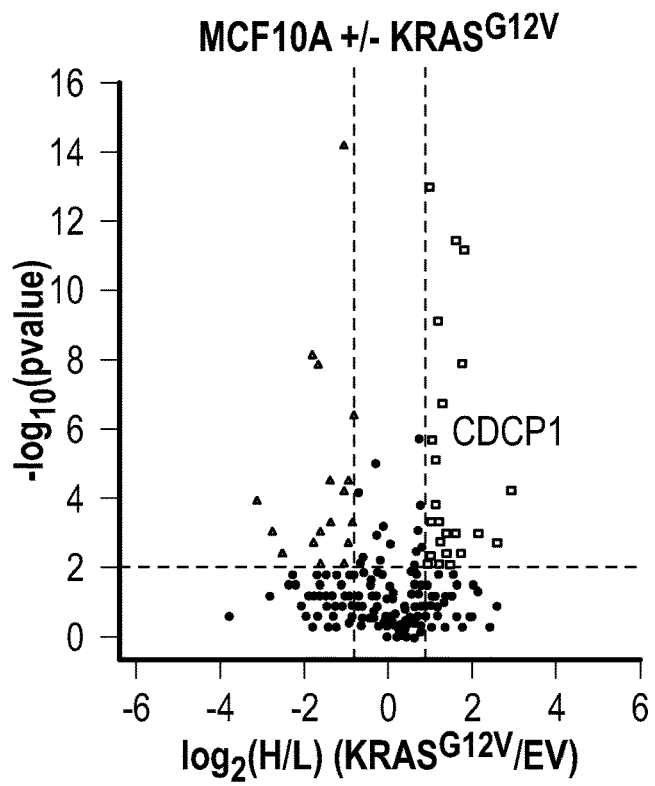
Figure 1C:
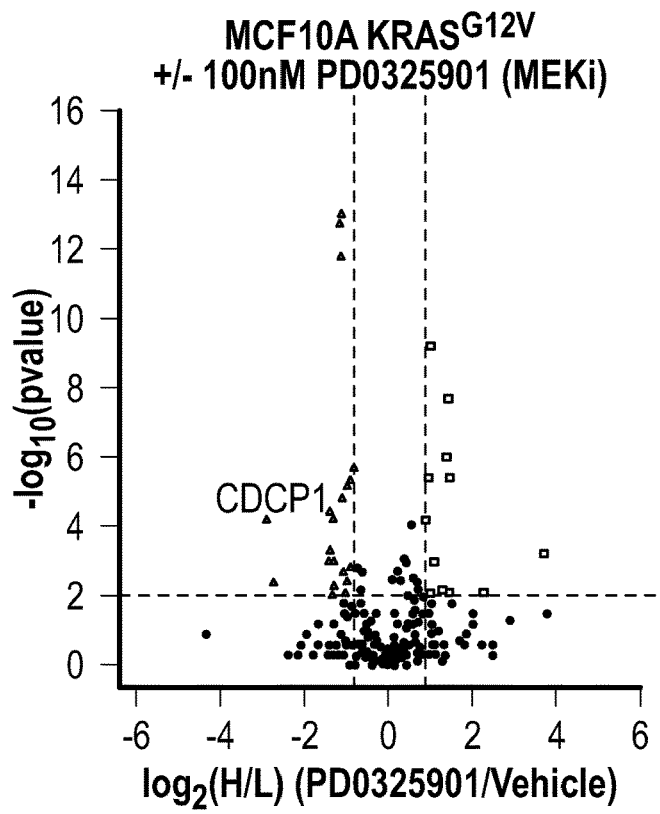
Figure 2A:
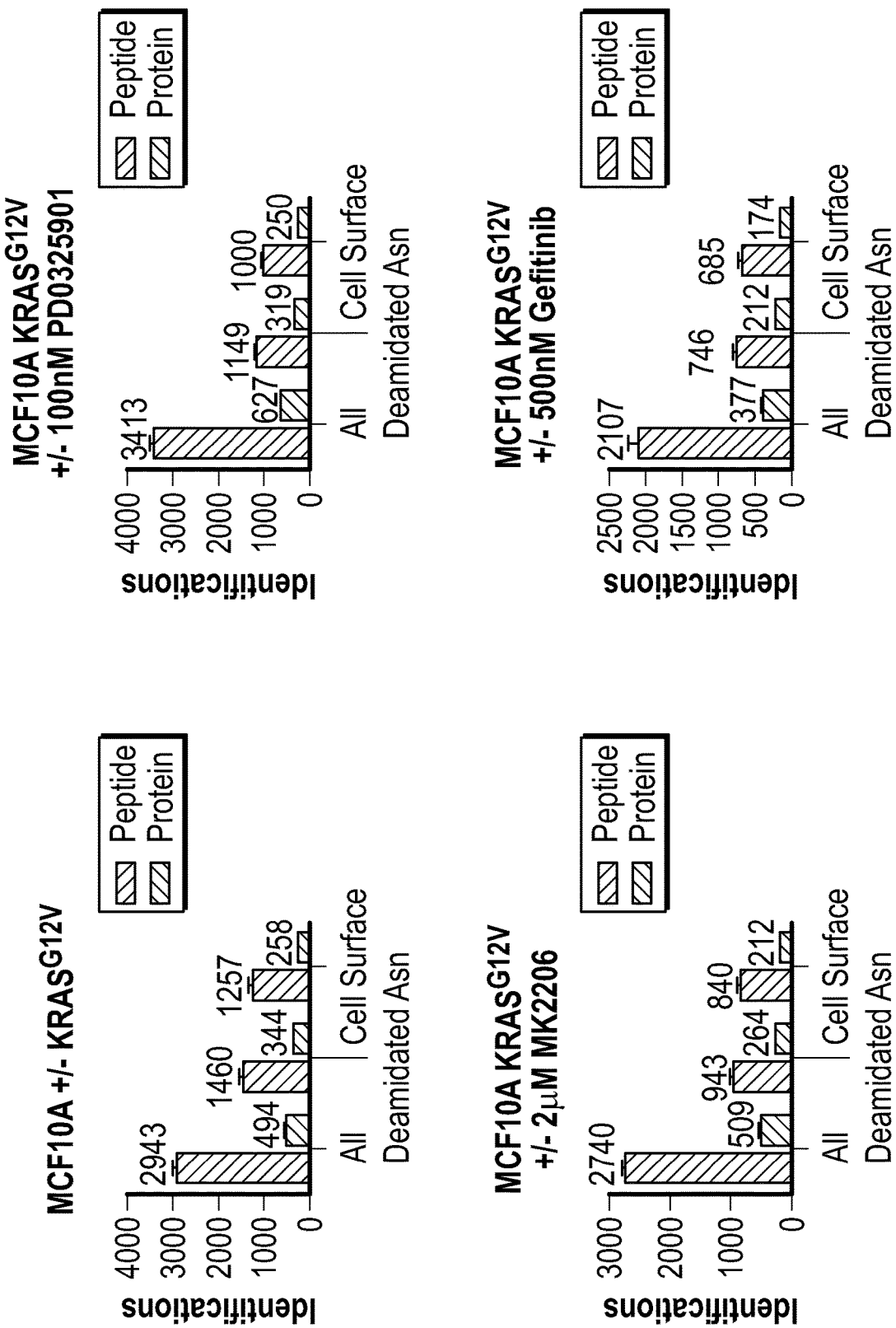
FIG. 2A-2F further illustrates that oncogenic KRAS signaling coordinately regulates the expression of cell surface proteins in a model epithelial cell.
Figure 2B:
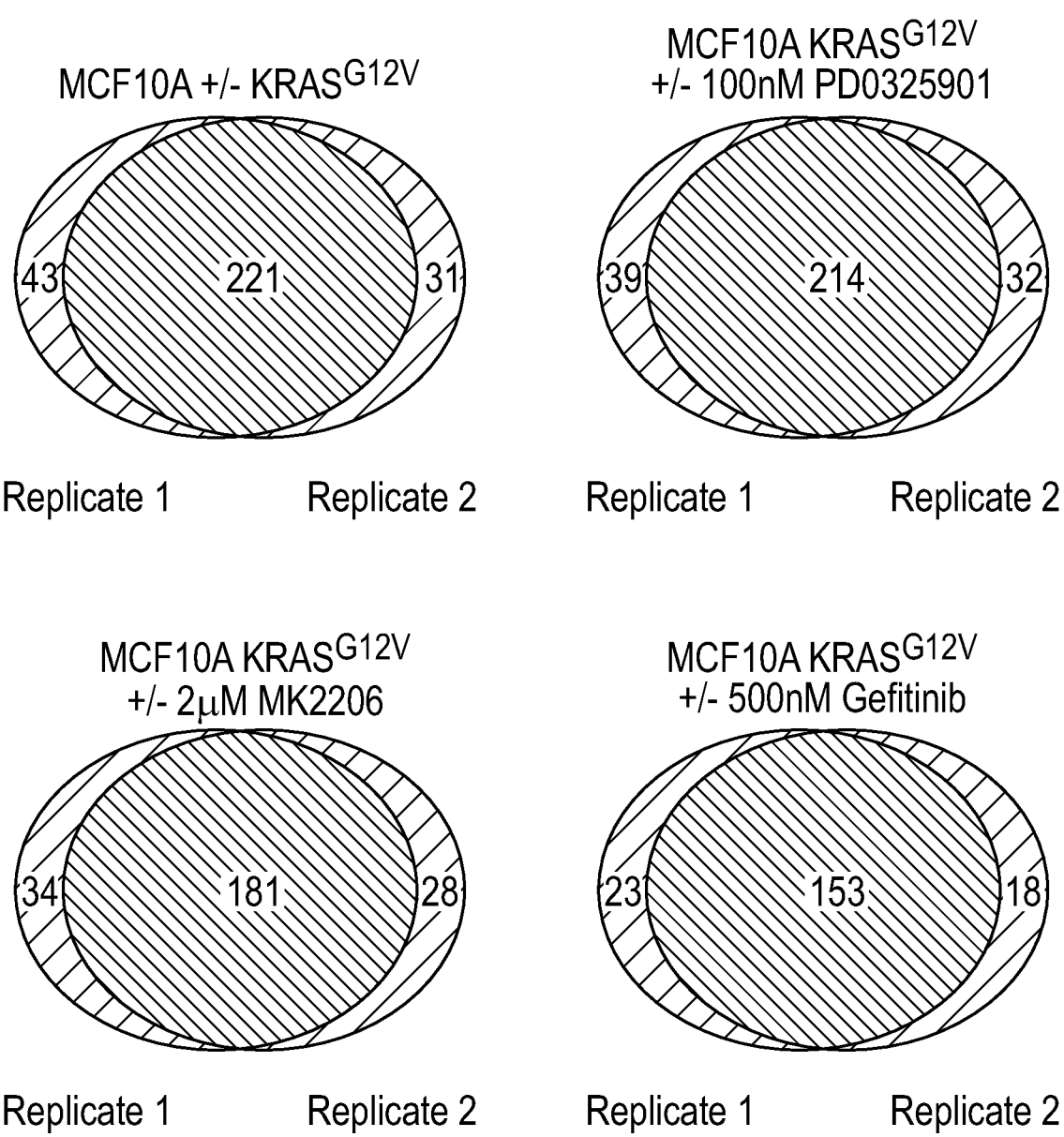
Figure 2C:
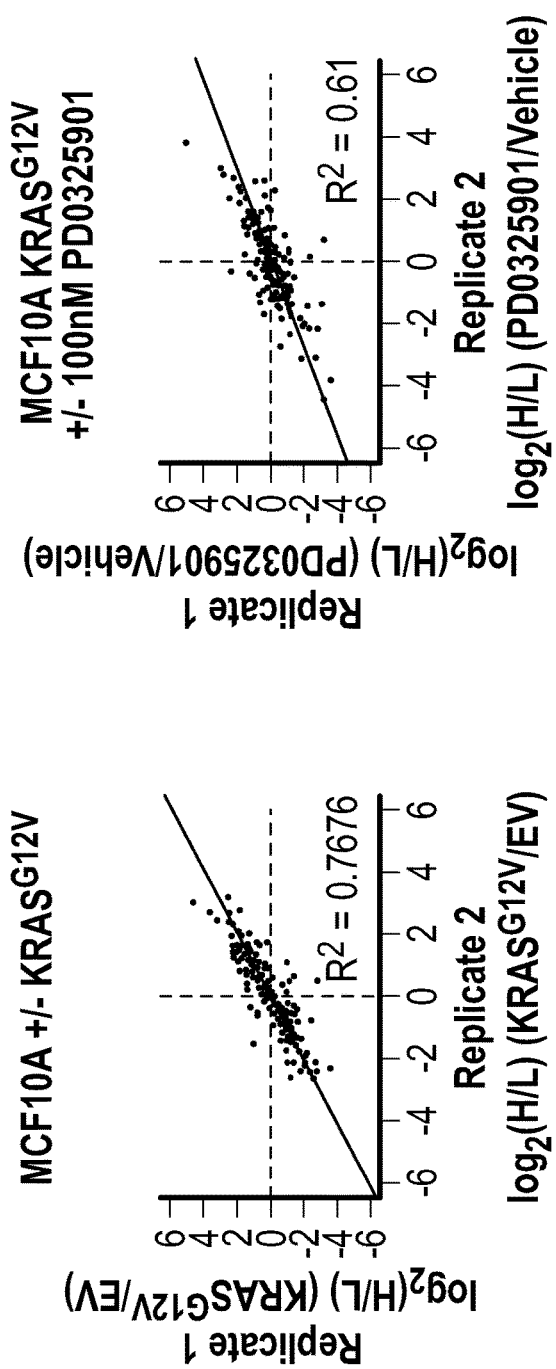
Figure 2C:
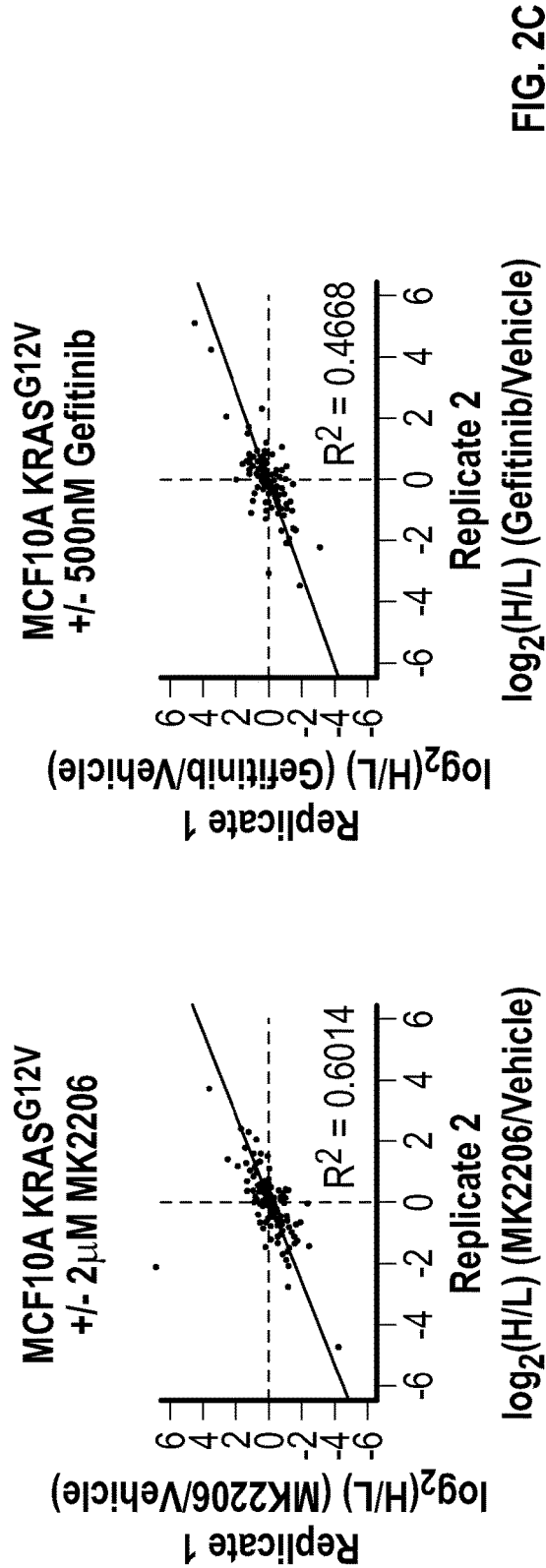
Figure 2D:
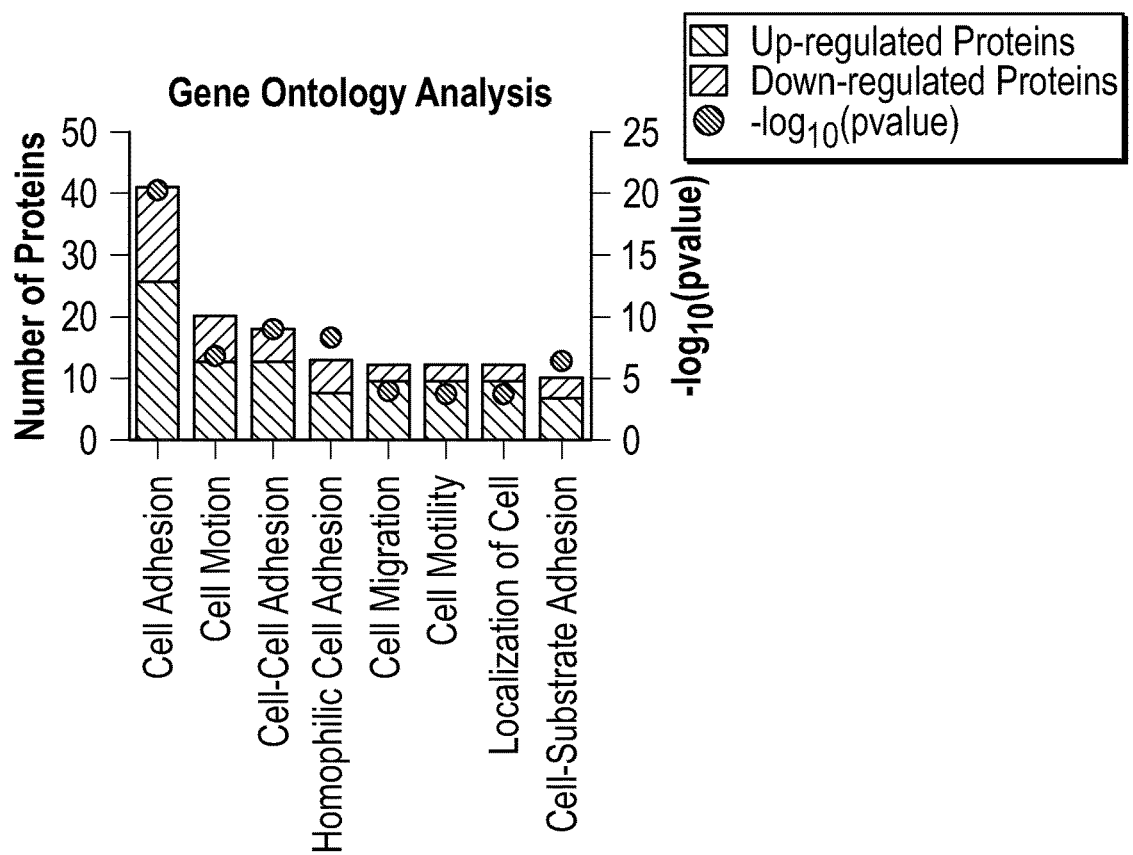

To measure changes in the cell surface proteome in an unbiased manner, a glycoprotein capture and enrichment proteomic method was employed (see, e.g., Schiess et al., Molecular & Cellular Proteomics 8, 624-638, 2009; and Wollscheid et al., Nature Biotechnol, 27, 378-386, 2009). The method illustrated in FIG. 1A was adapted to quantitatively compare the surface protein levels on the MCF10A cells with or without oncogenic KRASG12V, using stable isotope labeling with amino acids in cell culture (SILAC) (Ong and Mann, Nature Protocols, 1:2650-2660, 2006). In total, about 500 proteins were identified as common in both the MCF10A cells with and without KRASG12V. In total 17 proteins were identified as significantly upregulated in the MCF10A cells with KRASG12V, and 22 were identified as significantly downregulated (fold-change>+/−1.75; p-value<0.01) (FIG. 1B). Interestingly, gene ontology (GO) analysis of these significantly altered proteins in the datasets revealed significant enrichment for proteins involved in cell adhesion, cell motion, and cell-cell adhesion (FIG. 2D).

To gain insight on how different signaling pathways emanating from RAS were contributing to the changes in the surfaceome, the same proteomics approach was employed, except that the consequences of treatment with well-established pharmacological inhibitors, MEKi (PD0325901) and AKTi (MK2206) were examined. These two inhibitors block the two classic pathways downstream of RAS, MAPK and PI3K, respectively (Barrett et al., Bioorganic & Medicinal Chemistry Letters, 18:6501-6504, 2008; and Hirai et al., Molecular Cancer Therapeutics, 9:1956-1967, 2010). As a control, the effect of gefitinib (Moasser et al., Cancer Research, 61:7184-7188, 2001), which inhibits EGFR, a receptor tyrosine kinase found upstream of RAS, was also tested. In each experiment, cells were treated with subtoxic concentrations of drug for 72 hours and compared to vehicle treated MCF10A KRASG12V cells. For the MEKi experiment, the relative expression levels of 250 proteins (FIG.

Figure 1D:
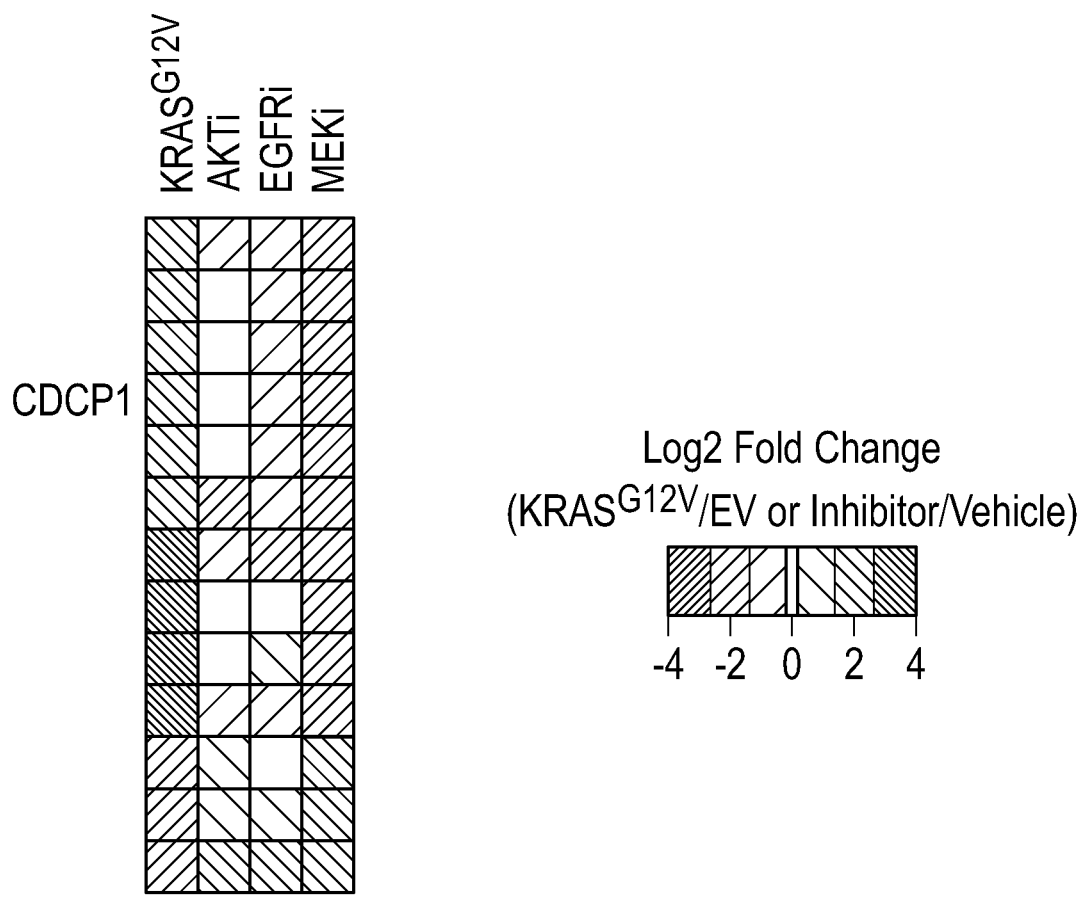
Figure 1E:
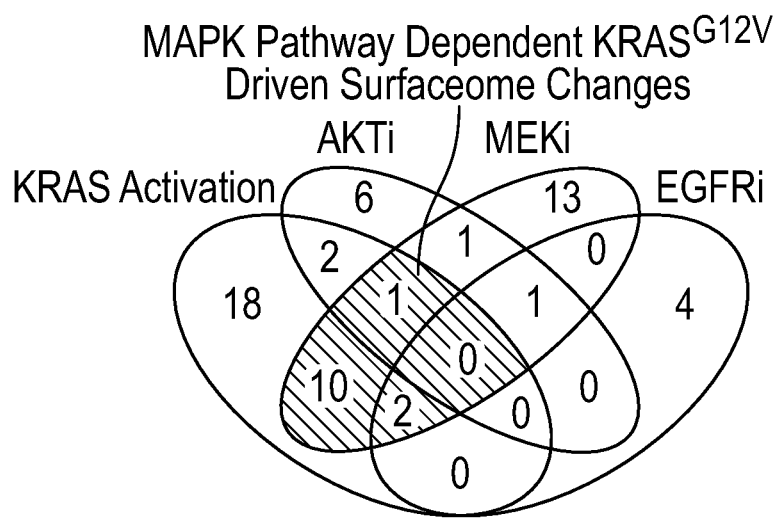
Figure 2E:
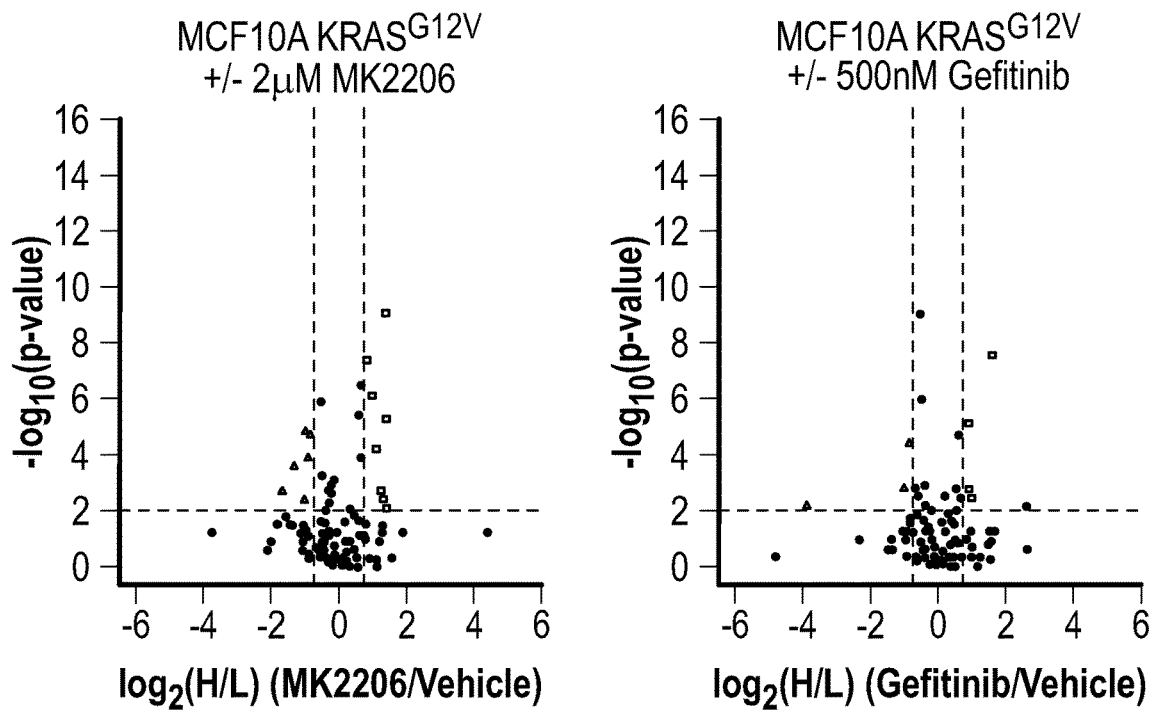
Figure 2F:
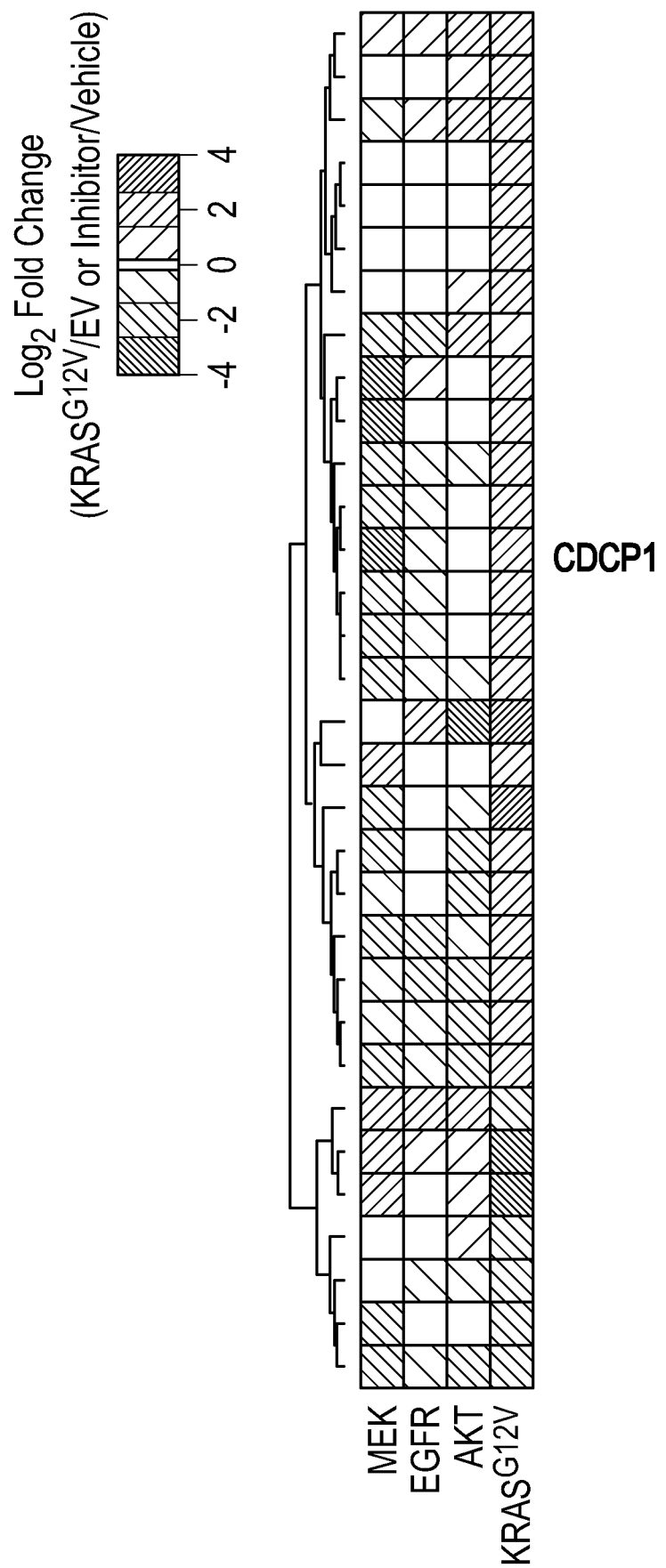

1C) were quantified. Remarkably, 13 of the proteins that were significantly altered by KRASG12V signaling were reversibly influenced by MEKi in the KRASG12V cells (FIG. 1D). By contrast, when the KRASG12V cells were treated with AKTi or EGFRi, very few significant changes were observed (FIG. 1E and FIGS. 2E and 2F). These findings indicate that the MAPK pathway is likely the dominant pathway by which RAS mediates influence on the surfaceome in the MCF10A model. Taken together with the unbiased GO analysis, these results suggest that RAS signaling through the MAPK pathway promotes the coordinate expression of proteins that may contribute to increased invasiveness, metastasis, and epithelial to mesenchymal transition.

Figure 1F:
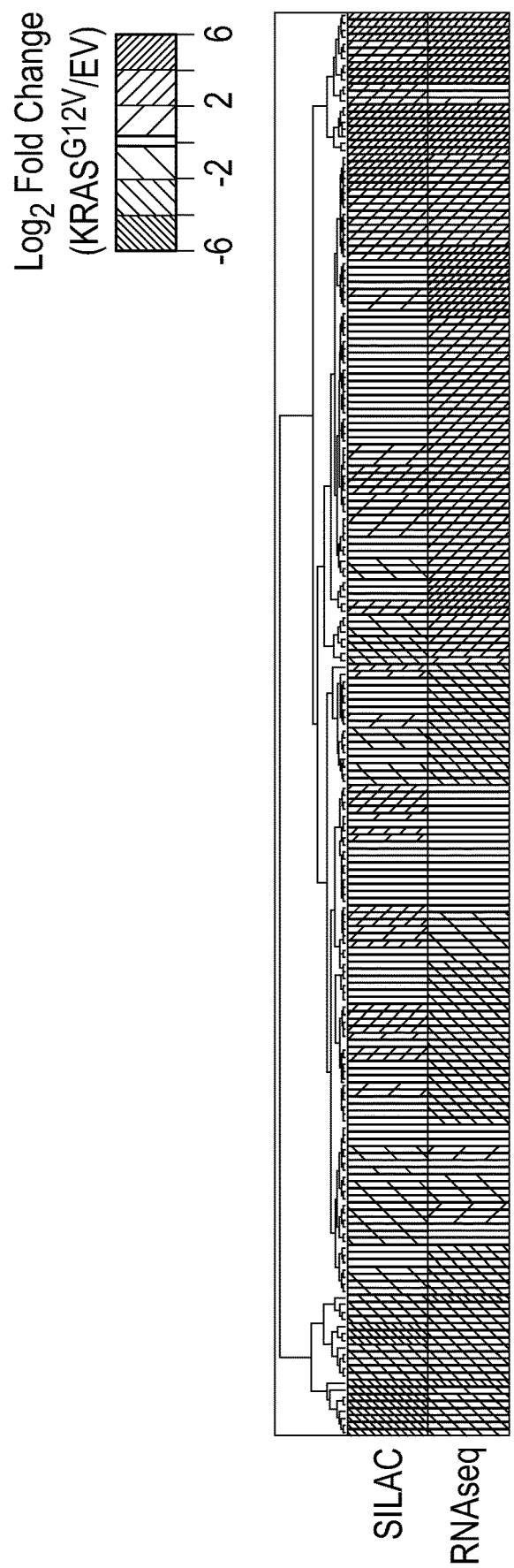

To further characterize the influence of oncogenic KRAS on the surface proteome, RNAseq was performed on both the MCF10A empty vector control and KRASG12V cells. The correlation between expression level changes observed in the SILAC proteomic data with those from RNAseq data (FIG. 1F) was modest but significant (R2=0.422). This is not surprising as there are many possible points of regulation between synthesis of an mRNA and trafficking of a protein to the cell surface that can blur the connection between steady state RNA and protein levels. Nonetheless, the combination of the proteomic and transcriptomic data reinforces the notion that KRAS transformation drives significant and coordinated changes in the cell surface. Additionally, a large cluster of genes was identified as being upregulated in both data sets; thus providing a set of high-confidence KRAS signaling surface markers for further validation.

Example 2: Generation of Recombinant Antibodies that Target the KRAS Surfaceome

To validate the results of the surfaceome characterization, recombinant monoclonal antibodies were generated and validated for a set of the most interesting KRAS induced targets. Recombinant antibodies are particularly useful as they can be bioengineered for many useful applications including therapeutic payload delivery and in vivo imaging. The quantitative proteomic and RNAseq data was utilized to choose seven high-confidence KRAS-induced single-pass transmembrane receptors to generate recombinant antibodies.

Figure 3A:
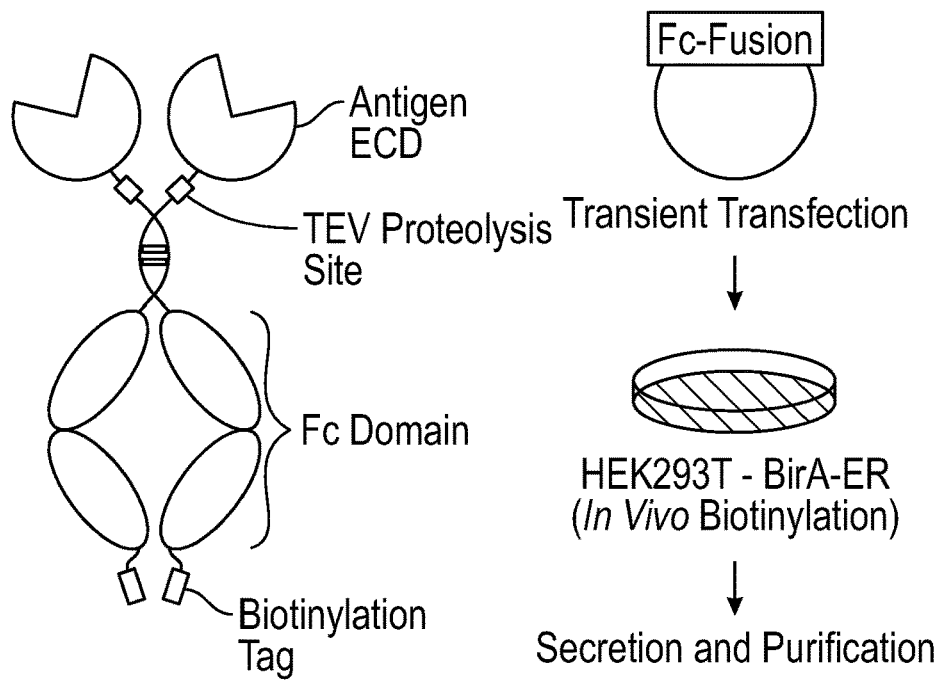
FIG. 3A-3F depicts the validation of oncogenic KRAS-induced cell surface proteins with novel recombinant antibodies.
Figure 3B:
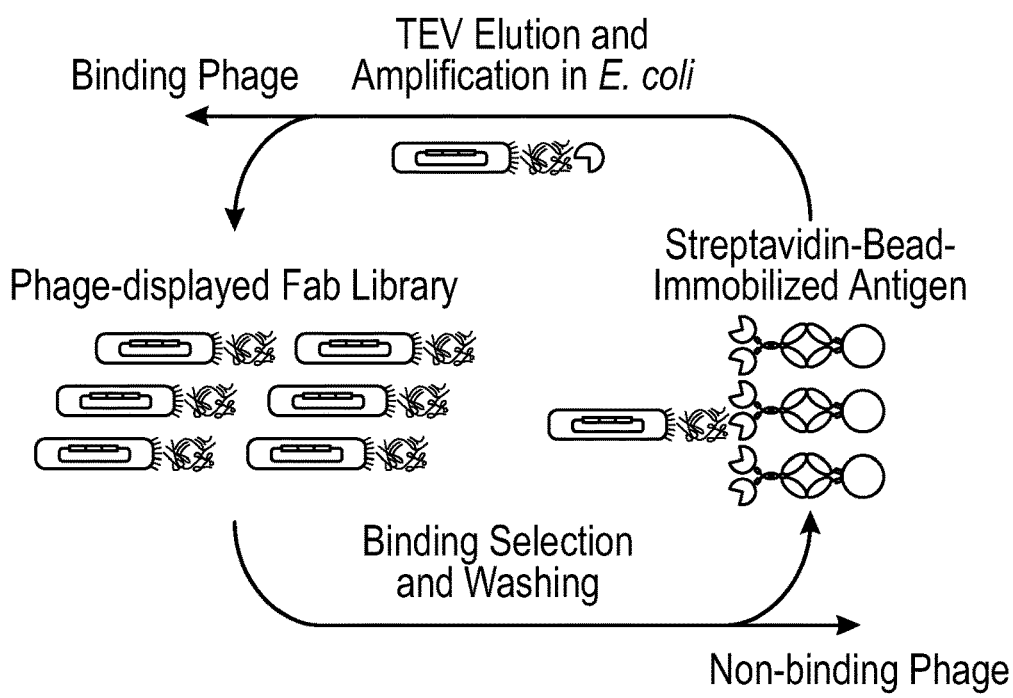
Figure 4A:
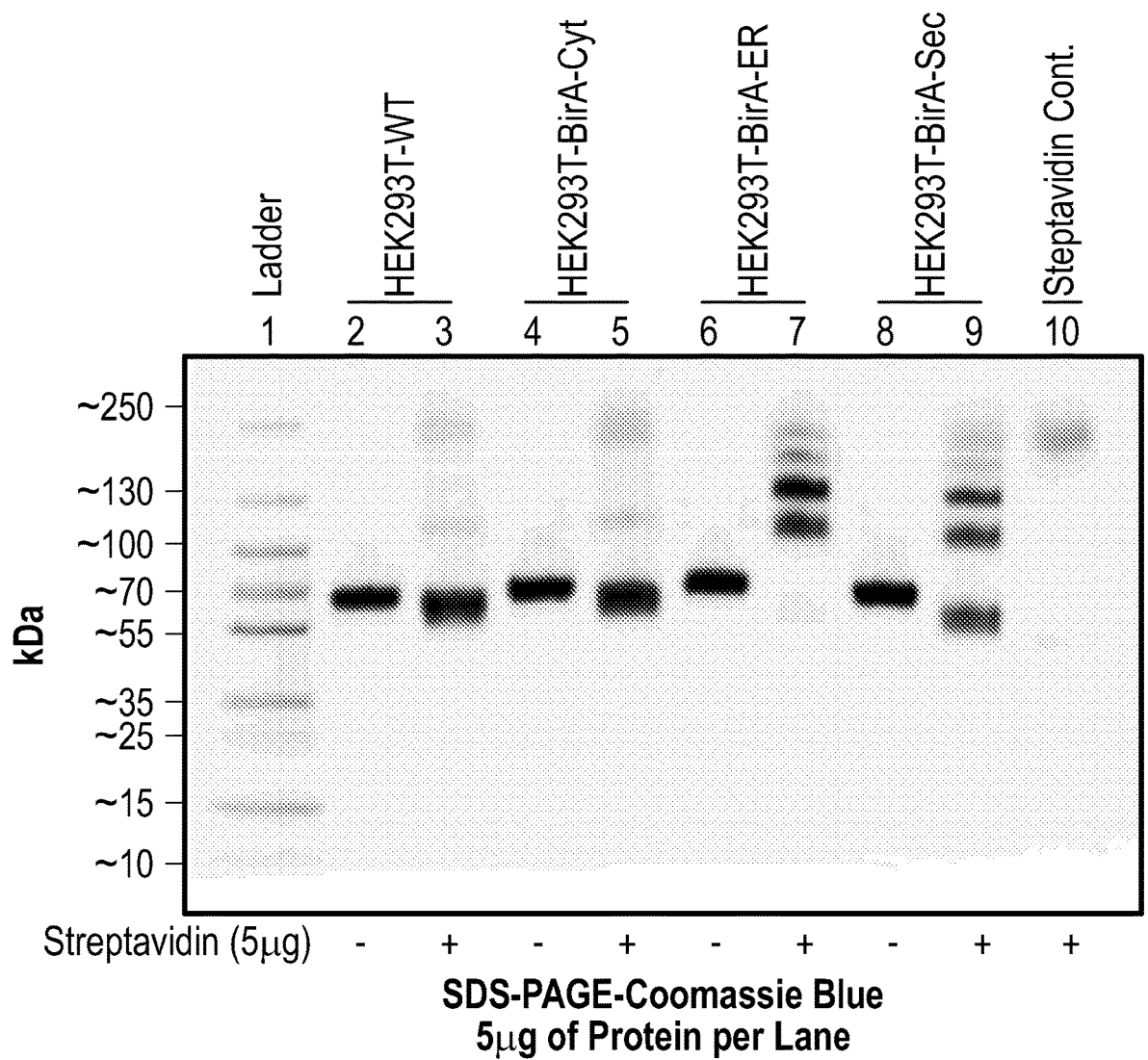
Figures 1, 4B:
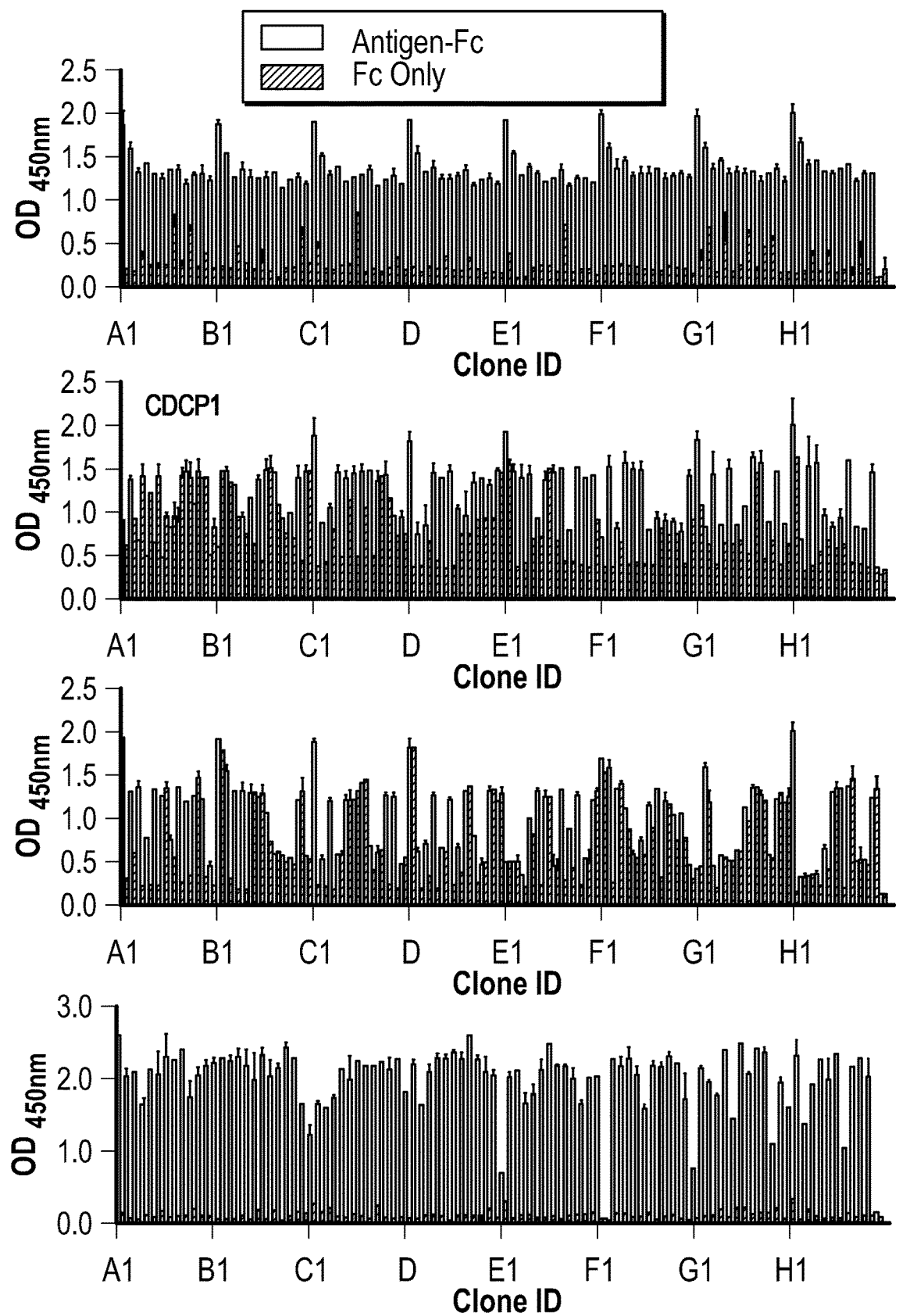
Figures 2, 4B:
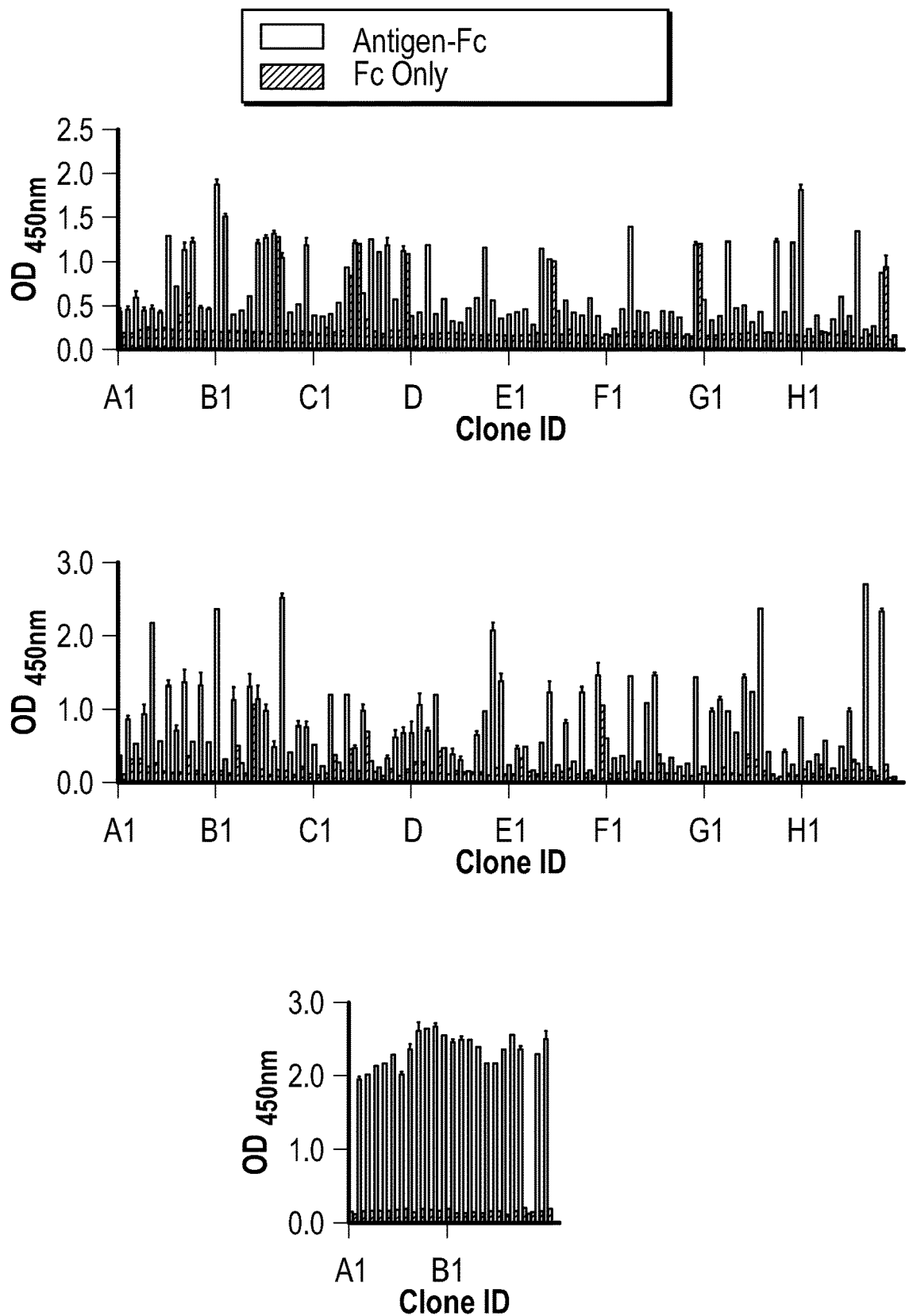

As illustrated in FIG. 3A, to enable the rapid expression and purification of these target proteins for generation of antibodies by phage display, their extracellular domains (ECDs) were expressed as Fc-fusion proteins in mammalian cells (Czajkowsky et al., EMBO Mol Med 4:1015-1028, 2012). A biotin-acceptor-tag was introduced at the C-terminus, and a TEV proteolysis site was also introduced between the ECD and Fc-domain. These tags allowed for site-selective capture of the ECD-Fc fusion on magnetic streptavidin beads, and release of each ECD containing bound Fab-phage after TEV treatment. This "catch-and-release" strategy illustrated in FIG. 3B ensured selective release of Fab-phage bound to each ECD, while avoiding enrichment of unwanted Fab-phage that either bound the Fc-domain or the streptavidin beads (Hornsby et al., Molecular & Cellular Proteomics, 14:2833-2847, 2015). Four rounds of "catch-and-release" were conducted with a well-validated synthetic Fab-phage library (Persson et al., J Mol Biol, 425:803-811, 2013). After each selection, individual phage clones were isolated and screened for target binding by phage ELISA followed by DNA sequencing (FIGS. 4B1 and 4B2). Selections resulted in the identification of 116 unique antigen-binding sequences against the seven ECD-Fc fusion targets. None of these clones demonstrated appreciable binding to the Fc-domains fused to the antigen.

Figure 3C:
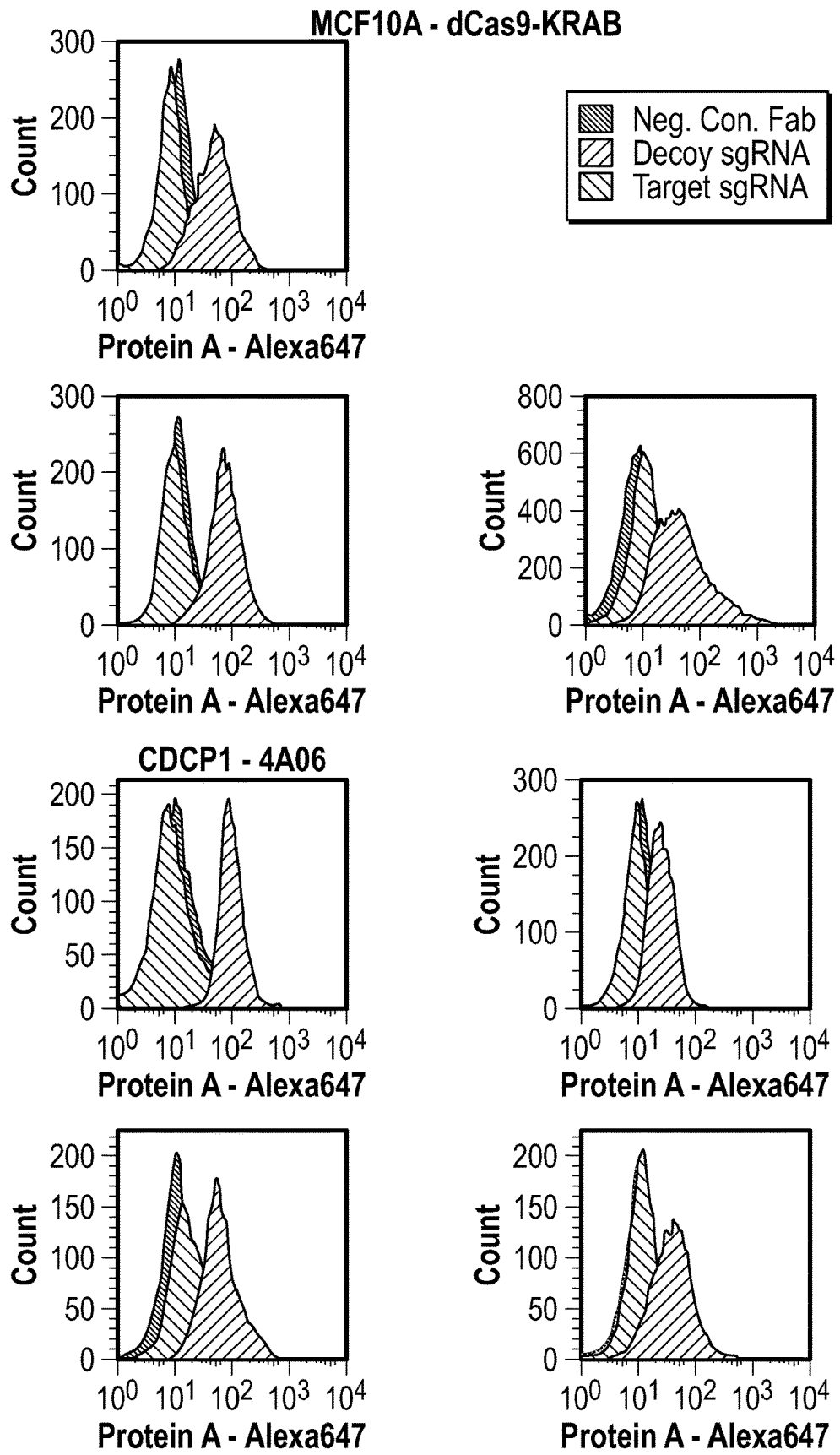
Figure 4C:
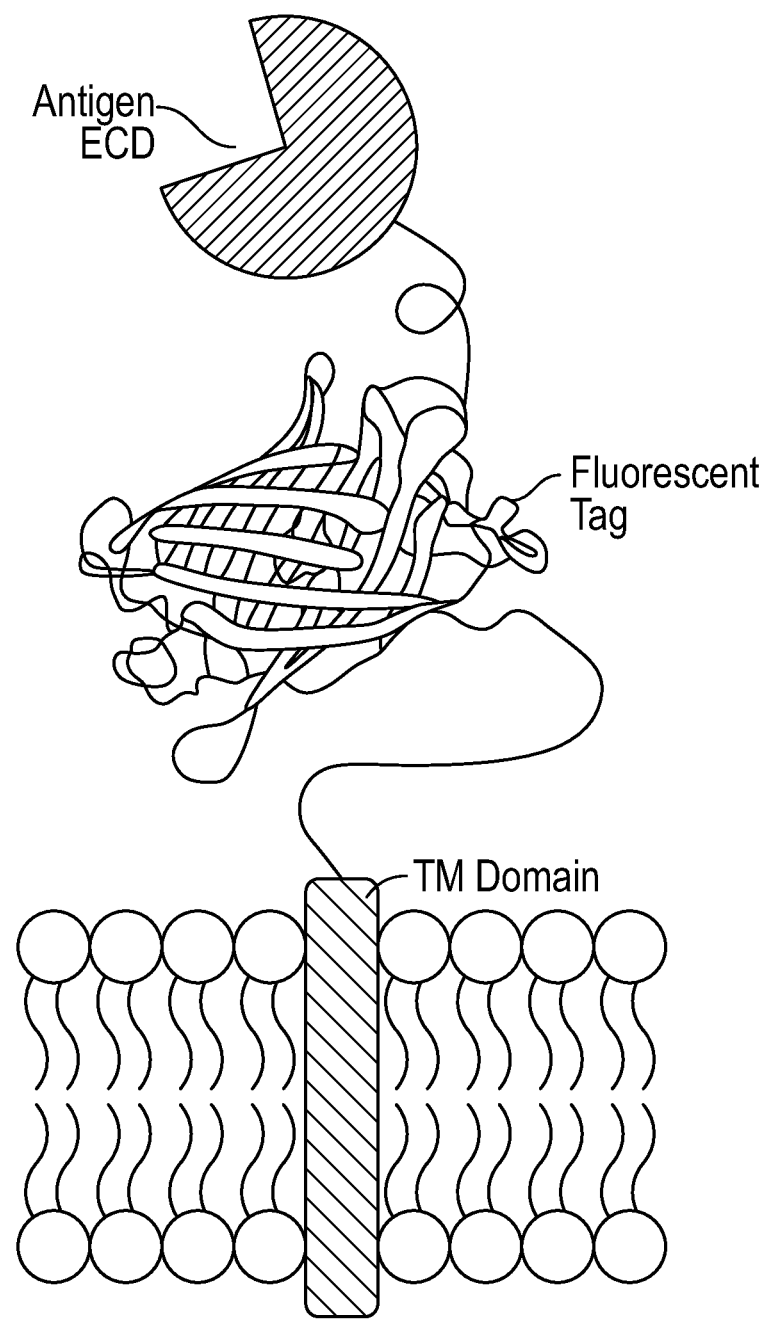
Figure 4D:
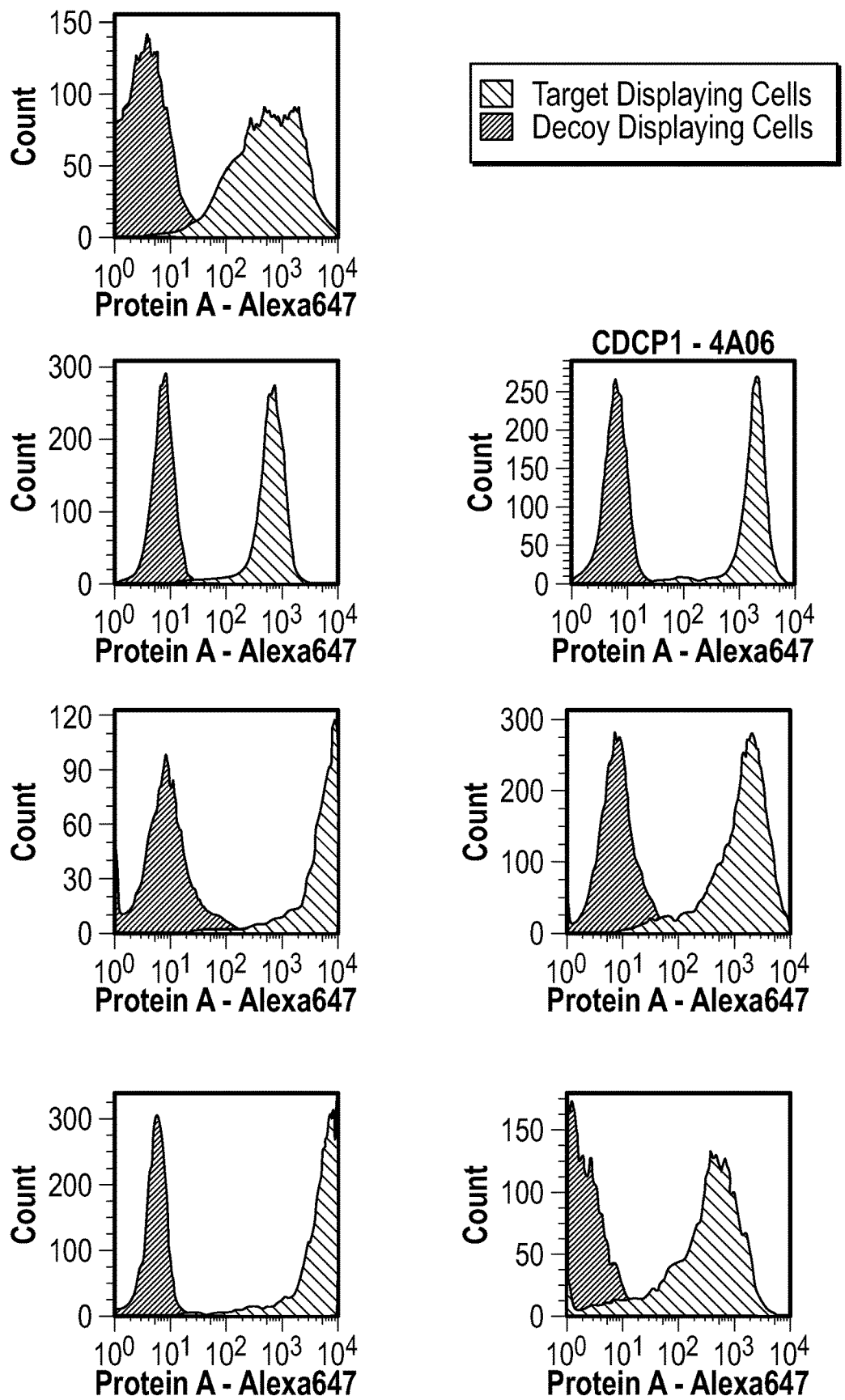

To validate the specificity of the antibodies, several of the tests recently recommended by the Working Group for Antibody Validation were used (Uhlén et al., Nature Methods, 13: 823-827, 2016). First, a stable cell line was generated for each target that overexpressed the protein ECD fused to a fluorescent protein expression reporter and a generic single-pass transmembrane domain (FIG. 4C). Selections to each target resulted in the identification of multiple antibodies showing dramatically increased binding to cells over-expressing the target ECD as compared to control cells (FIG. 4D). The most stringent of the protocols validated the specificity of the antibodies using CRISPRi knockdown of each target in the MCF10A KRASG12V cells (Gilbert et al., Cell, 154:442-451, 2013). In each case, at least one antibody (including CDCP1-002) exhibited significant staining on the MCF10A KRASG12V cells and little to no binding for the CRISPRi knockdown corresponding cell line (FIG. 3C). Importantly, these data also corroborated the proteomics observation that these membrane proteins are highly expressed in the MCF10A KRASG12V cells. Binding characteristics of various Fabs were further assessed by flow cytometry (mean fluorescence intensity) and ELISA, and details are provided below in Table 2-1.

TABLE 2-1

| | Fab Binding Characteristics | | | | | |
|---|---|---|---|---|---|---|
| | Flow Cytometry (MFI) | | ELISA ~EC50 Kd (nM) | | ELISA CDCP1 Specificity | |
| Fab | Decoy Cell | CDCP1 Cell | Human CDCP1 | Monkey^ CDCP1 | aas 30-367 | aas 370-667 |
| CDCP1-002 | 1.02 | 1160 | 0.6512 | 19.57 | Yes | No |
| CDCP1-003 | 1.04 | 180 | 65.28 | 666.24 | Yes | No |
| CDCP1-004 | 1.01 | 770 | 2.369 | 34.9 | Yes | No |
| CDCP1-005 | 1.87 | 870 | ND | ND | Yes | No |
| CDCP1-006 | 1.01 | 52.3 | 29.63 | 3.338 | No | Yes |
| CDCP1-007 | 1.01 | 2.33 | 17.99 | 22.42 | Yes | No |
| CDCP1-008 | 1.19 | 673 | 76.25 | 97.1 | Yes | No |

^Cynomolgus monkey

Example 3: Validation of Oncogenic KRAS-Induced Membrane Proteins

Figure 3D:
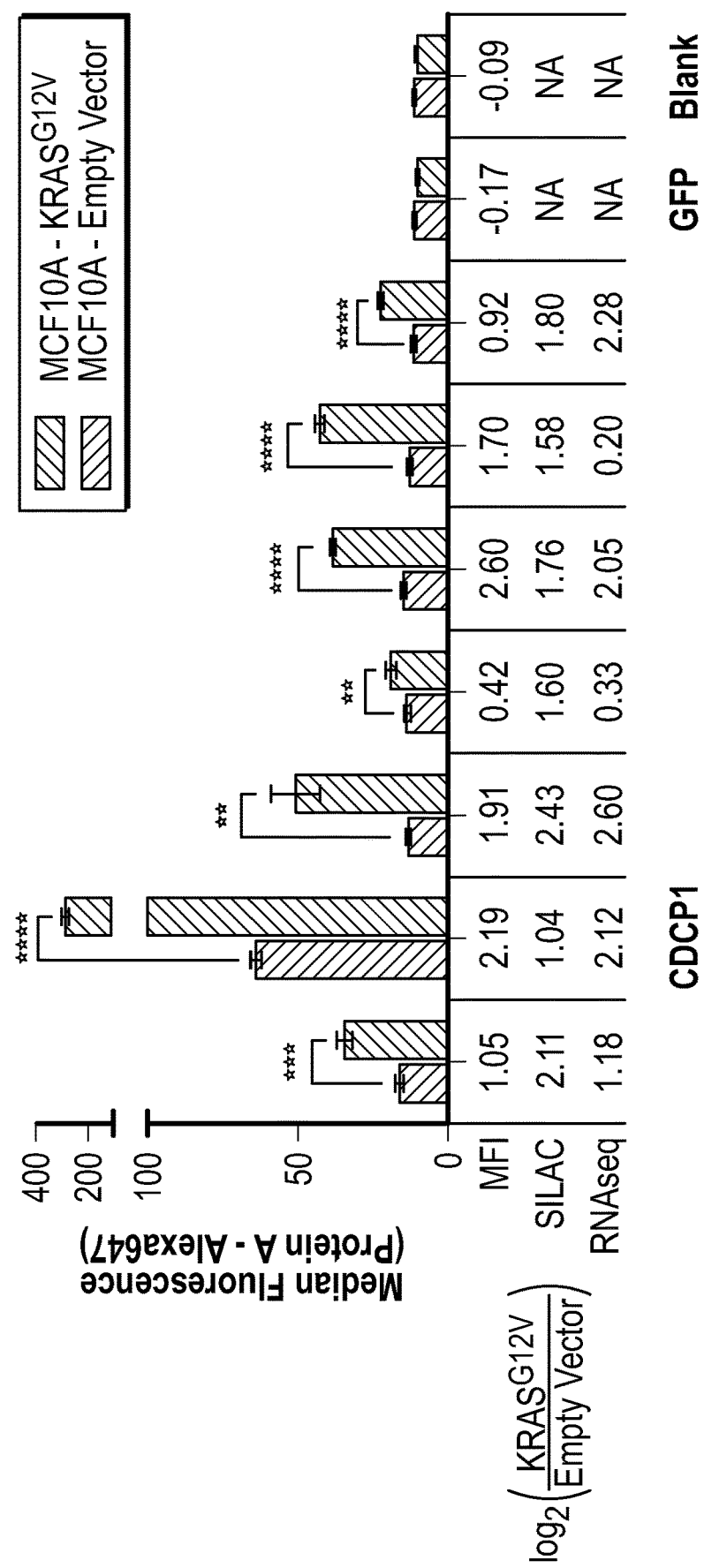
Figure 3E:
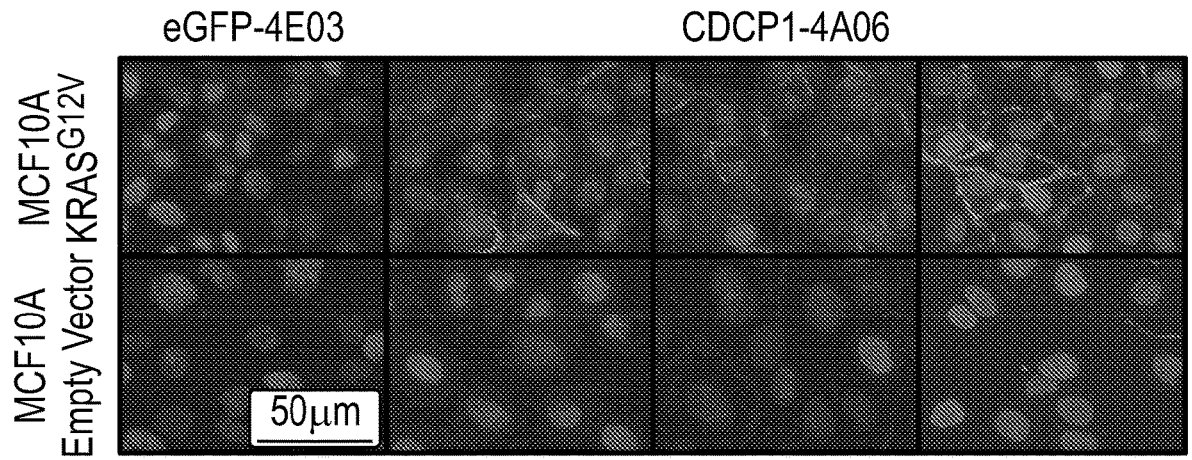

To validate the observations made by mass spectrometry-based proteomics and RNAseq analysis, the relative cell-surface abundance of each protein was measured using flow cytometry with the recombinant antibodies (including CDCP1-002). The CDCP1 protein showed elevated expression on the MCF10A KRASG12V cells relative to the empty vector control (FIG. 3D). Moreover, the flow cytometry data generated with the Fabs correlated with the proteomic measurements. These results were further confirmed by immunofluorescence for a subset of the targets, where both differential expression and cell surface localization was observed in each case (FIG. 3E).

Figure 3F:
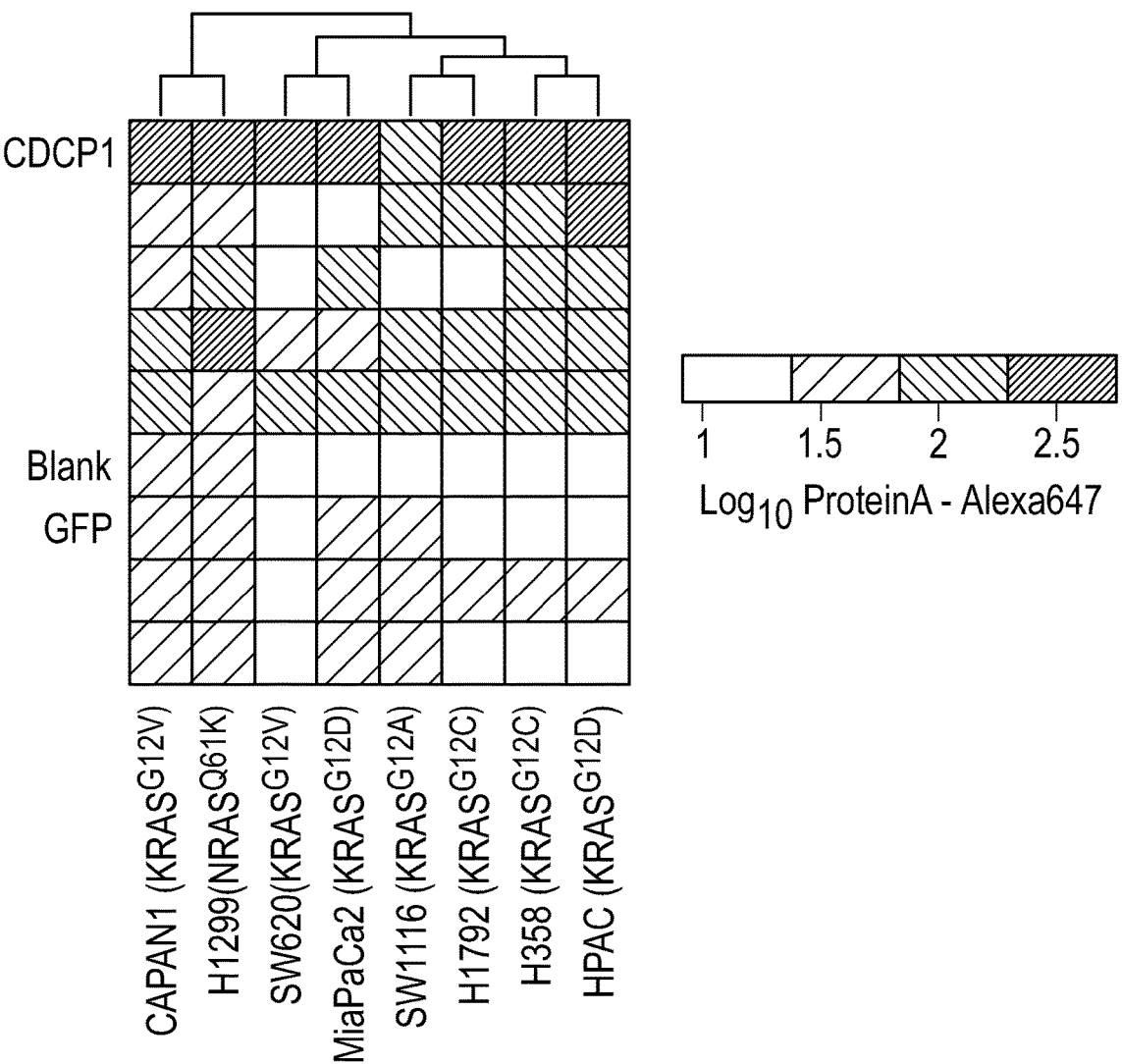

Next, the relative expression of the target proteins was measured on a panel of tumorigenic cells that included lung, colorectal, and pancreatic cancer cell lines known to harbor oncogenic RAS mutations (FIG. 3F). These three cancer types have the highest occurrence of oncogenic KRAS. High levels of expression of CDCP1 were observed in at least half of the eight cancer cell lines.

Figure 5A:
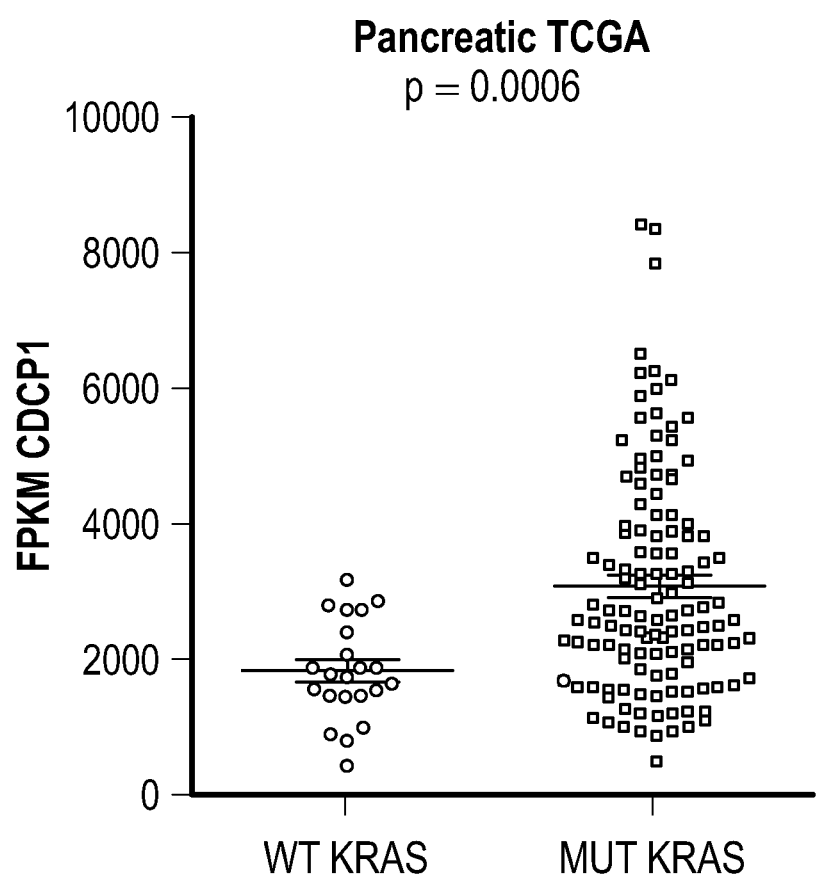
FIG. 5A-5G depicts the characterization of CDCP1 as a potential therapeutic target in pancreatic ductal adenocarcinoma (PDAC).
Figure 5B:
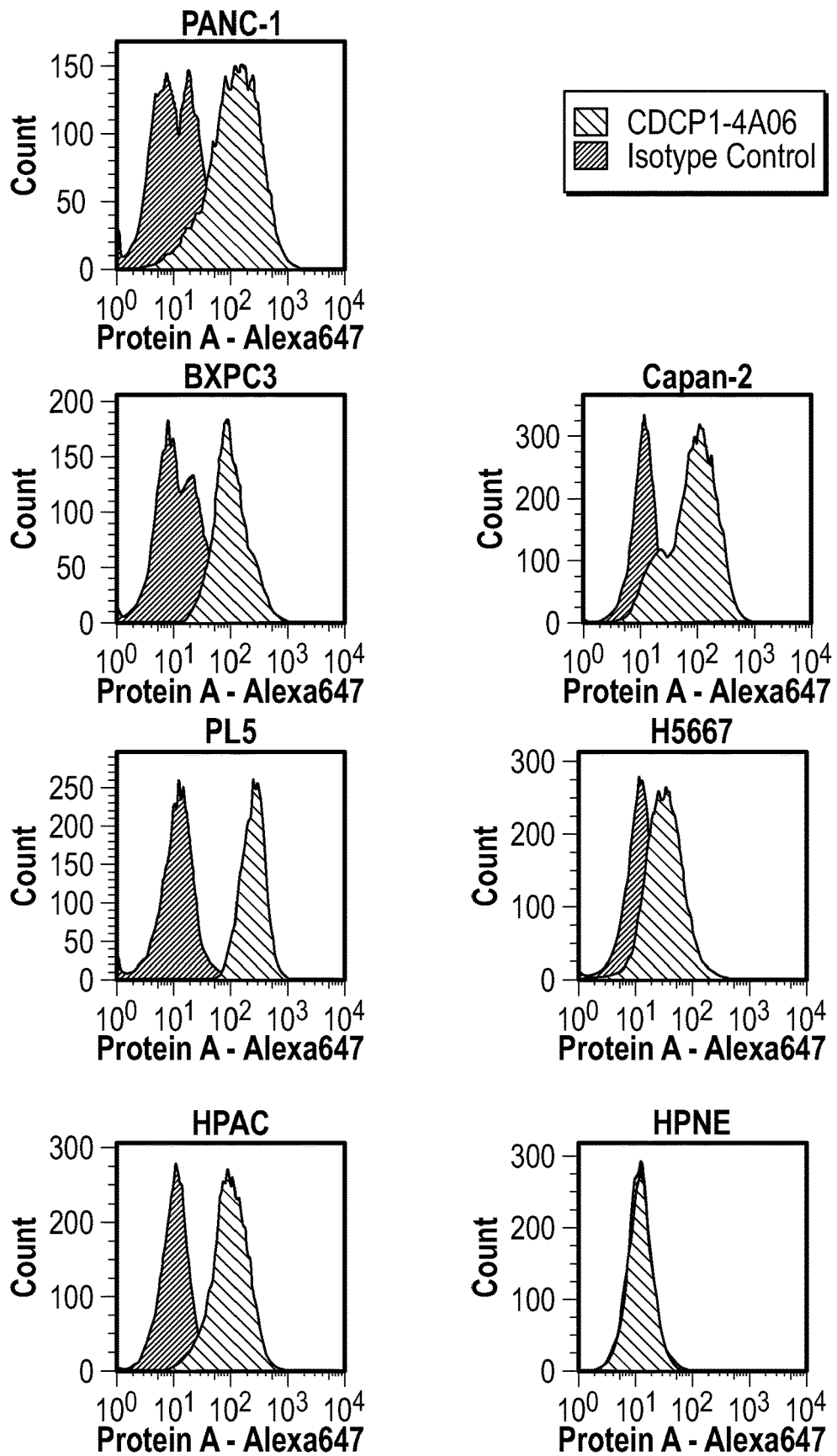
Figure 6A:
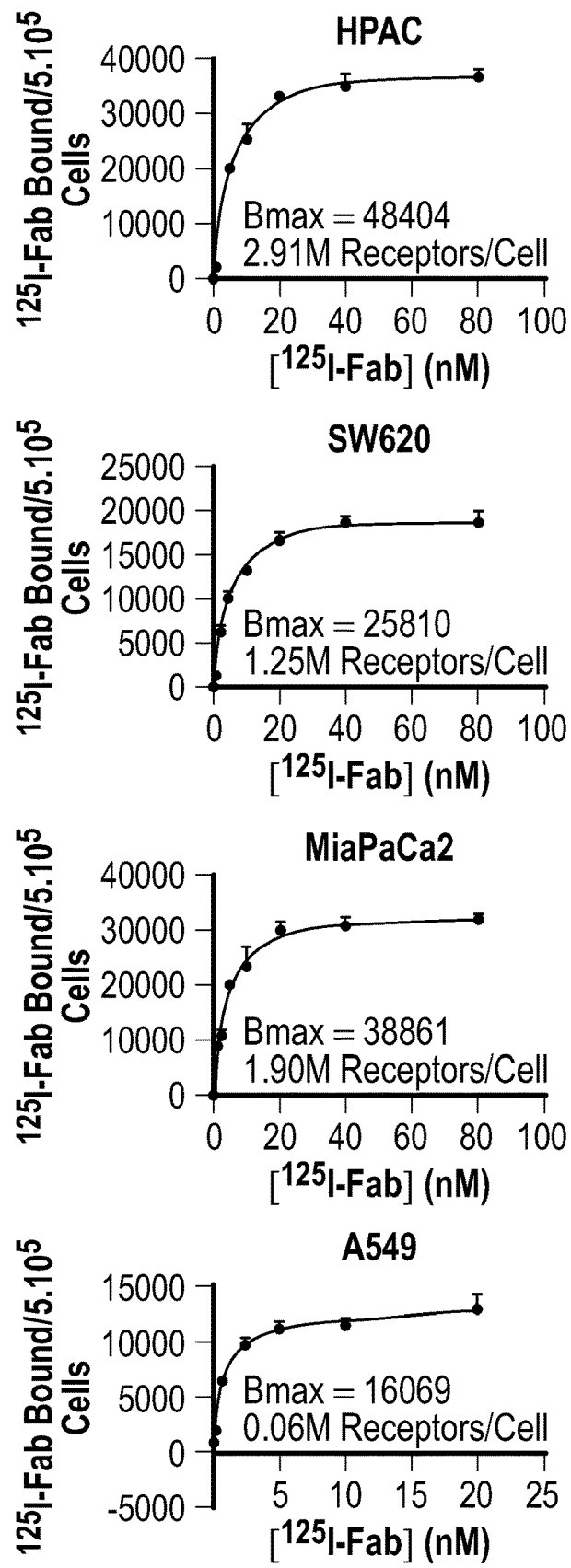
FIG. 6A-6C depicts the characterization of CDCP1 expression levels in cancer cell lines and in normal human tissues.
Figure 6B:
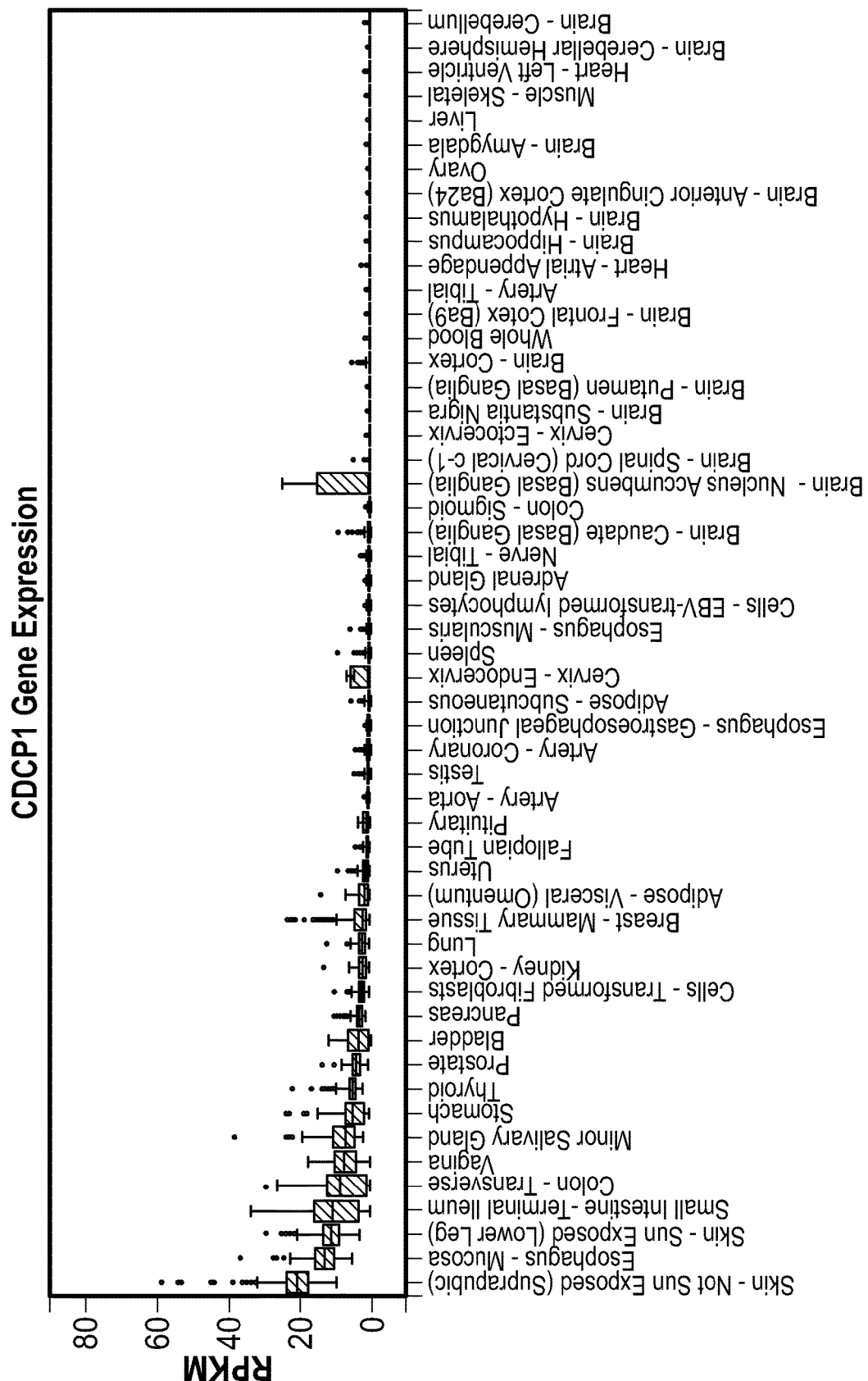
Figure 6C:
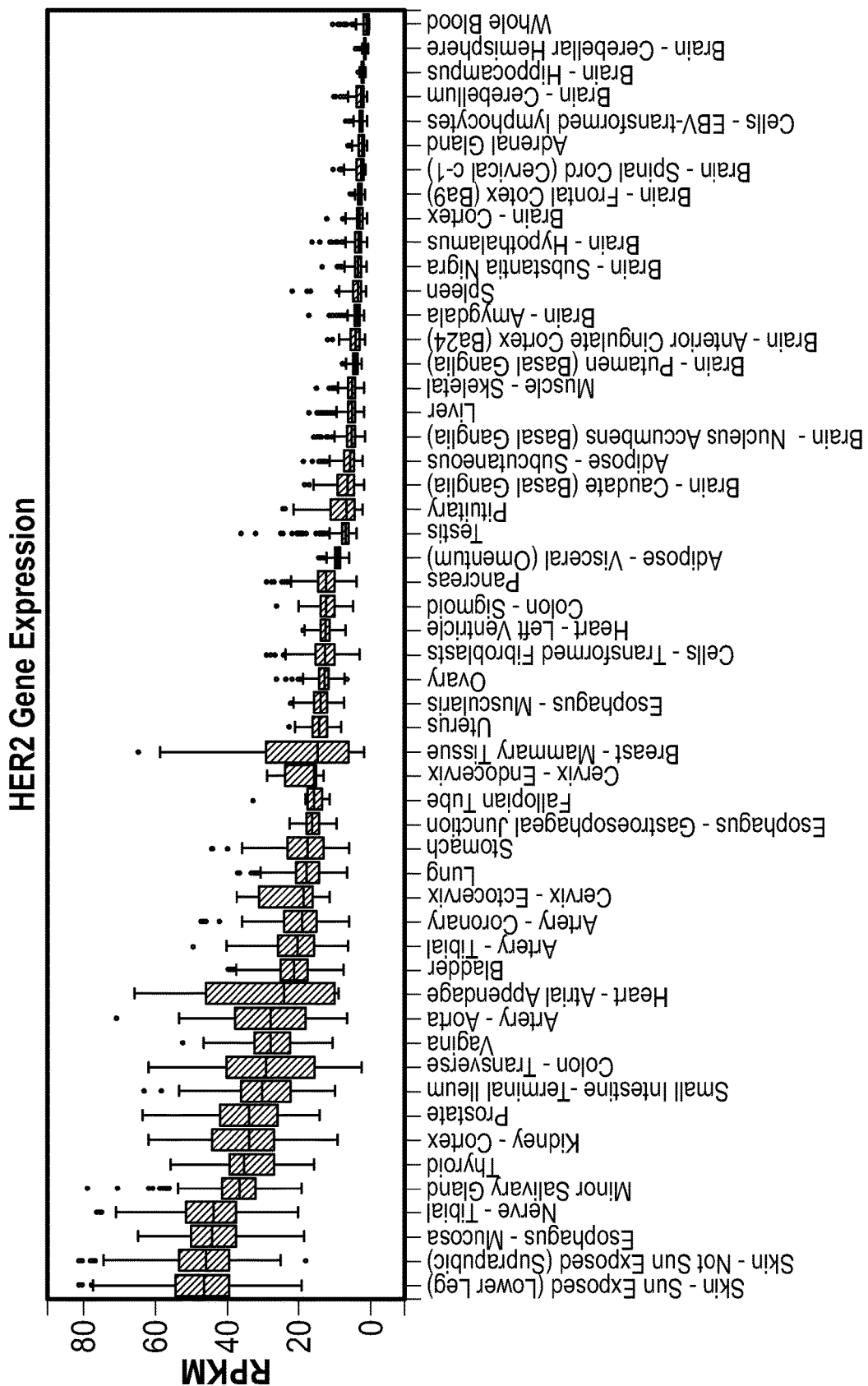

Example 4: A CDCP1 Antibody can Selectively Deliver Toxic and Immunotherapy Payloads to Pancreatic Cancer Cells Expressing Oncogenic KRAS Oncogenic KRAS is nearly ubiquitously expressed in pancreatic cancers (Eser et al., British Journal of Cancer Research, 111:817-822, 2014). Transcriptomics data derived from The Cancer Genome Atlas revealed that CDCP1 transcript abundance was significantly upregulated and correlated with KRAS mutational status (FIG. 5A). CDCP1 expression levels were profiled on a panel of human pancreatic ductal adenocarcinoma cancer (PDAC) cell lines, and high level of expression of CDCP1 was observed, relative to no observable expression on non-tumorigenic pancreatic duct cells, HPNE (FIG. 5B). Indeed, quantification of the protein copy number of CDCP1 on the HPAC PDAC cells revealed that these cells express about 2.9 million copies per cell (FIG. 6A). Such high level of expression is rare, and is an important consideration for therapeutic targeting by antibody drug conjugates (Bornstein, The AAPS Journal, 17:525-534, 2015).

Figure 5C:
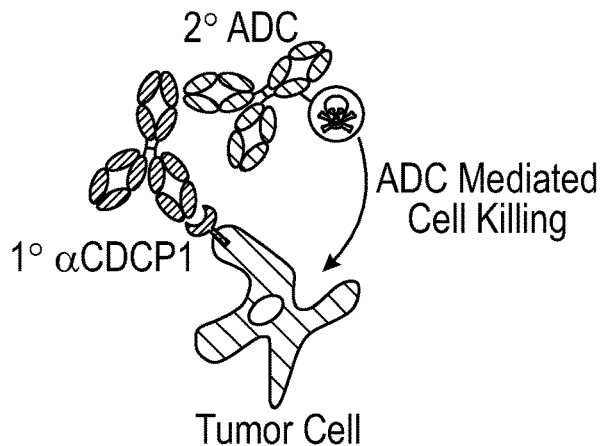
Figure 5D:
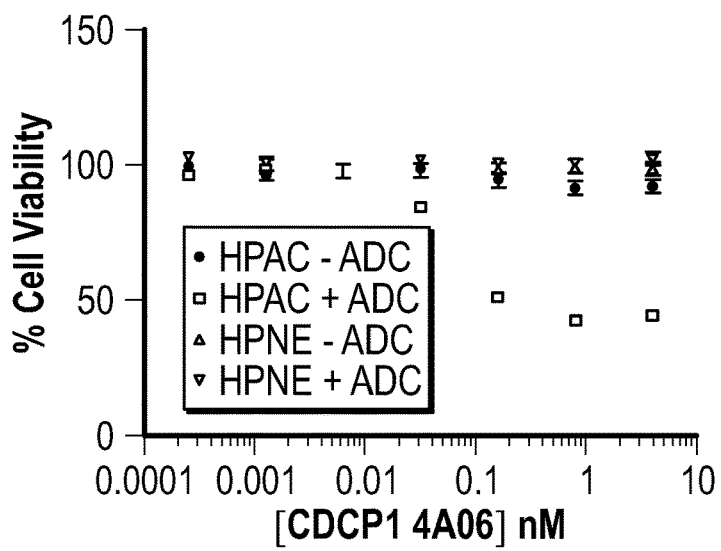
Figure 5E:
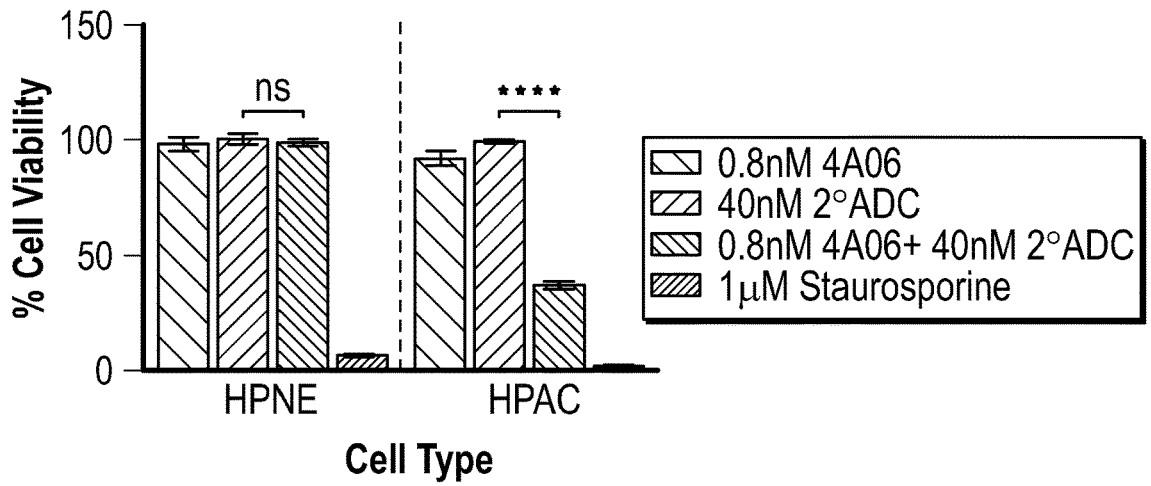

One of the recombinant CDCP1 antibodies (CDCP1-002) was tested for its ability to selectively deliver a cytotoxic payload to mutant KRAS tumor cells. Having the recombinant form of the antibody facilitated simple conversion of the Fab to an IgG1 for the experiment. The HPAC cells (tumorigenic) and HPNE cells (non-tumorigenic) were treated with anti-CDCP1 IgG1 that can bind a commercially available secondary antibody coupled to a non-cell permeable cytotoxic microtubule inhibitor monomethyl auristatin f (MMAF) (FIG. 5C). While the normal HPNE cells were unaffected by treatment of up to 20 nM of antibody complex, oncogenic KRAS-containing HPAC cells were sensitive to antibody complex treatment at concentrations as low as 10 pM (FIG. 5D). More than 60% reduction of viability was observed at 0.8 nM (FIG. 5E), indicating that the CDCP1-selective antibody can selectively internalize and deliver the cytotoxic payload. It is not surprising that all cells were not killed since these are rapidly dividing cells in culture that create a steady state of apoptosis and proliferation.

Figure 5F:
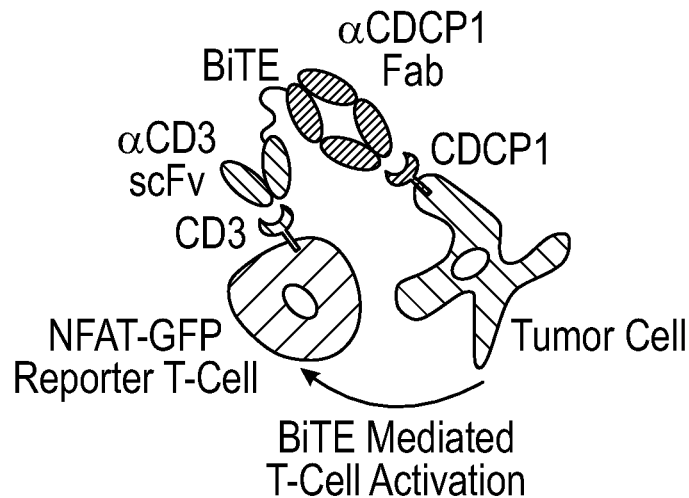
Figure 5G:
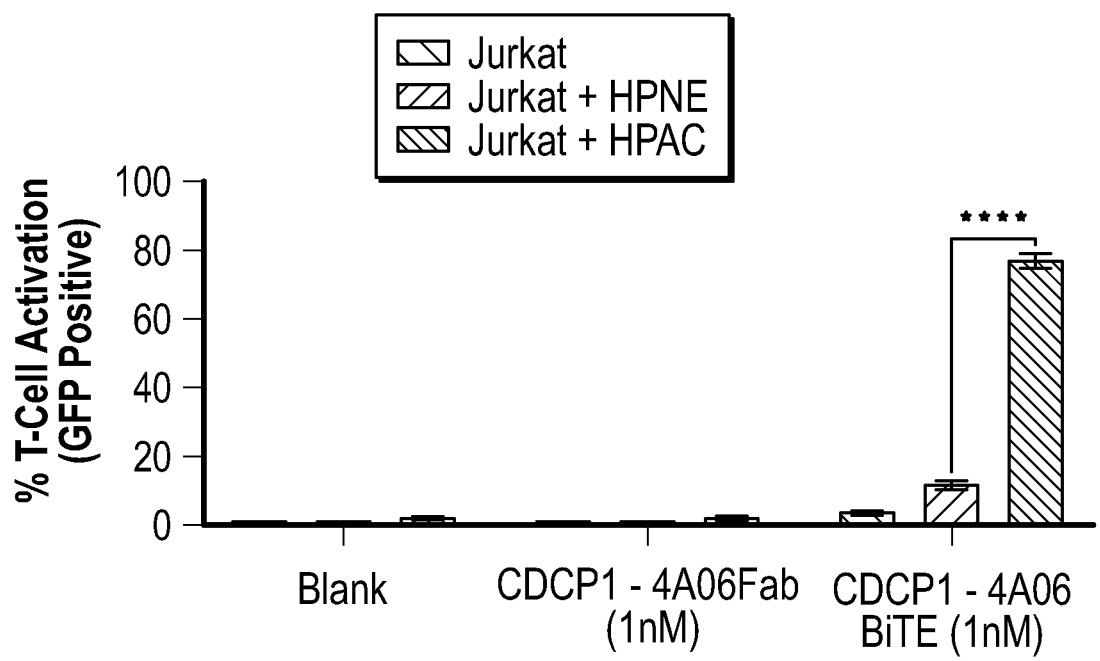

Recently, the U.S. Food and Drug Administration approved the first example of a bispecific T-cell engager (BiTE) antibody immunotherapy that binds both a tumor selective antigen, and CD3 on the surface of cytotoxic T-cells (Wu et al., J Hematol & Oncol, 8:104, 2015). Additional BiTEs are currently being tested in the clinic (Yuraszeck et al., Clinical Pharmacology & Therapeutics, 101:634-645, 2017). The BiTE recruits the T-cell to the tumor cell, induces T-cell activation, and tumor cell killing. The CDCP1 recombinant Fab can be engineered in a BiTE modality to selectively target oncogenic KRAS PDAC cells. The CDCP1 Fab (CDCP1-002) was genetically fused to the clinically utilized OKT3 anti-CD3 scFv, and this construct was tested to determine if it could be used to mediate T-cell activation in co-culture with tumor cells (FIG. 5F). Remarkably, 1 nM of the CDCP1 BiTE was sufficient to activate 75% of T-cells when co-cultured with mutant KRAS HPAC cells, while co-culture with HPNE cells, or treatment with BiTE lacking the anti-CD3 scFv, resulted in minimal activation (FIG. 5G).

Figure 7A:
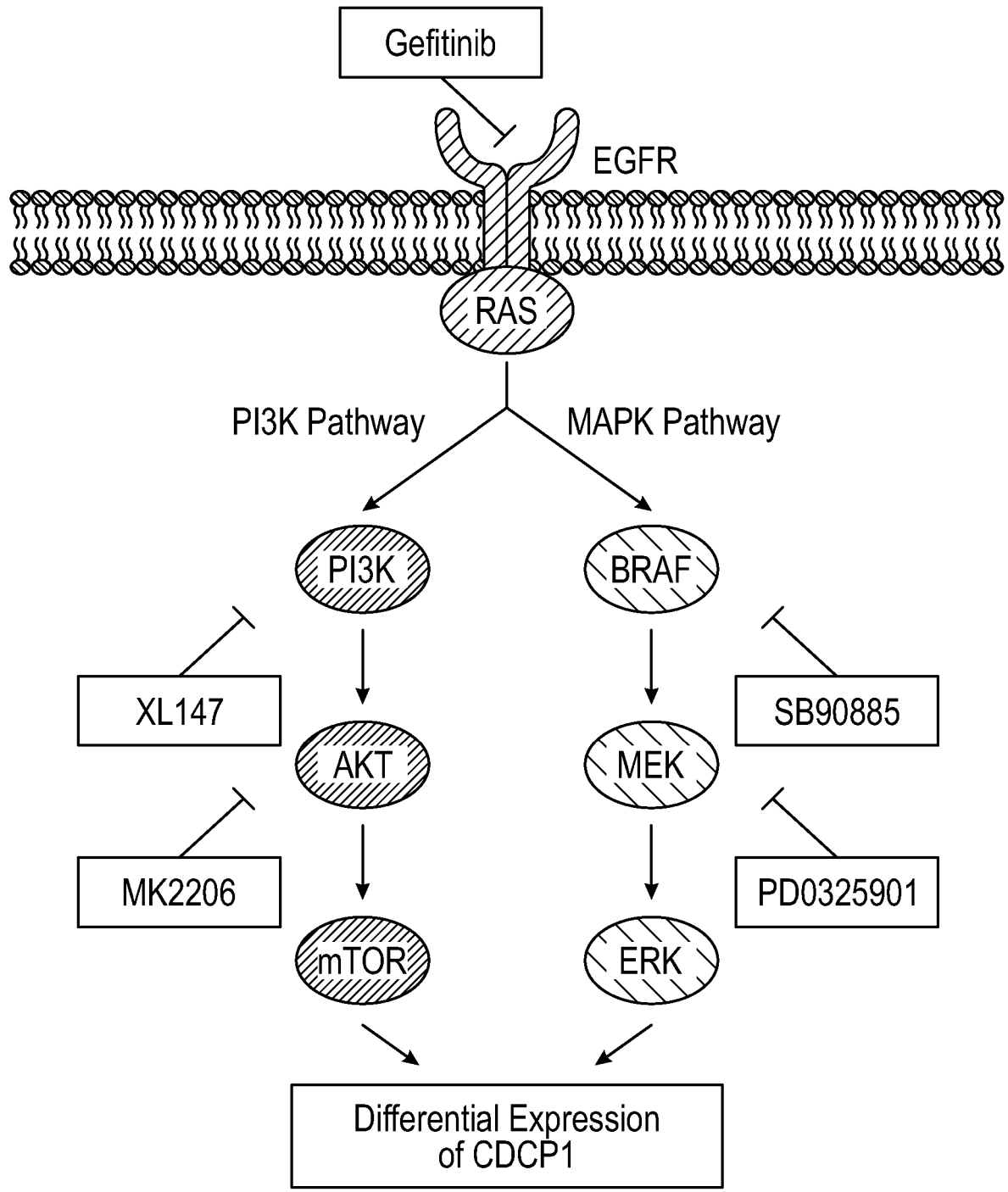
FIG. 7A-7E illustrates that CDCP1 expression is coupled to MAPK signaling in cells and mice.
Figure 7C:
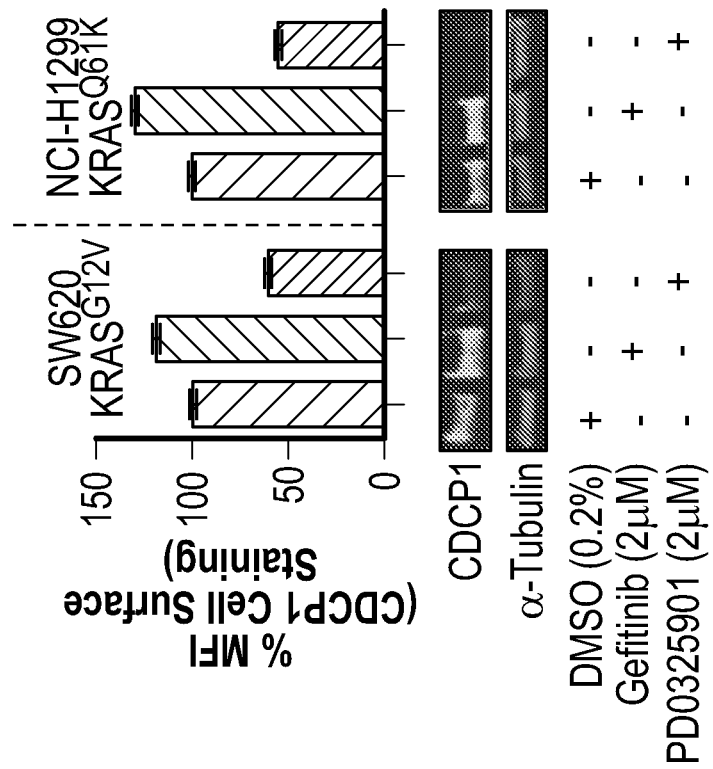
Figure 7B:
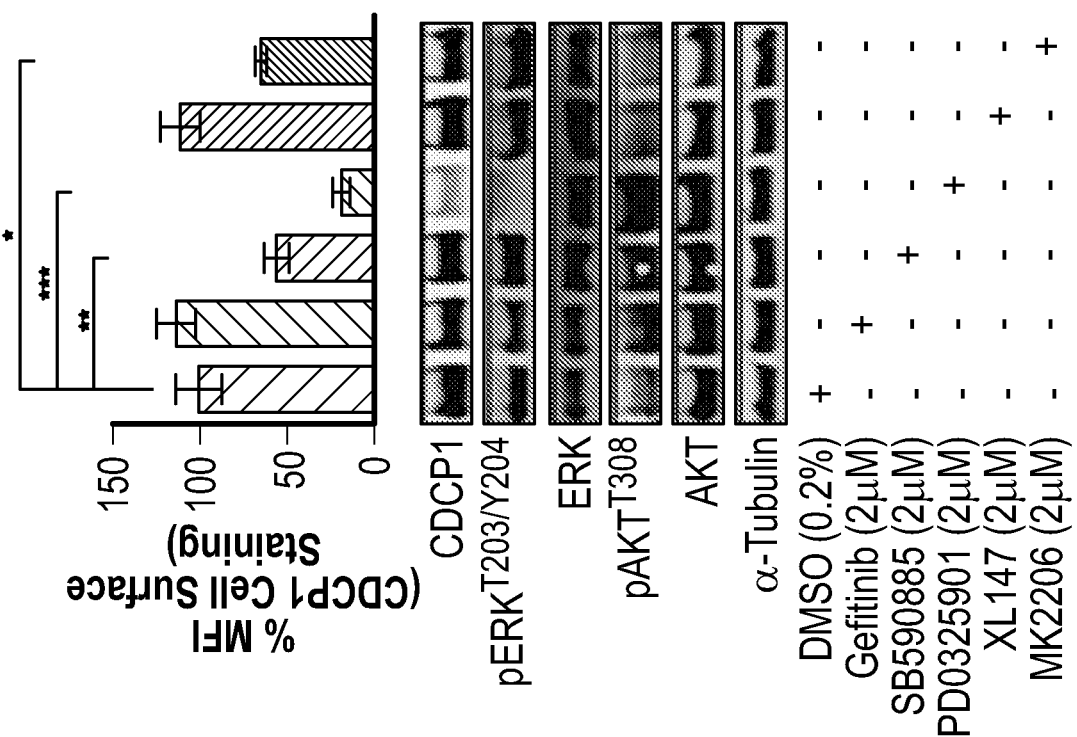
Figure 7D:
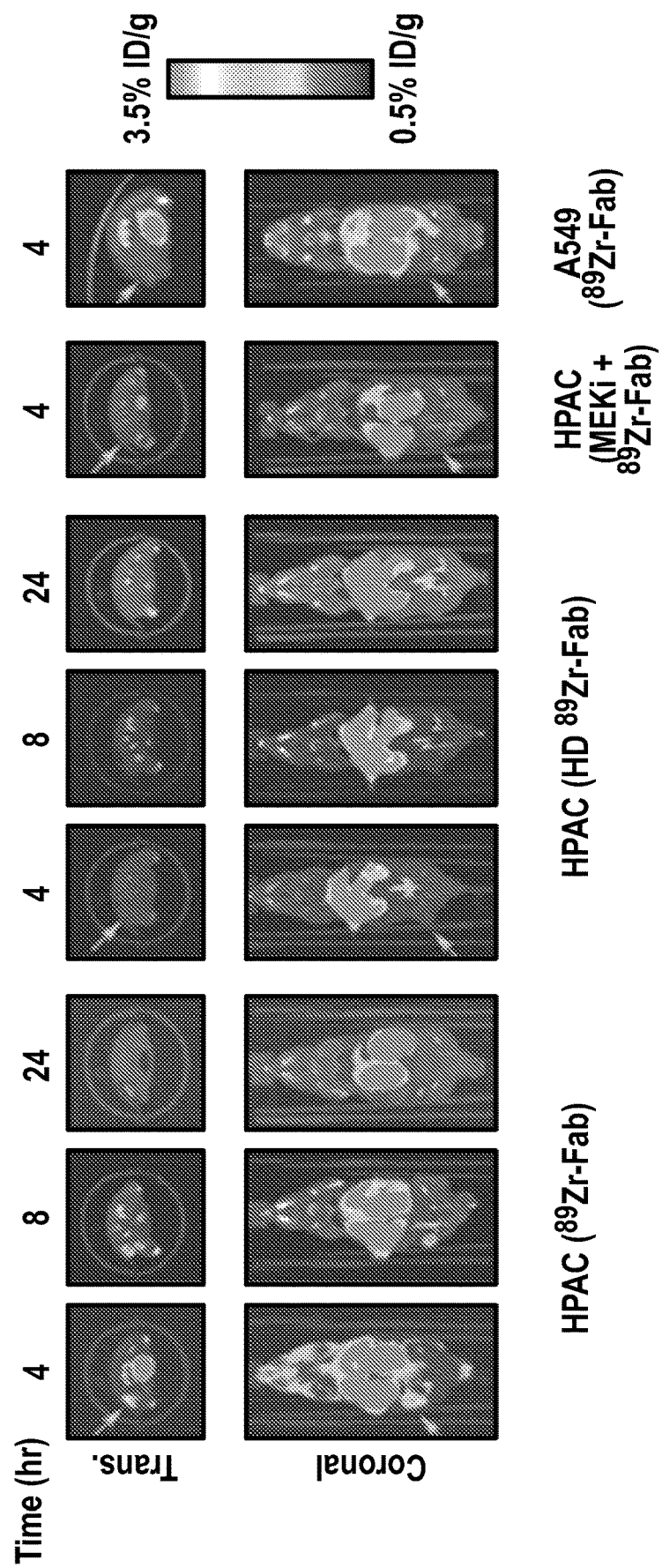
Figure 7E:
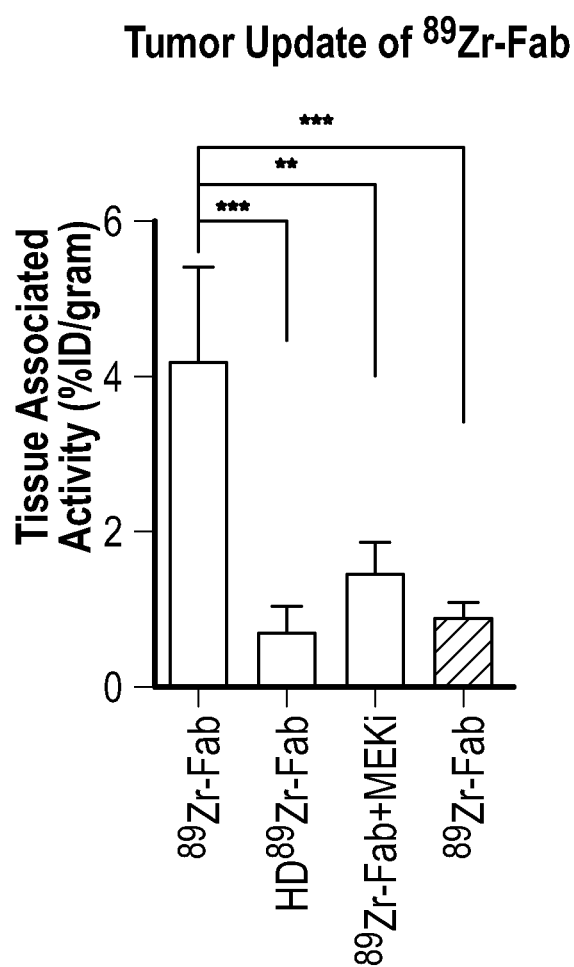

Example 5: A CDCP1 Antibody can be Used for In Vivo Detection of Oncogenic RAS-Dependent MAPK Signaling A mouse xenograft model for pancreatic cancer was used to determine whether CDCP1 expression levels could be used as an in vivo imaging marker for RAS signaling. The CDCP1-002 Fab was labeled with a positron-emitting radioisotope $^{89}$Zr and used for positron-emission-tomography (PET) imaging in mice with mutant RAS HPAC xenographs. As a negative control, $^{89}$Zr-Fab was heat denatured prior to administration. As an additional control, xenograft mouse models with A549 cells that express only 60,000 copies of CDCP1 per cell (FIG. 6A). Although A549 cells also harbor an oncogenic RAS mutation, previous work has shown that growth and MAPK signaling in these cells are not significantly diminished by knockdown of KRAS (Singh et al., Cancer Cell, 15:489-5000, 2009). Within four hours of administration of the $^{89}$Zr-Fab, tumor localization was observed, and by eight hours staining was highly pronounced (FIG. 7D). Significantly reduced tumor staining was observed using the heat-denatured $^{89}$Zr-Fab. Strikingly, in the HPAC xenograft mice treated with subtoxic MEKi, $^{89}$Zr-Fab tumor localization was also highly diminished. These animal data provide further evidence of CDCP1 expression being a consequence of RAS-dependent MAPK-signaling even in the complex milieu of a tumor. Excised tumors were used to quantify PET signal, confirming the trends seen in the qualitative images (FIG. 7I).

We claim:
1. An antibody or antibody fragment that specifically binds a CUB domain-containing protein 1 (CDCP1) ectodomain, comprising a light chain CDR1 comprising SEQ ID NO:11, a light chain CDR2 comprising SEQ ID NO:13, and
   (a) a light chain CDR3 comprising one of the group consisting of SEQ ID NO:20, and heavy chain CDRs of SEQ ID NO:17, SEQ ID NO:18, and SEQ ID NO:19;
   (b) a light chain CDR3 comprising SEQ ID NO:24, and heavy chain CDRs of SEQ ID NO:21, SEQ ID NO:22, and SEQ ID NO:23;
   (c) a light chain CDR3 comprising SEQ ID NO:28, and heavy chain CDRs of SEQ ID NO:25, SEQ ID NO:26, and SEQ ID NO:27;
   (d) a light chain CDR3 comprising SEQ ID NO:32, and heavy chain CDRs of SEQ ID NO:29, SEQ ID NO:30, and SEQ ID NO:31;
   (e) a light chain CDR3 comprising SEQ ID NO:36, and heavy chain CDRs of SEQ ID NO:33, SEQ ID NO:34, and SEQ ID NO:35;
   (f) a light chain CDR3 comprising SEQ ID NO:40, and heavy chain CDRs of SEQ ID NO:37, SEQ ID NO:38, and SEQ ID NO:39;
   (g) a light chain CDR3 comprising SEQ ID NO:44, and heavy chain CDRs of SEQ ID NO:41, SEQ ID NO:42, and SEQ ID NO:43;
   (h) a light chain CDR3 comprising SEQ ID NO:48, and heavy chain CDRs of SEQ ID NO:45, SEQ ID NO:46, and SEQ ID NO:47;
   (i) a light chain CDR3 comprising SEQ ID NO:52, and heavy chain CDRs of SEQ ID NO:49, SEQ ID NO:50, and SEQ ID NO:51; or
   (j) a light chain CDR3 comprising SEQ ID NO:56, and heavy chain CDRs of SEQ ID NO:53, SEQ ID NO:54, and SEQ ID NO:55.

2. The antibody or antibody fragment of claim 1, comprising light chain CDRs of SEQ ID NO:11, SEQ ID NO:13 and SEQ ID NO:20, and comprising heavy chain CDRs of SEQ ID NO:17, SEQ ID NO:18, and SEQ ID NO:19.

3. The antibody or antibody fragment of claim 1, wherein the antibody or antibody fragment comprises at least one heavy chain variable domain (VH) and at least one light chain variable domain (VL), wherein:
   (a) the VH comprises the amino acid sequence of SEQ ID NO:57, and the VL comprises the amino acid sequence of SEQ ID NO:58;
   (b) the VH comprises the amino acid sequence of SEQ ID NO:59, and the VL comprises the amino acid sequence of SEQ ID NO:60;
   (c) the VH comprises the amino acid sequence of SEQ ID NO:61, and the VL comprises the amino acid sequence of SEQ ID NO:62;
   (d) the VH comprises the amino acid sequence of SEQ ID NO:63, and the VL comprises the amino acid sequence of SEQ ID NO:64;
   (e) the VH comprises the amino acid sequence of SEQ ID NO:65, and the VL comprises the amino acid sequence of SEQ ID NO:66;
   (f) the VH comprises the amino acid sequence of SEQ ID NO:67, and the VL comprises the amino acid sequence of SEQ ID NO:68;
   (g) the VH comprises the amino acid sequence of SEQ ID NO:69, and the VL comprises the amino acid sequence of SEQ ID NO:70;
   (h) the VH comprises the amino acid sequence of SEQ ID NO:71, and the VL comprises the amino acid sequence of SEQ ID NO:72;
   (i) the VH comprises the amino acid sequence of SEQ ID NO:73, and the VL comprises the amino acid sequence of SEQ ID NO:74; or
   (j) the VH comprises the amino acid sequence of SEQ ID NO:75, and the VL comprises the amino acid sequence of SEQ ID NO:76.

4. The antibody or antibody fragment of claim 3, wherein the VH comprises the amino acid sequence of SEQ ID NO:57, and the VL comprises the amino acid sequence of SEQ ID NO:58.

5. The antibody or antibody fragment of claim 1, wherein the antibody or antibody fragment further comprises a cytotoxic agent conjugated to the antibody or antibody fragment.

6. The antibody or antibody fragment of claim 1, wherein the antibody or antibody fragment further comprises a binding domain that specifically binds to CD3 on the surface of cytotoxic T-cells.

7. The antibody or antibody fragment of claim 1, wherein the antibody or antibody fragment further comprises a detectable label conjugated to the antibody or antibody fragment.

8. A nucleic acid encoding the antibody or antibody fragment of claim 1.

9. An expression vector comprising the nucleic acid of claim 8 in operable combination with a promoter.

10. A host cell comprising the expression vector of claim 9.

11. A pharmaceutical composition comprising the antibody or antibody fragment of claim 1 and a pharmaceutically acceptable carrier.

12. A method of treating cancer in a subject having cancer, the method comprising administering to the subject a therapeutically effective amount of the antibody or antibody fragment of claim 1, wherein cancer cells of the subject comprise a G12V RAS mutation and/or express CDCP1.

13. The method of claim 12, wherein the cancer cells of the subject comprise a G12V RAS mutation.

14. The method of claim 12, wherein the cancer cells of the subject express CDCP1.

15. The method of claim 12, wherein the cancer cells are pancreatic ductal adenocarcinoma (PDAC) cells.

16. The method of claim 12, wherein the cancer is selected from the group consisting of pancreatic cancer and colorectal cancer.

17. The method of claim 12, wherein the cancer is selected from the group consisting of acute myeloid leukemia and melanoma.

18. The method of claim 12, wherein the cancer is bladder cancer.

19. A method of detecting cancer cells, the method comprising administering the antibody or antibody fragment of claim 7 to the cells, and detecting the binding of the antibody or antibody fragment to the cells.

20. A method of detecting cancer cells, the method comprising administering the antibody or antibody fragment of claim 1 to the cells, and detecting the binding of the antibody or antibody fragment to the cells.

* * * * *